United States Patent
Awiszus et al.

(10) Patent No.: US 11,925,232 B2
(45) Date of Patent: Mar. 12, 2024

(54) HEARING PROTECTOR WITH POSITIONAL AND SOUND MONITORING SENSORS FOR PROACTIVE SOUND HAZARD AVOIDANCE

(71) Applicant: 3M INNOVATIVE PROPERTIES COMPANY, St. Paul, MN (US)

(72) Inventors: Steven T. Awiszus, Woodbury, MN (US); Kiran S. Kanukurthy, Cottage Grove, MN (US); Eric C. Lobner, Woodbury, MN (US); Robert J. Quintero, St. Paul, MN (US); Micayla A. Johnson, Farmington, MN (US); Madeleine E. Filloux, St. Paul, MN (US); Caroline M. Ylitalo, Stillwater, MN (US); Paul A. Martinson, Maplewood, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1477 days.

(21) Appl. No.: 16/310,893

(22) PCT Filed: Jun. 23, 2017

(86) PCT No.: PCT/US2017/039003
§ 371 (c)(1),
(2) Date: Dec. 18, 2018

(87) PCT Pub. No.: WO2017/223451
PCT Pub. Date: Dec. 28, 2017

(65) Prior Publication Data
US 2019/0175960 A1    Jun. 13, 2019

Related U.S. Application Data

(63) Continuation of application No. 15/190,564, filed on Jun. 23, 2016, now Pat. No. 10,610,708.
(Continued)

(51) Int. Cl.
*H04R 1/08* (2006.01)
*A42B 1/0188* (2021.01)
(Continued)

(52) U.S. Cl.
CPC ............ *A42B 3/225* (2013.01); *A42B 1/0188* (2021.01); *A42B 3/0453* (2013.01); *A42B 3/046* (2013.01);
(Continued)

(58) Field of Classification Search
CPC .... H04R 1/1083; H04R 1/1041; H04R 3/007; H04R 29/004; A61F 11/14; A61F 11/06; A42B 3/0466; A42B 1/0188
(Continued)

(56) References Cited

U.S. PATENT DOCUMENTS 3,362,403 A    1/1968 Fleming
4,549,541 A    10/1985 Sundahl
(Continued)

FOREIGN PATENT DOCUMENTS

CN    104622470    11/2013
GB    2409961    7/2005
(Continued)

OTHER PUBLICATIONS

NFPA 1404, Standard for Fire Service Respiratory Protection Training, 2013 Edition.
(Continued)

*Primary Examiner* — Disler Paul
(74) *Attorney, Agent, or Firm* — Christopher D. Karlen; Steven A. Bern; Sriram Srinivasan

(57) ABSTRACT

In some examples, a system (1900) includes a hearing protector (1920); at least one position sensor; at least one sound monitoring sensor; at least one computing device configured to: receive, from the at least one sound monitor-
(Continued)

ing sensor and over a time duration, indications of sound levels to which a worker is exposed; determine, from the at least one position sensor and during the time duration, that the hearing protector is not positioned at one or more ears of the worker to attenuate the sound levels; and generate, in response to the determination that at least one of the sound levels satisfies an exposure threshold during the time duration and the hearing protector is not positioned at one or more ears of the worker to attenuate the sound levels, an indication for output.

16 Claims, 22 Drawing Sheets

Related U.S. Application Data

(60) Provisional application No. 62/408,564, filed on Oct. 14, 2016.

(51) Int. Cl.

| | | |
|---|---|---|
| *A42B 3/04* | (2006.01) | |
| *A42B 3/22* | (2006.01) | |
| *A61F 9/06* | (2006.01) | |
| *A61F 11/14* | (2006.01) | |
| *G02F 1/133* | (2006.01) | |
| *A42B 3/16* | (2006.01) | |
| *A62B 9/00* | (2006.01) | |
| *A62B 18/00* | (2006.01) | |
| *A62B 18/04* | (2006.01) | |
| *A62B 27/00* | (2006.01) | |
| *G06N 7/00* | (2023.01) | |
| *G06N 20/00* | (2019.01) | |
| *H04R 1/10* | (2006.01) | |

(52) U.S. Cl.
CPC ............ *A42B 3/0466* (2013.01); *A61F 9/067* (2013.01); *A61F 9/068* (2013.01); *A61F 11/14* (2013.01); *G02F 1/13318* (2013.01); *A42B 3/16* (2013.01); *A62B 9/00* (2013.01); *A62B 9/006* (2013.01); *A62B 18/00* (2013.01); *A62B 18/045* (2013.01); *A62B 27/00* (2013.01); *G06N 7/00* (2013.01); *G06N 20/00* (2019.01); *H04R 1/1083* (2013.01)

(58) Field of Classification Search
USPC .............................. 381/56–57, 72, 74, 72.4
See application file for complete search history.

(56) References Cited

U.S. PATENT DOCUMENTS

| | | | |
|---|---|---|---|
| 4,619,255 A | 10/1986 | Spinosa et al. | |
| 5,189,735 A | 3/1993 | Corona | |
| 5,245,994 A | 9/1993 | Chang et al. | |
| 5,666,949 A | 9/1997 | Debe | |
| 5,796,341 A | 8/1998 | Stratiotis | |
| 6,186,140 B1 | 2/2001 | Hoague | |
| 6,456,199 B1 | 9/2002 | Michael | |
| 6,472,988 B1 | 10/2002 | Feld | |
| 6,734,393 B1 | 5/2004 | Friedl | |
| 6,887,293 B1 | 5/2005 | Abad | |
| 7,019,652 B2 | 3/2006 | Richardson | |
| 7,080,414 B1 | 7/2006 | Montero et al. | |
| 7,592,911 B1 | 9/2009 | Hudgens | |
| 7,768,409 B2 | 8/2010 | Parias | |
| 7,792,615 B2 | 9/2010 | Aimar | |
| 8,294,580 B2 | 10/2012 | Witwer | |
| 8,316,850 B2 | 11/2012 | Grilliot et al. | |
| 9,294,856 B2* | 3/2016 | Goldstein | ............. H04R 3/002 |
| 10,157,037 B2* | 12/2018 | Patel | .................... H04R 1/1041 |
| 11,083,378 B2* | 8/2021 | LeBoeuf | .............. A61B 5/4848 |
| 11,265,644 B2* | 3/2022 | Kara | .................... H04R 1/1066 |
| 2003/0000001 A1 | 1/2003 | McDonald et al. | |
| 2004/0004547 A1 | 1/2004 | Appelt | |
| 2004/0100384 A1 | 5/2004 | Chen | |
| 2005/0114154 A1 | 5/2005 | Wolkowicz | |
| 2005/0238181 A1* | 10/2005 | Nilsson | ................ H04R 1/1083 381/72 |
| 2006/0044140 A1 | 3/2006 | Berg | |
| 2006/0085367 A1 | 4/2006 | Genovese | |
| 2006/0125623 A1 | 6/2006 | Appelt et al. | |
| 2007/0078528 A1 | 4/2007 | Anke | |
| 2007/0101995 A1 | 5/2007 | Chornyj | |
| 2008/0018472 A1 | 1/2008 | Dasilva | |
| 2008/0021919 A1 | 1/2008 | Kaartinen | |
| 2008/0241805 A1 | 10/2008 | Schantz | |
| 2008/0302360 A1 | 12/2008 | Chambers | |
| 2009/0125460 A1 | 5/2009 | Hewison | |
| 2009/0210989 A1 | 8/2009 | Becker | |
| 2009/0231423 A1 | 9/2009 | Becker | |
| 2010/0095439 A1 | 4/2010 | Nolan | |
| 2010/0107292 A1 | 5/2010 | Chevallier et al. | |
| 2011/0056496 A1 | 3/2011 | Tilley et al. | |
| 2011/0227700 A1 | 9/2011 | Hamerly | |
| 2013/0063550 A1 | 3/2013 | Ritchey | |
| 2013/0139816 A1 | 6/2013 | Proctor | |
| 2013/0144130 A1 | 6/2013 | Russell | |
| 2013/0291271 A1 | 11/2013 | Becker | |
| 2015/0010158 A1 | 1/2015 | Broadley | |
| 2015/0181972 A1 | 7/2015 | Djerassi | |
| 2016/0073722 A1 | 3/2016 | Eustace | |
| 2016/0106174 A1 | 4/2016 | Chung | |
| 2016/0355262 A1 | 12/2016 | Sharma | |
| 2017/0022807 A1 | 1/2017 | Dursan et al. | |
| 2017/0330444 A1 | 11/2017 | M R | |

FOREIGN PATENT DOCUMENTS

| | | |
|---|---|---|
| SU | 888993 | 12/1981 |
| WO | WO 2009/141474 | 11/2009 |
| WO | WO 2009134940 | 11/2009 |
| WO | 2011050401 A1 | 5/2011 |
| WO | WO 2016/089708 | 6/2016 |
| WO | WO 2017/223367 | 12/2017 |
| WO | WO 2017/223476 | 12/2017 |

OTHER PUBLICATIONS

Wang; Practice of internet of things and environmental supervision (7 pages).
Sandulescu, "Wearable System for Stress Monitoring of Firefighters in Special Missions", The 5*th* IEEE International Conference on E-Health and Bioengineering—EHB 2015, Nov. 19-21, 2015, pp. 1-4.
Machine Learning from Wikipedia, the free encyclopedia, retrieved from the internet Mar. 16, 2016, pp. 1-13.
"Modeling Human Performance in Chemical Protective Suits", Murray, 2010, Proceedings of the 2010 Industrial Engineering Research Conference.
"Outbreak Agent: Intelligent Wearable Technology for Hazardous Environments", Rogers, 1997, IEEE, 0-7803-4053, pp. 3198-3203.
"Artificial Intelligence" Russell, 2003, Prentice Hall.
"Evaluating the Physiological Performance of a Liquid Cooling Garment Used to Control Heat Stress in Hazmat Protective Ensembles", Semeniuk, 2005, Journal of ASTM International, Feb. 2005, vol. 2, No. 2.
New York Times article "Pogonip" in Pittsburg Air published Jan. 12, 1910.

\* cited by examiner

HEARING PROTECTOR WITH POSITIONAL AND SOUND MONITORING SENSORS FOR PROACTIVE SOUND HAZARD AVOIDANCE

This application claims the benefit of U.S. application Ser. No. 15/190,564, filed Jun. 23, 2016 and U.S. Provisional Application 62/408,564 filed Oct. 14, 2016, the entire content of each of which are hereby expressly incorporated by reference herein.

TECHNICAL FIELD

The present disclosure relates to the field of personal protective equipment. More specifically, the present disclosure relates to personal protective equipment that generate data.

BACKGROUND

When working in areas where there is known to be, or there is a potential of there being, dusts, fumes, gases, airborne contaminants, fall hazards, hearing hazards or any other hazards that are potentially hazardous or harmful to health, it is usual for a worker to use personal protective equipment, such as respirator or a clean air supply source. While a large variety of personal protective equipment are available, some commonly used devices include powered air purifying respirators (PAPR), self-contained breathing apparatuses, fall protection harnesses, ear muffs, face shields, and welding masks. For instance, a PAPR typically includes a blower system comprising a fan powered by an electric motor for delivering a forced flow of air through a tube to a head top worn by a user. A PAPR typically includes a device that draws ambient air through a filter, forces the air through a breathing tube and into a helmet or head top to provide filtered air to a user's breathing zone, around their nose or mouth. An SCBA provides clean air from a compressed air tank through a tube or hose to the interior of a head top worn by a user. In some examples, various personal protective equipment may generate various types of data.

SUMMARY

The present disclosure is directed to a system for detecting the positioning of a hearing protector at a worker and proactively notifying the worker if sound exposure exceeds an unsafe or threshold level. For instance, the hearing protector may include a position sensor that indicates whether the hearing protector is positioned at the worker to attenuate sound (e.g., ear muffs covering or not covering the worker's ears). A computing device communicatively coupled to the position sensor may receive indications of sound levels to which the user is exposed. The computing device may determine that the hearing protector is not positioned at one or more ears of the worker to attenuate sound during a time duration when sound levels exceed an exposure threshold or the worker is about to experience sound levels that exceed the exposure threshold. In response to determining that the hearing protector is not positioned to attenuate sound and the sound levels exceed an exposure threshold, the computing device may generate an indication for output such as an audio, visual, or haptic alert. By monitoring sound levels and the position of the hearing protector at the worker, the computing device may proactively generate notifications that the worker must wear the hearing protector in a position that attenuates the sound to which the worker is exposed. In this way, the system of the present disclosure may reduce errors in the use of hearing protectors, more quickly notify workers when hearing protectors are required, and/or reduce the potential for hearing loss in a worker.

In some examples, a system includes a hearing protector; at least one position sensor; at least one sound monitoring sensor; at least one computing device communicatively coupled to the at least one position sensor and the at least one sound monitoring sensor, the at least one computing device comprising a memory and one or more computer processors that: receive, from the at least one sound monitoring sensor and over a time duration, indications of sound levels to which a worker is exposed; determine, from the at least one position sensor and during the time duration, that the hearing protector is not positioned at one or more ears of the worker to attenuate the sound levels; and generate, in response to the determination that at least one of the sound levels satisfies an exposure threshold during the time duration and the hearing protector is not positioned at one or more ears of the worker to attenuate the sound levels, an indication for output.

In some examples, a hearing protector includes a head-mounted device; at least one position sensor coupled to the head-mounted device; one or more ear muffs coupled to the at least one position sensor; and a computing device communicatively coupled to the at least one position sensor and the at least one sound monitoring sensor, the at least one computing device comprising a memory and one or more computer processors to: receive, from at least one sound monitoring sensor and over a time duration, indications of sound levels to which a worker is exposed; determine, from the at least one position sensor and during the time duration, that the hearing protector is not positioned at one or more ears of the worker to attenuate the sound levels; and generate, in response to the determination that at least one of the sound levels satisfies an exposure threshold during the time duration and the hearing protector is not positioned at one or more ears of the worker to attenuate the sound levels, an indication for output.

In some examples, a method includes receiving, by a computing device, from at least one sound monitoring sensor and over a time duration, indications of sound levels to which a worker is exposed; determining, from at least one position sensor and during the time duration, that a hearing protector is not positioned at one or more ears of the worker to attenuate the sound levels; and generating, in response to determining that at least one of the sound levels satisfies an exposure threshold during the time duration and the hearing protector is not positioned at one or more ears of the worker to attenuate the sound levels, an indication for output.

In some examples, a computing device includes a memory; and one or more computer processors that: receive, from at least one sound monitoring sensor and over a time duration, indications of sound levels to which a worker is exposed; determine, from at least one position sensor and during the time duration, that the hearing protector is not positioned at one or more ears of the worker to attenuate the sound levels; and generate, in response to determining that at least one of the sound levels satisfies a threshold during the time duration and the hearing protector is not positioned at one or more ears of the worker to attenuate the sound levels, an indication for output.

The details of one or more examples of the disclosure are set forth in the accompanying drawings and the description below. Other features, objects, and advantages of the disclosure will be apparent from the description and drawings, and from the claims.

BRIEF DESCRIPTION OF THE DRAWINGS

FIGS. 9-16 illustrate example user interfaces for representing usage data from one or more respirators, according to aspects of this disclosure.

Figure 1:
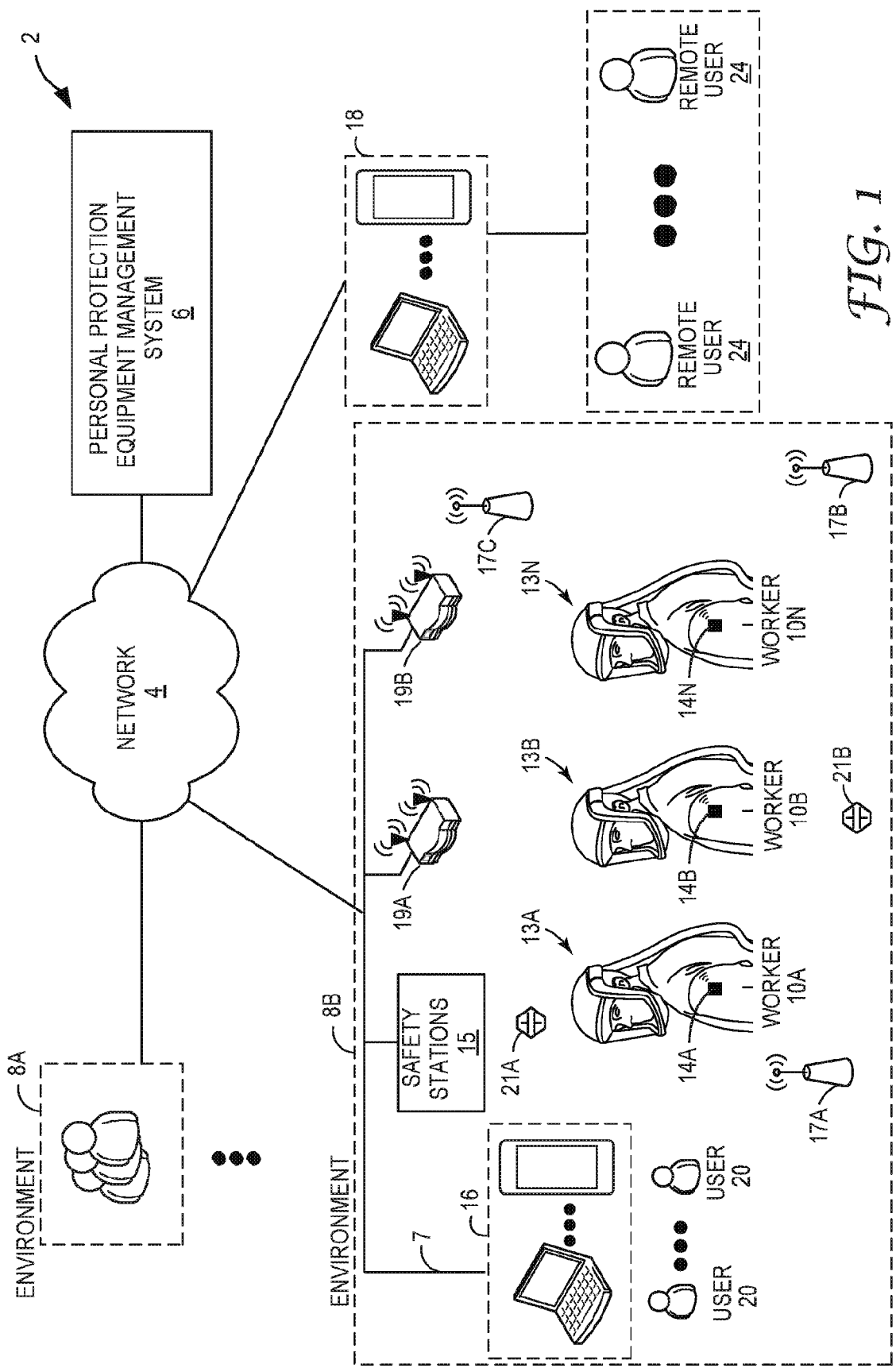
FIG. 1 is a block diagram illustrating an example system in which personal protection equipment (PPEs), such as filtered air respirator systems, having embedded sensors and communication capabilities are utilized within a number of work environments and are managed by a personal protection equipment management system (PPEMS) in accordance with various techniques of this disclosure.

It is to be understood that the embodiments may be utilized and structural changes may be made without departing from the scope of the invention. The figures are not necessarily to scale. Like numbers used in the figures refer to like components. However, it will be understood that the use of a number to refer to a component in a given figure is not intended to limit the component in another figure labeled with the same number.

DETAILED DESCRIPTION

According to aspects of this disclosure, an article of PPE may include sensors for capturing data that is indicative of operation, location, or environmental conditions surrounding an article of PPE. Sensors may include any device that generates data or context information. Such data may generally be referred to herein as usage data or, alternatively, operation data or sensor data. In some examples, usage data may take the form of a stream of samples over a period of time. In some instances, the sensors may be configured to measure operating characteristics of components of the article of PPE, characteristics of a worker using or wearing the article of PPE, and/or environmental factors associated with an environment in which the article of PPE is located. Moreover, as described herein, the article of PPE may be configured to include one or more electronic components for outputting communication to the respective worker, such as speakers, vibration devices, LEDs, buzzers or other devices for outputting alerts, audio messages, sounds, indicators and the like.

According to aspects of this disclosure, articles of PPE may be configured to transmit the acquired usage data to a personal protection equipment management system (PPEMS), which may be a cloud-based system having an analytics engine configured to process streams of incoming usage data from personal protection equipment deployed and used by a population of workers at various work environments. The analytics engine of the PPEMS may apply the streams of incoming usage data (or at least a subset of the usage data) to one or more models to monitor and predict the likelihood of an occurrence of a safety event for the worker associated with any individual article of PPE. For example, the analytics engine may compare measured parameters (e.g., as measured by the electronic sensors) to known models that characterize activity of a user of an article of PPE, e.g., that represent safe activities, unsafe activities, or activities of concern (which may typically occur prior to unsafe activities) in order to determine the probability of an event occurring.

The analytics engine may generate an output in response to predicting the likelihood of the occurrence of a safety event. For example, the analytics engine may generate an output that indicates a safety event is likely to occur based on data collected from a user of an article of PPE. The output may be used to alert the user of the article of PPE that the safety event is likely to occur, allowing the user to alter their behavior. In other examples, circuitry embedded within the respirators or processors within intermediate data hubs more local to the workers may be programmed via the PPEMS or other mechanism to apply models or rule sets determined by the PPEMS so as to locally generate and output alerts or other preventative measure designed to avoid or mitigate a predicted safety event. In this way, the techniques provide tools to accurately measure and/or monitor operation of a respirator and determine predictive outcomes based on the operation. Although certain examples of this disclosure are provided with respect to certain types of PPE for illustration purposes, the systems, techniques, and devices of this disclosure are applicable to any type of PPE.

FIG. 1 is a block diagram illustrating an example computing system 2 that includes a personal protection equipment management system (PPEMS) 6 for managing personal protection equipment. As described herein, PPEMS allows authorized users to perform preventive occupational health and safety actions and manage inspections and maintenance of safety protective equipment. By interacting with PPEMS 6, safety professionals can, for example, manage area inspections, worker inspections, worker health and safety compliance training.

In general, PPEMS 6 provides data acquisition, monitoring, activity logging, reporting, predictive analytics, PPE control, and alert generation. For example, PPEMS 6 includes an underlying analytics and safety event prediction engine and alerting system in accordance with various examples described herein. In general, a safety event may refer to activities of a user of personal protective equipment (PPE), a condition of the PPE, or an environmental condition (e.g., which may be hazardous). In some examples, a safety event may be an injury or worker condition, workplace harm, or regulatory violation. For example, in the context of fall protection equipment, a safety event may be misuse of the fall protection equipment, a user of the fall equipment experiencing a fall, or a failure of the fall protection equipment. In the context of a respirator, a safety event may be misuse of the respirator, a user of the respirator not receiving an appropriate quality and/or quantity of air, or failure of the respirator. A safety event may also be associated with a hazard in the environment in which the PPE is located. In some examples, occurrence of a safety event associated with the article of PPE may include a safety event in the environment in which the PPE is used or a safety event associated with a worker using the article of PPE. In some examples, a safety event may be an indication that PPE, a worker, and/or a worker environment are operating, in use, or acting in a way that is normal operation, where normal operation is a predetermined or predefined condition of acceptable or safe operation, use, or activity.

As further described below, PPEMS 6 provides an integrated suite of personal safety protection equipment management tools and implements various techniques of this disclosure. That is, PPEMS 6 provides an integrated, end-to-end system for managing personal protection equipment, e.g., safety equipment, used by workers 10 within one or more physical environments 8, which may be construction sites, mining or manufacturing sites or any physical environment. The techniques of this disclosure may be realized within various parts of computing environment 2.

As shown in the example of FIG. 1, system 2 represents a computing environment in which a computing device within of a plurality of physical environments 8A, 8B (collectively, environments 8) electronically communicate with PPEMS 6 via one or more computer networks 4. Each of physical environment 8 represents a physical environment, such as a work environment, in which one or more individuals, such as workers 10, utilize personal protection equipment while engaging in tasks or activities within the respective environment.

In this example, environment 8A is shown as generally as having workers 10, while environment 8B is shown in expanded form to provide a more detailed example. In the example of FIG. 1, a plurality of workers 10A-10N are shown as utilizing respective respirators 13A-13N.

As further described herein, each of respirators 13 includes embedded sensors or monitoring devices and processing electronics configured to capture data in real-time as a user (e.g., worker) engages in activities while wearing the respirators. For example, as described in greater detail herein, respirators 13 may include a number of components (e.g., a head top, a blower, a filter, and the like) respirators 13 may include a number of sensors for sensing or controlling the operation of such components. A head top may include, as examples, a head top visor position sensor, a head top temperature sensor, a head top motion sensor, a head top impact detection sensor, a head top position sensor, a head top battery level sensor, a head top head detection sensor, an ambient noise sensor, or the like. A blower may include, as examples, a blower state sensor, a blower pressure sensor, a blower run time sensor, a blower temperature sensor, a blower battery sensor, a blower motion sensor, a blower impact detection sensor, a blower position sensor, or the like. A filter may include, as examples, a filter presence sensor, a filter type sensor, or the like. Each of the above-noted sensors may generate usage data, as described herein.

In addition, each of respirators 13 may include one or more output devices for outputting data that is indicative of operation of respirators 13 and/or generating and outputting communications to the respective worker 10. For example, respirators 13 may include one or more devices to generate audible feedback (e.g., one or more speakers), visual feedback (e.g., one or more displays, light emitting diodes (LEDs) or the like), or tactile feedback (e.g., a device that vibrates or provides other haptic feedback).

In general, each of environments 8 include computing facilities (e.g., a local area network) by which respirators 13 are able to communicate with PPEMS 6. For example, environments 8 may be configured with wireless technology, such as 802.11 wireless networks, 802.15 ZigBee networks, and the like. In the example of FIG. 1, environment 8B includes a local network 7 that provides a packet-based transport medium for communicating with PPEMS 6 via network 4. In addition, environment 8B includes a plurality of wireless access points 19A, 19B that may be geographically distributed throughout the environment to provide support for wireless communications throughout the work environment.

Each of respirators 13 is configured to communicate data, such as sensed motions, events and conditions, via wireless communications, such as via 802.11 WiFi protocols, Bluetooth protocol or the like. Respirators 13 may, for example, communicate directly with a wireless access point 19. As another example, each worker 10 may be equipped with a respective one of wearable communication hubs 14A-14M that enable and facilitate communication between respirators 13 and PPEMS 6. For example, respirators 13 as well as other PPEs (such as fall protection equipment, hearing protection, hardhats, or other equipment) for the respective worker 10 may communicate with a respective communication hub 14 via Bluetooth or other short range protocol, and the communication hubs may communicate with PPEMs 6 via wireless communications processed by wireless access points 19. Although shown as wearable devices, hubs 14 may be implemented as stand-alone devices deployed within environment 8B. In some examples, hubs 14 may be articles of PPE.

In general, each of hubs 14 operates as a wireless device for respirators 13 relaying communications to and from respirators 13, and may be capable of buffering usage data in case communication is lost with PPEMS 6. Moreover, each of hubs 14 is programmable via PPEMS 6 so that local alert rules may be installed and executed without requiring a connection to the cloud. As such, each of hubs 14 provides a relay of streams of usage data from respirators 13 and/or other PPEs within the respective environment, and provides a local computing environment for localized alerting based on streams of events in the event communication with PPEMS 6 is lost.

As shown in the example of FIG. 1, an environment, such as environment 8B, may also include one or more wireless-enabled beacons, such as beacons 17A-17C, that provide accurate location information within the work environment. For example, beacons 17A-17C may be GPS-enabled such that a controller within the respective beacon may be able to precisely determine the position of the respective beacon. Based on wireless communications with one or more of beacons 17, a given respirator 13 or communication hub 14 worn by a worker 10 is configured to determine the location of the worker within work environment 8B. In this way, event data (e.g., usage data) reported to PPEMS 6 may be stamped with positional information to aid analysis, reporting and analytics performed by the PPEMS.

In addition, an environment, such as environment 8B, may also include one or more wireless-enabled sensing stations, such as sensing stations 21A, 21B. Each sensing station 21 includes one or more sensors and a controller configured to output data indicative of sensed environmental conditions. Moreover, sensing stations 21 may be positioned within respective geographic regions of environment 8B or otherwise interact with beacons 17 to determine respective positions and include such positional information when reporting environmental data to PPEMS 6. As such, PPEMS 6 may be configured to correlate the sense environmental conditions with the particular regions and, therefore, may utilize the captured environmental data when processing event data received from respirators 13. For example, PPEMS 6 may utilize the environmental data to aid generating alerts or other instructions for respirators 13 and for performing predictive analytics, such as determining any correlations between certain environmental conditions (e.g., heat, humidity, visibility) with abnormal worker behavior or increased safety events. As such, PPEMS 6 may utilize current environmental conditions to aid prediction and avoidance of imminent safety events. Example environmental conditions that may be sensed by sensing stations 21 include but are not limited to temperature, humidity, presence of gas, pressure, visibility, wind and the like.

In example implementations, an environment, such as environment 8B, may also include one or more safety stations 15 distributed throughout the environment to provide viewing stations for accessing respirators 13. Safety stations 15 may allow one of workers 10 to check out respirators 13 and/or other safety equipment, verify that safety equipment is appropriate for a particular one of environments 8, and/or exchange data. For example, safety stations 15 may transmit alert rules, software updates, or firmware updates to respirators 13 or other equipment. Safety stations 15 may also receive data cached on respirators 13, hubs 14, and/or other safety equipment. That is, while respirators 13 (and/or data hubs 14) may typically transmit usage data from sensors of respirators 13 to network 4 in real time or near real time, in some instances, respirators 13 (and/or data hubs 14) may not have connectivity to network 4. In such instances, respirators 13 (and/or data hubs 14) may store usage data locally and transmit the usage data to safety stations 15 upon being in proximity with safety stations 15. Safety stations 15 may then upload the data from respirators 13 and connect to network 4.

In addition, each of environments 8 include computing facilities that provide an operating environment for end-user computing devices 16 for interacting with PPEMS 6 via network 4. For example, each of environments 8 typically includes one or more safety managers responsible for overseeing safety compliance within the environment. In general, each user 20 interacts with computing devices 16 to access PPEMS 6. Each of environments 8 may include systems. Similarly, remote users may use computing devices 18 to interact with PPEMS via network 4. For purposes of example, the end-user computing devices 16 may be laptops, desktop computers, mobile devices such as tablets or so-called smart phones and the like.

Users 20, 24 interact with PPEMS 6 to control and actively manage many aspects of safely equipment utilized by workers 10, such as accessing and viewing usage records, analytics and reporting. For example, users 20, 24 may review usage information acquired and stored by PPEMS 6, where the usage information may include data specifying starting and ending times over a time duration (e.g., a day, a week, or the like), data collected during particular events, such as lifts of a visor of respirators 13, removal of respirators 13 from a head of workers 10, changes to operating parameters of respirators 13, status changes to components of respirators 13 (e.g., a low battery event), motion of workers 10, detected impacts to respirators 13 or hubs 14, sensed data acquired from the user, environment data, and the like. In addition, users 20, 24 may interact with PPEMS 6 to perform asset tracking and to schedule maintenance events for individual pieces of safety equipment, e.g., respirators 13, to ensure compliance with any procedures or regulations. PPEMS 6 may allow users 20, 24 to create and complete digital checklists with respect to the maintenance procedures and to synchronize any results of the procedures from computing devices 16, 18 to PPEMS 6.

Further, as described herein, PPEMS 6 integrates an event processing platform configured to process thousand or even millions of concurrent streams of events from digitally enabled PPEs, such as respirators 13. An underlying analytics engine of PPEMS 6 applies historical data and models to the inbound streams to compute assertions, such as identified anomalies or predicted occurrences of safety events based on conditions or behavior patterns of workers 10. Further, PPEMS 6 provides real-time alerting and reporting to notify workers 10 and/or users 20, 24 of any predicted events, anomalies, trends, and the like.

The analytics engine of PPEMS 6 may, in some examples, apply analytics to identify relationships or correlations between sensed worker data, environmental conditions, geographic regions and other factors and analyze the impact on safety events. PPEMS 6 may determine, based on the data acquired across populations of workers 10, which particular activities, possibly within certain geographic region, lead to, or are predicted to lead to, unusually high occurrences of safety events.

In this way, PPEMS 6 tightly integrates comprehensive tools for managing personal protection equipment with an underlying analytics engine and communication system to provide data acquisition, monitoring, activity logging, reporting, behavior analytics and alert generation. Moreover, PPEMS 6 provides a communication system for operation and utilization by and between the various elements of system 2. Users 20, 24 may access PPEMS 6 to view results on any analytics performed by PPEMS 6 on data acquired from workers 10. In some examples, PPEMS 6 may present a web-based interface via a web server (e.g., an HTTP server) or client-side applications may be deployed for devices of computing devices 16, 18 used by users 20, 24, such as desktop computers, laptop computers, mobile devices such as smartphones and tablets, or the like.

In some examples, PPEMS 6 may provide a database query engine for directly querying PPEMS 6 to view acquired safety information, compliance information and any results of the analytic engine, e.g., by the way of dashboards, alert notifications, reports and the like. That is, users 24, 26, or software executing on computing devices 16, 18, may submit queries to PPEMS 6 and receive data corresponding to the queries for presentation in the form of one or more reports or dashboards (e.g., as shown in the examples of FIGS. 9-16). Such dashboards may provide various insights regarding system 2, such as baseline ("normal") operation across worker populations, identifications of any anomalous workers engaging in abnormal activities that may potentially expose the worker to risks, identifications of any geographic regions within environments 2 for which unusually anomalous (e.g., high) safety events have been or are predicted to occur, identifications of any of environments 2 exhibiting anomalous occurrences of safety events relative to other environments, and the like.

As illustrated in detail below, PPEMS 6 may simplify workflows for individuals charged with monitoring and ensure safety compliance for an entity or environment. That is, the techniques of this disclosure may enable active safety management and allow an organization to take preventative or correction actions with respect to certain regions within environments 8, particular pieces of safety equipment or individual workers 10, define and may further allow the entity to implement workflow procedures that are data-driven by an underlying analytical engine.

As one example, the underlying analytical engine of PPEMS 6 may be configured to compute and present customer-defined metrics for worker populations within a given environment 8 or across multiple environments for an organization as a whole. For example, PPEMS 6 may be configured to acquire data and provide aggregated performance metrics and predicted behavior analytics across a worker population (e.g., across workers 10 of either or both of environments 8A, 8B). Furthermore, users 20, 24 may set benchmarks for occurrence of any safety incidences, and PPEMS 6 may track actual performance metrics relative to the benchmarks for individuals or defined worker populations.

As another example, PPEMS 6 may further trigger an alert if certain combinations of conditions are present, e.g., to accelerate examination or service of a safety equipment, such as one of respirators 13. In this manner, PPEMS 6 may identify individual respirators 13 or workers 10 for which the metrics do not meet the benchmarks and prompt the users to intervene and/or perform procedures to improve the metrics relative to the benchmarks, thereby ensuring compliance and actively managing safety for workers 10.

Figure 2:
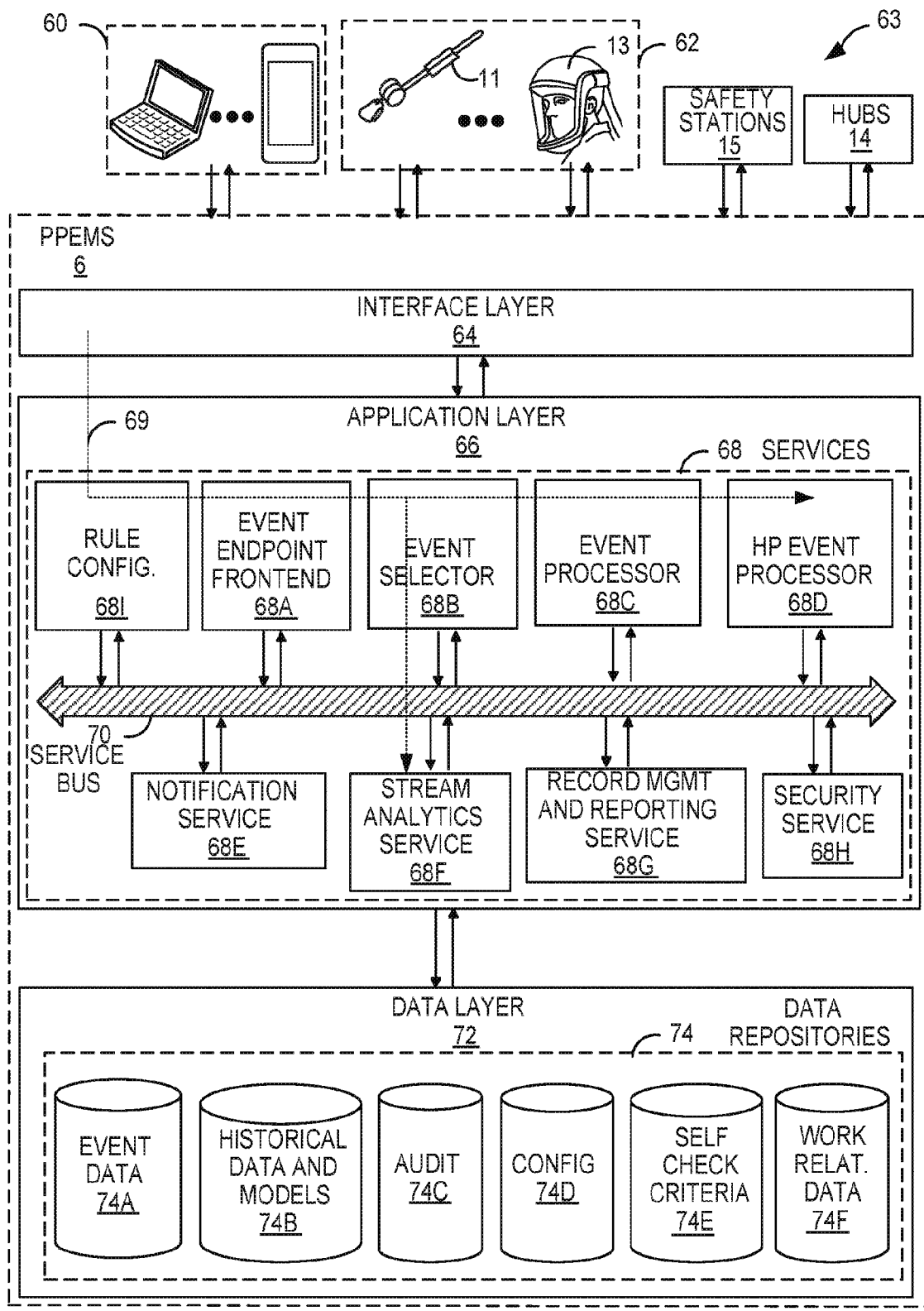
FIG. 2 is a block diagram illustrating an operating perspective of the personal protection equipment management system shown in FIG. 1 in accordance with various techniques of this disclosure.

FIG. 2 is a block diagram providing an operating perspective of PPEMS 6 when hosted as cloud-based platform capable of supporting multiple, distinct work environments 8 having an overall population of workers 10 that have a variety of communication enabled personal protection equipment (PPE), such as safety release lines (SRLs) 11, respirators 13, safety helmets, hearing protection or other safety equipment. In the example of FIG. 2, the components of PPEMS 6 are arranged according to multiple logical layers that implement the techniques of the disclosure. Each layer may be implemented by a one or more modules comprised of hardware, software, or a combination of hardware and software.

In FIG. 2, personal protection equipment (PPEs) 62, such as SRLs 11, respirators 13 and/or other equipment, either directly or by way of hubs 14, as well as computing devices 60, operate as clients 63 that communicate with PPEMS 6 via interface layer 64. Computing devices 60 typically execute client software applications, such as desktop applications, mobile applications, and web applications. Computing devices 60 may represent any of computing devices 16, 18 of FIG. 1. Examples of computing devices 60 may include, but are not limited to a portable or mobile computing device (e.g., smartphone, wearable computing device, tablet), laptop computers, desktop computers, smart television platforms, and servers, to name only a few examples.

As further described in this disclosure, PPEs 62 communicate with PPEMS 6 (directly or via hubs 14) to provide streams of data acquired from embedded sensors and other monitoring circuitry and receive from PPEMS 6 alerts, configuration and other communications. Client applications executing on computing devices 60 may communicate with PPEMS 6 to send and receive information that is retrieved, stored, generated, and/or otherwise processed by services 68. For instance, the client applications may request and edit safety event information including analytical data stored at and/or managed by PPEMS 6. In some examples, client applications 61 may request and display aggregate safety event information that summarizes or otherwise aggregates numerous individual instances of safety events and corresponding data acquired from PPEs 62 and or generated by PPEMS 6. The client applications may interact with PPEMS 6 to query for analytics information about past and predicted safety events, behavior trends of workers 10, to name only a few examples. In some examples, the client applications may output for display information received from PPEMS 6 to visualize such information for users of clients 63. As further illustrated and described in below, PPEMS 6 may provide information to the client applications, which the client applications output for display in user interfaces.

Clients applications executing on computing devices 60 may be implemented for different platforms but include similar or the same functionality. For instance, a client application may be a desktop application compiled to run on a desktop operating system, such as Microsoft Windows, Apple OS X, or Linux, to name only a few examples. As another example, a client application may be a mobile application compiled to run on a mobile operating system, such as Google Android, Apple iOS, Microsoft Windows Mobile, or BlackBerry OS to name only a few examples. As another example, a client application may be a web application such as a web browser that displays web pages received from PPEMS 6. In the example of a web application, PPEMS 6 may receive requests from the web application (e.g., the web browser), process the requests, and send one or more responses back to the web application. In this way, the collection of web pages, the client-side processing web application, and the server-side processing performed by PPEMS 6 collectively provides the functionality to perform techniques of this disclosure. In this way, client applications use various services of PPEMS 6 in accordance with techniques of this disclosure, and the applications may operate within various different computing environment (e.g., embedded circuitry or processor of a PPE, a desktop operating system, mobile operating system, or web browser, to name only a few examples).

As shown in FIG. 2, PPEMS 6 includes an interface layer 64 that represents a set of application programming interfaces (API) or protocol interface presented and supported by PPEMS 6. Interface layer 64 initially receives messages from any of clients 63 for further processing at PPEMS 6. Interface layer 64 may therefore provide one or more interfaces that are available to client applications executing on clients 63. In some examples, the interfaces may be application programming interfaces (APIs) that are accessible over a network. Interface layer 64 may be implemented with one or more web servers. The one or more web servers may receive incoming requests, process and/or forward information from the requests to services 68, and provide one or more responses, based on information received from services 68, to the client application that initially sent the request. In some examples, the one or more web servers that implement interface layer 64 may include a runtime environment to deploy program logic that provides the one or more interfaces. As further described below, each service may provide a group of one or more interfaces that are accessible via interface layer 64.

In some examples, interface layer 64 may provide Representational State Transfer (RESTful) interfaces that use HTTP methods to interact with services and manipulate resources of PPEMS 6. In such examples, services 68 may generate JavaScript Object Notation (JSON) messages that interface layer 64 sends back to the client application 61 that submitted the initial request. In some examples, interface layer 64 provides web services using Simple Object Access Protocol (SOAP) to process requests from client applications 61. In still other examples, interface layer 64 may use Remote Procedure Calls (RPC) to process requests from clients 63. Upon receiving a request from a client application to use one or more services 68, interface layer 64 sends the information to application layer 66, which includes services 68.

As shown in FIG. 2, PPEMS 6 also includes an application layer 66 that represents a collection of services for implementing much of the underlying operations of PPEMS 6. Application layer 66 receives information included in requests received from client applications 61 and further processes the information according to one or more of services 68 invoked by the requests. Application layer 66 may be implemented as one or more discrete software services executing on one or more application servers, e.g., physical or virtual machines. That is, the application servers provide runtime environments for execution of services 68. In some examples, the functionality interface layer 64 as described above and the functionality of application layer 66 may be implemented at the same server.

Application layer 66 may include one or more separate software services 68, e.g., processes that communicate, e.g., via a logical service bus 70 as one example. Service bus 70 generally represents a logical interconnections or set of interfaces that allows different services to send messages to other services, such as by a publish/subscription communication model. For instance, each of services 68 may subscribe to specific types of messages based on criteria set for the respective service. When a service publishes a message of a particular type on service bus 70, other services that subscribe to messages of that type will receive the message. In this way, each of services 68 may communicate information to one another. As another example, services 68 may communicate in point-to-point fashion using sockets or other communication mechanism. Before describing the functionality of each of services 68, the layers are briefly described herein.

Data layer 72 of PPEMS 6 represents a data repository that provides persistence for information in PPEMS 6 using one or more data repositories 74. A data repository, generally, may be any data structure or software that stores and/or manages data. Examples of data repositories include but are not limited to relational databases, multi-dimensional databases, maps, and hash tables, to name only a few examples. Data layer 72 may be implemented using Relational Database Management System (RDBMS) software to manage information in data repositories 74. The RDBMS software may manage one or more data repositories 74, which may be accessed using Structured Query Language (SQL). Information in the one or more databases may be stored, retrieved, and modified using the RDBMS software. In some examples, data layer 72 may be implemented using an Object Database Management System (ODBMS), Online Analytical Processing (OLAP) database or other suitable data management system.

As shown in FIG. 2, each of services 68A-68I ("services 68") is implemented in a modular form within PPEMS 6. Although shown as separate modules for each service, in some examples the functionality of two or more services may be combined into a single module or component. Each of services 68 may be implemented in software, hardware, or a combination of hardware and software. Moreover, services 68 may be implemented as standalone devices, separate virtual machines or containers, processes, threads or software instructions generally for execution on one or more physical processors.

In some examples, one or more of services 68 may each provide one or more interfaces that are exposed through interface layer 64. Accordingly, client applications of computing devices 60 may call one or more interfaces of one or more of services 68 to perform techniques of this disclosure.

In accordance with techniques of the disclosure, services 68 may include an event processing platform including an event endpoint frontend 68A, event selector 68B, event processor 68C and high priority (HP) event processor 68D. Event endpoint frontend 68A operates as a front end interface for receiving and sending communications to PPEs 62 and hubs 14. In other words, event endpoint frontend 68A operates to as a front line interface to safety equipment deployed within environments 8 and utilized by workers 10. In some instances, event endpoint frontend 68A may be implemented as a plurality of tasks or jobs spawned to receive individual inbound communications of event streams 69 from the PPEs 62 carrying data sensed and captured by the safety equipment. When receiving event streams 69, for example, event endpoint frontend 68A may spawn tasks to quickly enqueue an inbound communication, referred to as an event, and close the communication session, thereby providing high-speed processing and scalability. Each incoming communication may, for example, carry data recently captured data representing sensed conditions, motions, temperatures, actions or other data, generally referred to as events. Communications exchanged between the event endpoint frontend 68A and the PPEs may be real-time or pseudo real-time depending on communication delays and continuity.

Event selector 68B operates on the stream of events 69 received from PPEs 62 and/or hubs 14 via frontend 68A and determines, based on rules or classifications, priorities associated with the incoming events. Based on the priorities, event selector 68B enqueues the events for subsequent processing by event processor 68C or high priority (HP) event processor 68D. Additional computational resources and objects may be dedicated to HP event processor 68D so as to ensure responsiveness to critical events, such as incorrect usage of PPEs, use of incorrect filters and/or respirators based on geographic locations and conditions, failure to properly secure SRLs 11 and the like. Responsive to processing high priority events, HP event processor 68D may immediately invoke notification service 68E to generate alerts, instructions, warnings or other similar messages to be output to SRLs 11, respirators 13, hubs 14 and/or remote users 20, 24. Events not classified as high priority are consumed and processed by event processor 68C.

In general, event processor 68C or high priority (HP) event processor 68D operate on the incoming streams of events to update event data 74A within data repositories 74. In general, event data 74A may include all or a subset of usage data obtained from PPEs 62. For example, in some instances, event data 74A may include entire streams of samples of data obtained from electronic sensors of PPEs 62. In other instances, event data 74A may include a subset of such data, e.g., associated with a particular time period or activity of PPEs 62.

In some examples, as described in greater detail herein, respirators 13 may include a number of components such as, for example, a head top, a blower for blowing air to the head top, and a filter for filtering air. Table 1, shown below, includes a non-limiting set of usage data that may be obtained from respirators 13 with respect to the head top:

TABLE 1

| INPUT NAME | VALUE DEFINITION | DESCRIPTION |
|---|---|---|
| Head_Top_Visor_Position | OPEN, CLOSED | Head Top Visor Position: Open or Closed |
| Head_Top_Temp | −40° C. To 60° C. | Temperature: Inside Case Of Peripheral |
| Head_Top_Motion | MOTION, STILL | Motion: Is there any motion detected over the last x seconds? (Boolean) |
| Head_Top_Impact_Detect | YES, NO | Impact: Accelerometer G-Force that exceeded a threshold. |
| Head_Top_Upright_Position | PRONE, UPRIGHT | Posture: Is the wearer Upright or Prone? |
| Head_Top_Battery_Level | GOOD, REPLACE SOON, REPLACE NOW | Battery: Good, Replace Soon, Replace Now |
| Head_Top_Head_Detected | YES, NO | Head Detected: Yes, No |
| Head_Top_Ambient_Noise_Level | QUIET, NORMAL, LOUD, DANGER | Ambient Noise Level: Normal, Moderate, Loud, Danger |
| Head_Top_Firmware_Revision | | Firmware revision number: |
| Head_Top_Hardware_Revision_PWA | | Hardware revision numbers: (PWA) |
| Head_Top_Hardware_Revision_PWB | | Hardware revision numbers: (PWB) |
| Head_Top_Serial_Number | | Head Top Peripheral Serial Number: |

Table 2, shown below, includes a non-limiting set of usage data that may be obtained from respirators 13 with respect to a blower:

TABLE 2

| INPUT NAME | VALUE DEFINITION | DESCRIPTION |
|---|---|---|
| TR600_Blower_Temperature | −40° C. To 60° C. | Temperature: Circuitry Of Blower |
| TR600_Blower_Motion | MOTION, STILL | Motion: Is there any motion detected over the last x seconds? (Boolean) |
| Motion: Standard accelerometer data for 6 axis. Linear and angular acceleration data stream. | | Motion: Standard accelerometer data for 6 axis. Linear and angular acceleration data stream. |
| TR600_Blower_Impact_Detect | YES, NO | Impact: Accelerometer G-Force that exceeded a threshold. |
| TR600_Blower_Upright_Position | PRONE, UPRIGHT | Posture: Is the wearer Upright or Prone? |
| TR600_Blower_Battery_Estimated_Run_Time | 0 To 960 Minutes | Estimated remaining battery run time under current running conditions |
| TR600_Battery_Percent_Of_Full | 0 To 100 | Battery Percent Of Full Charge (State Of Charge) |
| TR600_Battery_Replacement_Status | GOOD, REPLACE SOON, REPLACE NOW | Battery (State Of Health): Good, Replace Soon, Replace Now |
| TR600_Particulate_Filter_Range | 0 To 100 | LED's On Blower Display |
| TR600_Filter_Is_Equipped? | YES, NO | Filter (Is One Detected?) |
| TR600_Filter_Type | 16 Bit Field, 0000h = UNKNOWN | Filter Type: Particulate, OV, etc. |
| TR600_Filter_Loading_Status | 0 To 100 | Filter Loading Status: % Of Filter consumed. |
| Filter Cumulative Run Time: Minutes of total run time. | | Filter Cumulative Run Time: Minutes of total run time. |
| Filter Manufacturing Date: | | Filter Manufacturing Date: |
| Filter Shelf Life Expiration Date: | | Filter Shelf Life Expiration Date: |
| Filter Start Use Date: | | Filter Start Use Date: |
| Filter Change Out Date: | | Filter Change Out Date: |

Table 3, shown below, includes a non-limiting set of usage data that may be obtained from respirators 13 with respect to a filter:

TABLE 3

| INPUT NAME | VALUE DEFINITION | DESCRIPTION |
|---|---|---|
| Filter Status: Active, Decommissioned, etc. | | Filter Status: Active, Decommissioned, etc. |
| TR600_Blower_State | LOW, MED, HI | Low, Med, Hi speed selected on the blower panel. |

TABLE 3-continued

| INPUT NAME | VALUE DEFINITION | DESCRIPTION |
| --- | --- | --- |
| TR600__Blower__Alarms | 16 Bit Field | Blower Alarms: Low Flow + any other. (Ask Keith M.) |
| TR600__Head__Top__Configuration | LOOSE, TIGHT | Head Top Configuration: Loose or Tight fitting. |
| Firmware revision number | | Firmware revision number |
| Blower serial number | | Blower serial number |
| Pressure reading | | Pressure reading |
| Blower Total Run Time | | Blower Total Run Time |
| Blower Calculated Air Flow | | Blower Calculated Air Flow |
| Battery serial number | | Battery serial number |

Event processors 68C, 68D may create, read, update, and delete event information stored in event data 74A. Event information for may be stored in a respective database record as a structure that includes name/value pairs of information, such as data tables specified in row/column format. For instance, a name (e.g., column) may be "worker ID" and a value may be an employee identification number. An event record may include information such as, but not limited to: worker identification, PPE identification, acquisition timestamp(s) and data indicative of one or more sensed parameters.

In addition, event selector 68B directs the incoming stream of events to stream analytics service 68F, which is configured to perform in depth processing of the incoming stream of events to perform real-time analytics. Stream analytics service 68F may, for example, be configured to process and compare multiple streams of event data 74A with historical data and models 74B in real-time as event data 74A is received. In this way, stream analytic service 68D may be configured to detect anomalies, transform incoming event data values, trigger alerts upon detecting safety concerns based on conditions or worker behaviors. Historical data and models 74B may include, for example, specified safety rules, business rules and the like. In addition, stream analytic service 68D may generate output for communicating to PPPEs 62 by notification service 68F or computing devices 60 by way of record management and reporting service 68D.

In this way, analytics service 68F processes inbound streams of events, potentially hundreds or thousands of streams of events, from enabled safety PPEs 62 utilized by workers 10 within environments 8 to apply historical data and models 74B to compute assertions, such as identified anomalies or predicted occurrences of imminent safety events based on conditions or behavior patterns of the workers. Analytics service may 68D publish the assertions to notification service 68F and/or record management by service bus 70 for output to any of clients 63.

In this way, analytics service 68F may be configured as an active safety management system that predicts imminent safety concerns and provides real-time alerting and reporting. In addition, analytics service 68F may be a decision support system that provides techniques for processing inbound streams of event data to generate assertions in the form of statistics, conclusions, and/or recommendations on an aggregate or individualized worker and/or PPE basis for enterprises, safety officers and other remote users. For instance, analytics service 68F may apply historical data and models 74B to determine, for a particular worker, the likelihood that a safety event is imminent for the worker based on detected behavior or activity patterns, environmental conditions and geographic locations. In some examples, analytics service 68F may determine whether a worker is currently impaired, e.g., due to exhaustion, sickness or alcohol/drug use, and may require intervention to prevent safety events. As yet another example, analytics service 68F may provide comparative ratings of workers or type of safety equipment in a particular environment 8.

Hence, analytics service 68F may maintain or otherwise use one or more models that provide risk metrics to predict safety events. Analytics service 68F may also generate order sets, recommendations, and quality measures. In some examples, analytics service 68F may generate user interfaces based on processing information stored by PPEMS 6 to provide actionable information to any of clients 63. For example, analytics service 68F may generate dashboards, alert notifications, reports and the like for output at any of clients 63. Such information may provide various insights regarding baseline ("normal") operation across worker populations, identifications of any anomalous workers engaging in abnormal activities that may potentially expose the worker to risks, identifications of any geographic regions within environments for which unusually anomalous (e.g., high) safety events have been or are predicted to occur, identifications of any of environments exhibiting anomalous occurrences of safety events relative to other environments, and the like.

Although other technologies can be used, in one example implementation, analytics service 68F utilizes machine learning when operating on streams of safety events so as to perform real-time analytics. That is, analytics service 68F includes executable code generated by application of machine learning to training data of event streams and known safety events to detect patterns. The executable code may take the form of software instructions or rule sets and is generally referred to as a model that can subsequently be applied to event streams 69 for detecting similar patterns and predicting upcoming events.

Analytics service 68F may, in some example, generate separate models for a particular worker, a particular population of workers, a particular environment, or combinations thereof. Analytics service 68F may update the models based on usage data received from PPEs 62. For example, analytics service 68F may update the models for a particular worker, a particular population of workers, a particular environment, or combinations thereof based on data received from PPEs 62. In some examples, usage data may include incident reports, air monitoring systems, manufacturing production systems, or any other information that may be used to a train a model.

Alternatively, or in addition, analytics service 68F may communicate all or portions of the generated code and/or the machine learning models to hubs 16 (or PPEs 62) for execution thereon so as to provide local alerting in near-real time to PPEs. Example machine learning techniques that may be employed to generate models 74B can include various learning styles, such as supervised learning, unsupervised learning, and semi-supervised learning. Example types of algorithms include Bayesian algorithms, Clustering algorithms, decision-tree algorithms, regularization algorithms, regression algorithms, instance-based algorithms, artificial neural network algorithms, deep learning algorithms, dimensionality reduction algorithms and the like. Various examples of specific algorithms include Bayesian Linear Regression, Boosted Decision Tree Regression, and Neural Network Regression, Back Propagation Neural Networks, the Apriori algorithm, K-Means Clustering, k-Nearest Neighbour (kNN), Learning Vector Quantization (LUQ), Self-Organizing Map (SOM), Locally Weighted Learning (LWL), Ridge Regression, Least Absolute Shrinkage and Selection Operator (LASSO), Elastic Net, and Least-Angle Regression (LARS), Principal Component Analysis (PCA) and Principal Component Regression (PCR).

Record management and reporting service 68G processes and responds to messages and queries received from computing devices 60 via interface layer 64. For example, record management and reporting service 68G may receive requests from client computing devices for event data related to individual workers, populations or sample sets of workers, geographic regions of environments 8 or environments 8 as a whole, individual or groups/types of PPEs 62. In response, record management and reporting service 68G accesses event information based on the request. Upon retrieving the event data, record management and reporting service 68G constructs an output response to the client application that initially requested the information. In some examples, the data may be included in a document, such as an HTML document, or the data may be encoded in a JSON format or presented by a dashboard application executing on the requesting client computing device. For instance, as further described in this disclosure, example user interfaces that include the event information are depicted in the figures.

As additional examples, record management and reporting service 68G may receive requests to find, analyze, and correlate PPE event information. For instance, record management and reporting service 68G may receive a query request from a client application for event data 74A over a historical time frame, such as a user can view PPE event information over a period of time and/or a computing device can analyze the PPE event information over the period of time.

In example implementations, services 68 may also include security service 68H that authenticate and authorize users and requests with PPEMS 6. Specifically, security service 68H may receive authentication requests from client applications and/or other services 68 to access data in data layer 72 and/or perform processing in application layer 66. An authentication request may include credentials, such as a username and password. Security service 68H may query security data 74A to determine whether the username and password combination is valid. Configuration data 74D may include security data in the form of authorization credentials, policies, and any other information for controlling access to PPEMS 6. As described above, security data 74A may include authorization credentials, such as combinations of valid usernames and passwords for authorized users of PPEMS 6. Other credentials may include device identifiers or device profiles that are allowed to access PPEMS 6.

Security service 68H may provide audit and logging functionality for operations performed at PPEMS 6. For instance, security service 68H may log operations performed by services 68 and/or data accessed by services 68 in data layer 72. Security service 68H may store audit information such as logged operations, accessed data, and rule processing results in audit data 74C. In some examples, security service 68H may generate events in response to one or more rides being satisfied. Security service 68H may store data indicating the events in audit data 74C.

In the example of FIG. 2, a safety manager may initially configure one or more safety rules. As such, remote user 24 may provide one or more user inputs at computing device 18 that configure a set of safety rules for work environment 8A and 8B. For instance, a computing device 60 of the safety manager may send a message that defines or specifies the safety rules. Such message may include data to select or create conditions and actions of the safety rules. PPEMS 6 may receive the message at interface layer 64 which forwards the message to rule configuration component 68I. Rule configuration component 68I may be combination of hardware and/or software that provides for rule configuration including, but not limited to: providing a user interface to specify conditions and actions of rules, receive, organize, store, and update rules included in safety rules data store 74E.

Safety rules data store 75E may be a data store that includes data representing one or more safety rules. Safety rules data store 74E may be any suitable data store such as a relational database system, online analytical processing database, object-oriented database, or any other type of data store. When rule configuration component 68I receives data defining safety rules from computing device 60 of the safety manager, rule configuration component 68I may store the safety rules in safety rules data store 75E.

In some examples, storing the safety rules may include associating a safety rule with context data, such that rule configuration component 68I may perform a lookup to select safety rules associated with matching context data. Context data may include any data describing or characterizing the properties or operation of a worker, worker environment, article of PPE, or any other entity. Context data of a worker may include, but is not limited to: a unique identifier of a worker, type of worker, role of worker, physiological or biometric properties of a worker, experience of a worker, training of a worker, time worked by a worker over a particular time interval, location of the worker, or any other data that describes or characterizes a worker. Context data of an article of PPE may include, but is not limited to: a unique identifier of the article of PPE; a type of PPE of the article of PPE; a usage time of the article of PPE over a particular time interval; a lifetime of the PPE; a component included within the article of PPE; a usage history across multiple users of the article of PPE; contaminants, hazards, or other physical conditions detected by the PPE, expiration date of the article of PPE; operating metrics of the article of PPE. Context data for a work environment may include, but is not limited to: a location of a work environment, a boundary or perimeter of a work environment, an area of a work environment, hazards within a work environment, physical conditions of a work environment, permits for a work environment, equipment within a work environment, owner of a work environment, responsible supervisor and/or safety manager for a work environment.

Table 4, shown below, includes a non-limiting set of rules that may be stored to safety rules data store 74E:

TABLE 4

SAFETY RULES

Hub shall immediately assert an "Attention Initial" Alert if Visor Position Status is OPEN in current location requiring Visor Open Allow = NO
Hub shall immediately assert a "Critical Initial" Alert if Filter Type Status is not equal to Filter Type or no filter found required by current location
Hub shall store all alerts in a queue.
Critical Alerts shall be highest priority in alert queue
Attention Alerts shall have secondary priority in alert queue
Hub shall immediately remove an alert from the queue if its conditions causing the alert have been corrected
A newly added alert to the alert queue shall be flagged as "Active", if it is higher priority than any other alarms in the queue.
A newly added alert to the alert queue shall be flagged as "Active", if all other alarms in the queue are Acknowledged or Notify
A newly added alert to the alert queue shall be flagged as "Pending" if an Active alert already exists in the queue and the newly added alert is lower in priority than the currently Active alert
If an Active alert in the queue is replaced by a new Active alert because of priority, the replaced alert shall be flagged as "Pending"
An active alert shall enable its respective haptic feedback and LED pattern
Hub shall assert an Acknowledge event when user presses and releases button within <3 seconds. (Button_Tap)
Upon an Acknowledge event the Hub shall immediately flag the currently Active alert as Acknowledged, if any Active alerts are in the queue.
An Acknowledged alert shall disable its respective haptic feedback and LED pattern
Upon an Acknowledge event the Hub shall immediately flag the highest priority Pending alert as Active, if any Pending alerts exist in the queue.
Upon an Acknowledge event the Hub shall immediately flag the highest priority Acknowledged alert as Notify, if no Active alerts or Pending exist in the queue.
A Notify alert shall disable its respective haptic feedback and enable its LED pattern
Immediate Cloud Updates - Hub shall send safety violation asserted message via Wi-Fi to cloud service immediately upon assertion of alert
Immediate Worker Interface Updates - Hub shall send safety rule violation alerts asserted message via BLE to Worker Interface immediately upon assertion of alert
Immediate Cloud Updates - Hub shall send safety violation deasserted message via Wi-Fi to cloud service immediately upon deassertion of alert
Immediate Worker Interface Updates - Hub shall send safety violation deasserted message via BLE to Worker Interface immediately upon deassertion of alert It should be understood that the examples of Table 4 are provided for purposes of illustration only, and that other rules may be developed.

Figure 4:
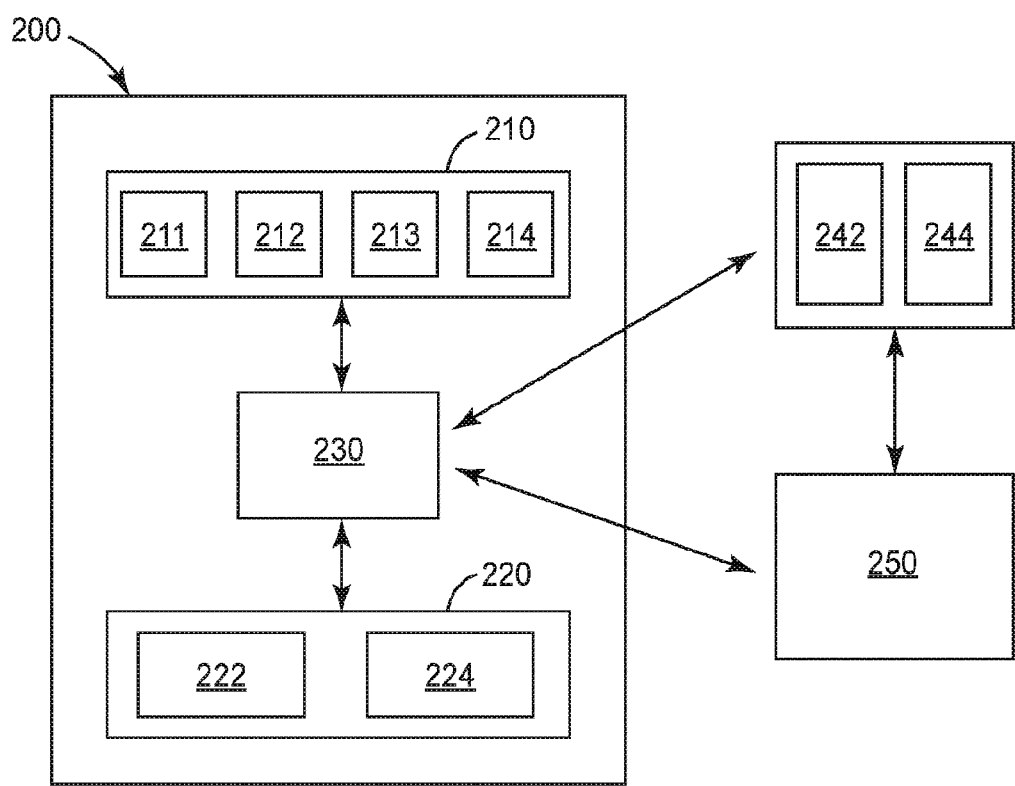
FIG. 4 is a block diagram of electronic components in an exposure indicating filtered air respirator system in accordance with various techniques of this disclosure.

According to aspects of this disclosure, the rules may be used for purposes of reporting, to generate alerts, or the like. In an example for purposes of illustration, worker 10A may be equipped with respirator 13A and data hub 14A. Respirator 13A may include a filter to remove particulates but not organic vapors. Data hub 14A may be initially configured with and store a unique identifier of worker 10A. When initially assigning the respirator 13A and data hub to worker 10A, a computing device operated by worker 10A and/or a safety manager may cause RMRS 68G to store a mapping in work relation data 74F. Work relation data 74F may include mappings between data that corresponds to PPE, workers, and work environments. Work relation data 74F may be any suitable datastore for storing, retrieving, updating and deleting data. RMRS 69G may store a mapping between the unique identifier of worker 10A and a unique device identifier of data hub 14A. Work relation data store 74F may also map a worker to an environment. In the example of FIG. 4, self-check component 68I may receive or otherwise determine data from work relation data 74F for data hub 14A, worker 10A, and/or PPE associated with or assigned to worker 10A.

Worker 10A may initially put on respirator 13A and data hub 14A prior to entering environment 8A. As worker 10A approaches environment 8A and/or has entered environment 8A, data hub 14A may determine that worker 10A is within a threshold distance of entering environment 8A or has entered environment 8A Data hub 14A may determine that it is within a threshold distance of entering environment 8A or has entered environment 8A and send a message that includes context data to PPEMS 6 that indicates data hub 14A is within a threshold distance of entering environment 8A.

According to aspects of this disclosure, as noted above, PPEMS 6 may additionally or alternatively apply analytics to predict the likelihood of a safety event. As noted above, a safety event may refer to activities of a worker 10 using PPE 62, a condition of PPE 62, or a hazardous environmental condition (e.g., that the likelihood of a safety event is relatively high, that the environment is dangerous, that SRL 11 is malfunctioning, that one or more components of SRL 11 need to be repaired or replaced, or the like). For example, PPEMS 6 may determine the likelihood of a safety event based on application of usage data from PPE 62 to historical data and models 74B. That is, PEMS 6 may apply historical data and models 74B to usage data from respirators 13 in order to compute assertions, such as anomalies or predicted occurrences of imminent safety events based on environmental conditions or behavior patterns of a worker using a respirator 13.

PPEMS 6 may apply analytics to identify relationships or correlations between sensed data from respirators 13, environmental conditions of environment in which respirators 13 are located, a geographic region in which respirators 13 are located, and/or other factors. PPEMS 6 may determine, based on the data acquired across populations of workers 10, which particular activities, possibly within certain environment or geographic region, lead to, or are predicted to lead to, unusually high occurrences of safety events. PPEMS 6 may generate alert data based on the analysis of the usage data and transmit the alert data to PPEs 62 and/or hubs 14. Hence, according to aspects of this disclosure, PPEMS 6 may determine usage data of respirator 13, generate status indications, determine performance analytics, and/or perform prospective/preemptive actions based on a likelihood of a safety event.

For example, according to aspects of this disclosure, usage data from respirators 13 may be used to determine usage statistics. For example, PPEMS 6 may determine, based on usage data from respirators 13, a length of time that one or more components of respirator 13 (e.g., head top, blower, and/or filter) have been in use, an instantaneous velocity or acceleration of worker 10 (e.g., based on an accelerometer included in respirators 13 or hubs 14), a temperature of one or more components of respirator 13 and/or worker 10, a location of worker 10, a number of times or frequency with which a worker 10 has performed a self-check of respirator 13 or other PPE, a number of times or frequency with which a visor of respirator 13 has been opened or closed, a filter/cartridge consumption rate, fan/blower usage (e.g., time in use, speed, or the like), battery usage (e.g., charge cycles), or the like.

According to aspects of this disclosure, PPEMS 6 may use the usage data to characterize activity of worker 10. For example, PPEMS 6 may establish patterns of productive and nonproductive time (e.g., based on operation of respirator 13 and/or movement of worker 10), categorize worker movements, identify key motions, and/or infer occurrence of key events. That is, PPEMS 6 may obtain the usage data, analyze the usage data using services 68 (e.g., by comparing the usage data to data from known activities/events), and generate an output based on the analysis.

In some examples, the usage statistics may be used to determine when respirator 13 is in need of maintenance or replacement. For example, PPEMS 6 may compare the usage data to data indicative of normally operating respirators 13 in order to identify defects or anomalies. In other examples, PPEMS 6 may also compare the usage data to data indicative of a known service life statistics of respirators 13. The usage statistics may also be used to provide an understanding how respirators 13 are used by workers 10 to product developers in order to improve product designs and performance. In still other examples, the usage statistics may be used to gathering human performance metadata to develop product specifications. In still other examples, the usage statistics may be used as a competitive benchmarking tool. For example, usage data may be compared between customers of respirators 13 to evaluate metrics (e.g. productivity, compliance, or the like) between entire populations of workers outfitted with respirators 13.

Additionally or alternatively, according to aspects of this disclosure, usage data from respirators 13 may be used to determine status indications. For example, PPEMS 6 may determine that a visor of a respirator 13 is up in hazardous work area. PPEMS 6 may also determine that a worker 10 is fitted with improper equipment (e.g., an improper filter for a specified area), or that a worker 10 is present in a restricted/closed area. PPEMS 6 may also determine whether worker temperature exceeds a threshold, e.g., in order to prevent heat stress. PPEMS 6 may also determine when a worker 10 has experienced an impact, such as a fall.

Additionally or alternatively, according to aspects of this disclosure, usage data from respirators 13 may be used to assess performance of worker 10 wearing respirator 13. For example, PPEMS 6 may, based on usage data from respirators 13, recognize motion that may indicate a pending fall by worker 10 (e.g., via one or more accelerometers included in respirators 13 and/or hubs 14). In some instances, PPEMS 6 may, based on usage data from respirators 13, infer that a fall has occurred or that worker 10 is incapacitated. PPEMS 6 may also perform fall data analysis after a fall has occurred and/or determine temperature, humidity and other environmental conditions as they relate to the likelihood of safety events.

As another example, PPEMS 6 may, based on usage data from respirators 13, recognize motion that may indicate fatigue or impairment of worker 10. For example, PPEMS 6 may apply usage data from respirators 13 to a safety learning model that characterizes a motion of a user of at least one respirator. In this example, PPEMS 6 may determine that the motion of a worker 10 over a time period is anomalous for the worker 10 or a population of workers 10 using respirators 13.

Additionally or alternatively, according to aspects of this disclosure, usage data from respirators 13 may be used to determine alerts and/or actively control operation of respirators 13. For example, PPEMS 6 may determine that a safety event such as equipment failure, a fall, or the like is imminent. PPEMS 6 may send data to respirators 13 to change an operating condition of respirators 13. In an example for purposes of illustration, PPEMS 6 may apply usage data to a safety learning model that characterizes an expenditure of a filter of one of respirators 13. In this example, PPEMS 6 may determine that the expenditure is higher than an expected expenditure for an environment, e.g., based on conditions sensed in the environment, usage data gathered from other workers 10 in the environment, or the like. PPEMS 6 may generate and transmit an alert to worker 10 that indicates that worker 10 should leave the environment and/or active control of respirator 13. For example, PPEMS 6 may cause respirator to reduce a blower speed of a blower of respirator 13 in order to provide worker 10 with substantial time to exit the environment.

PPEMS 6 may generate, in some examples, a warning when worker 10 is near a hazard in one of environments 8 (e.g., based on location data gathered from a location sensor (GPS or the like) of respirators 13). PPEMS 6 may also applying usage data to a safety learning model that characterizes a temperature of worker 10. In this example, PPEMS 6 may determine that the temperature exceeds a temperature associated with safe activity over the time period and alert worker 10 to the potential for a safety event due to the temperature.

In another example, PPEMS 6 may schedule preventative maintenance or automatically purchase components for respirators 13 based on usage data. For example, PPEMS 6 may determine a number of hours a blower of a respirator 13 has been in operation, and schedule preventative maintenance of the blower based on such data. PPEMS 6 may automatically order a filter for respirator 13 based on historical and/or current usage data from the filter.

Again, PPEMS 6 may determine the above-described performance characteristics and/or generate the alert data based on application of the usage data to one or more safety learning models that characterizes activity of a user of one of respirators 13. The safety learning models may be trained based on historical data or known safety events. However, while the determinations are described with respect to PPEMS 6, as described in greater detail herein, one or more other computing devices, such as hubs 14 or respirators 13 may be configured to perform all or a subset of such functionality.

In some examples, a safety learning model is trained using supervised and/or reinforcement learning techniques. The safety learning model may be implemented using any number of models for supervised and/or reinforcement learning, such as but not limited to, an artificial neural networks, a decision tree, naïve Bayes network, support vector machine, or k-nearest neighbor model, to name only a few examples. In some examples, PPEMS 6 initially trains the safety learning model based on a training set of metrics and corresponding to safety events. The training set may include a set of feature vectors, where each feature in the feature vector represents a value for a particular metric. As further example description, PPEMS 6 may select a training set comprising a set of training instances, each training instance comprising an association between usage data and a safety event. The usage data may comprise one or more metrics that characterize at least one of a user, a work environment, or one or more articles of PPE. PPEMS 6 may, for each training instance in the training set, modify, based on particular usage data and a particular safety event of the training instance, the safety learning model to change a likelihood predicted by the safety learning model for the particular safety event in response to subsequent usage data applied to the safety learning model. In some examples, the training instances may be based on real-time or periodic data generated while PPEMS 6 managing data for one or more articles of PPE, workers, and/or work environments. As such, one or more training instances of the set of training instances may be generated from use of one or more articles of PPE after PPEMS 6 performs operations relating to the detection or prediction of a safety event for PPE, workers, and/or work environments that are currently in use, active, or in operation.

Some example metrics may include any characteristics or data described in this disclosure that relate to PPE, a worker, or a work environment, to name only a few examples. For instance, example metrics may include but are not limited to: worker identity, worker motion, worker location, worker age, worker experience, worker physiological parameters (e.g., heart rate, temperature, blood oxygen level, chemical compositions in blood, or any other measureable physiological parameter), or any other data descriptive of a worker or worker behavior. Example metrics may include but are not limited to: PPE type, PPE usage, PPE age, PPE operations, or any other data descriptive of PPE or PPE use. Example metrics may include but are not limited to: work environment type, work environment location, work environment temperature, work environment hazards, work environment size, or any other data descriptive of a work environment.

Each feature vector may also have a corresponding safety event. As described in this disclosure, a safety event may include but is not limited to: activities of a user of personal protective equipment (PPE), a condition of the PPE, or a hazardous environmental condition to name only a few examples. By training a safety learning model based on the training set, a safety learning model may be configured by PPEMS 6 to, when applying a particular feature vector to the safety learning model, generate higher probabilities or scores for safety events that correspond to training feature vectors that are more similar to the particular feature set. In the same way, the safety learning model may be configured by PPEMS 6 to, when applying a particular feature vector to the safety learning model, generate lower probabilities or scores for safety events that correspond to training feature vectors that are less similar to the particular feature set. Accordingly, the safety learning model may be trained, such that upon receiving a feature vector of metrics, the safety learning model may output one or more probabilities or scores that indicate likelihoods of safety events based on the feature vector. As such, PPEMS 6 may select likelihood of the occurrence as a highest likelihood of occurrence of a safety event in the set of likelihoods of safety events.

In some instances, PPEMS 6 may apply analytics for combinations of PPE. For example, PPEMS 6 may draw correlations between users of respirators 13 and/or the other PPE (such as fall protection equipment, head protection equipment, hearing protection equipment, or the like) that is used with respirators 13. That is, in some instances, PPEMS 6 may determine the likelihood of a safety event based not only on usage data from respirators 13, but also from usage data from other PPE being used with respirators 13. In such instances, PPEMS 6 may include one or more safety learning models that are constructed from data of known safety events from one or more devices other than respirators 13 that are in use with respirators 13.

In some examples, a safety learning model is based on safety events from one or more of a worker, article of PPE, and/or work environment having similar characteristics (e.g., of a same type). In some examples the "same type" may refer to identical but separate instances of PPE. In other examples the "same type" may not refer to identical instances of PPE. For instance, although not identical, a same type may refer to PPE in a same class or category of PPE, same model of PPE, or same set of one or more shared functional or physical characteristics, to name only a few examples. Similarly, a same type of work environment or worker may refer to identical but separate instances of work environment types or worker types. In other examples, although not identical, a same type may refer to a worker or work environment in a same class or category of worker or work environment or same set of one or more shared behavioral, physiological, environmental characteristics, to name only a few examples.

In some examples, to apply the usage data to a model, PPEMS 6 may generate a structure, such as a feature vector, in which the usage data is stored. The feature vector may include a set of values that correspond to metrics (e.g., characterizing PPE, worker, work environment, to name a few examples), where the set of values are included in the usage data. The model may receive the feature vector as input, and based on one or more relations defined by the model (e.g., probabilistic, deterministic or other functions within the knowledge of one of ordinary skill in the art) that has been trained, the model may output one or more probabilities or scores that indicate likelihoods of safety events based on the feature vector.

In general, while certain techniques or functions are described herein as being performed by certain components, e.g., PPEMS 6, respirators 13, or hubs 14, it should be understood that the techniques of this disclosure are not limited in this way. That is, certain techniques described herein may be performed by one or more of the components of the described systems. For example, in some instances, respirators 13 may have a relatively limited sensor set and/or processing power. In such instances, one of hubs 14 and/or PPEMS 6 may be responsible for most or all of the processing of usage data, determining the likelihood of a safety event, and the like. In other examples, respirators 13 and/or hubs 14 may have additional sensors, additional processing power, and/or additional memory, allowing for respirators 13 and/or hubs 14 to perform additional techniques. Determinations regarding which components are responsible for performing techniques may be based, for example, on processing costs, financial costs, power consumption, or the like.

Figure 3:
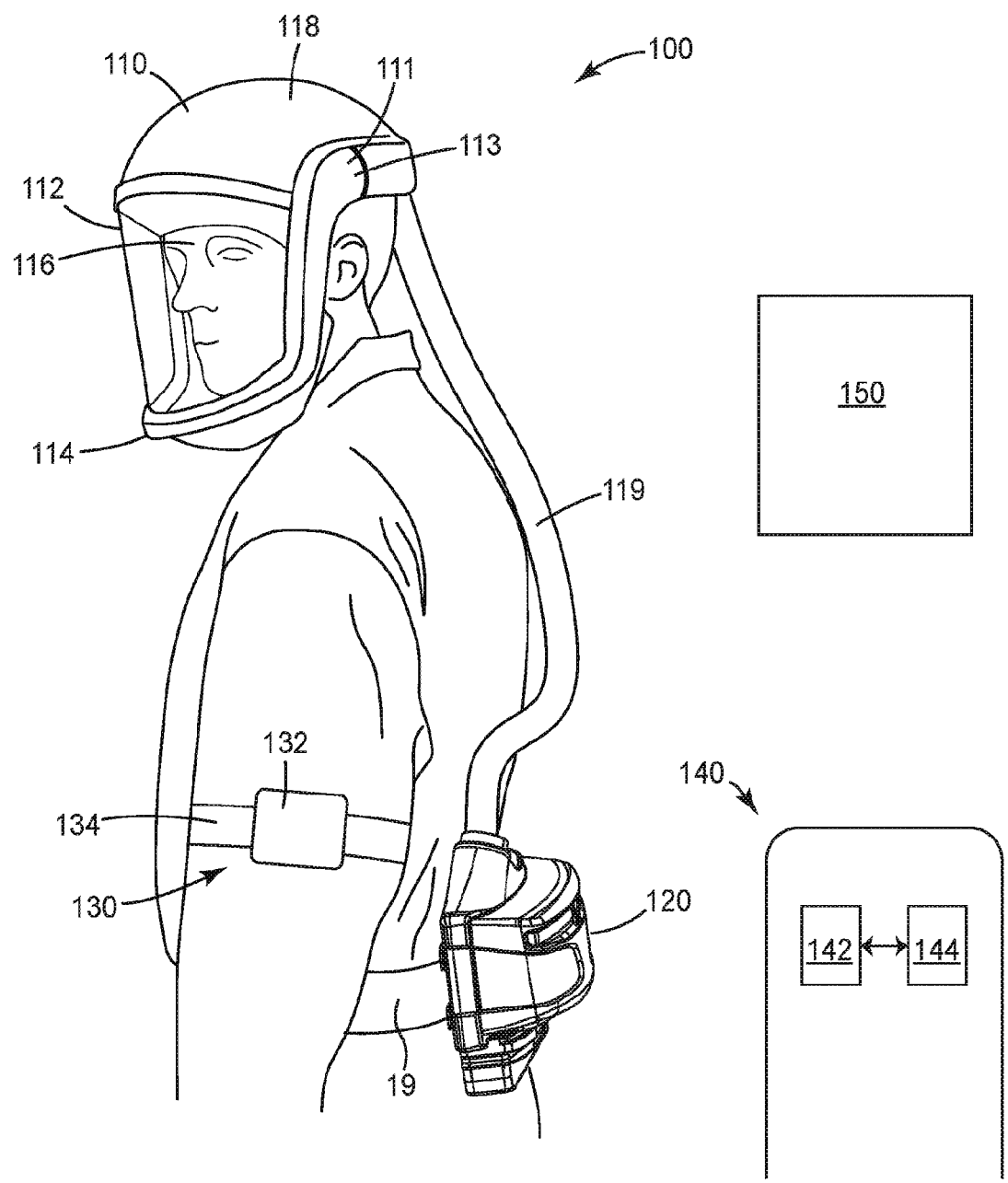
FIG. 3 is a system diagram of an exposure indicating filtered air respirator system in accordance with various techniques of this disclosure.

FIG. 3 is a system diagram of an exposure indicating filtered air respirator system 100, which may also be referred to as a supplied air system generally. System 100 represents one example of respirators 13 shown in FIG. 2. System 100 includes head top 110, clean air supply source 120, communication hub 130, environmental beacon 140 and PPEMS 150. Head top 110 is connected to clean air supply source 120 by hose 119. Clean air supply source 120 can be any type of air supply source, such as a blower assembly for a powered air purifying respirator (PAPR), an air tank for a self-contained breathing apparatus (SCBA) or any other device that provides air to head top 110. In FIG. 3, clean air supply source 120 is a blower assembly for a PAPR. A PAPR is commonly used by individuals working in areas where there is known to be, or there is a potential of there being dusts, fumes or gases that are potentially harmful or hazardous to health. A PAPR typically includes blower assembly, including a fan driven by an electric motor for delivering a forced flow of air to the respirator user. The air is passed from the PAPR blower assembly through hose 119 to the interior of head top 110.

Head top 110 includes a visor 112 that is sized to fit over at least a user's nose and mouth. Visor 112 includes lens 116 which is secured to helmet 118 by the frame assembly 114. Head top also includes a position sensor 111 that senses the position of visor 112 relative to helmet 118 to determine if the visor is in an open position or in a closed position. In some instances, position sensor 111 may detect whether visor 112 is partially open, and if so, what measure (e.g., percent or degree) it is open. As an example, the position sensor 110 may be a gyroscope that computes angular yaw, pitch, and/or roll (in degrees or radians) of the visor 112 relative to the helmet 118. In another example, the position sensor 110 may be a magnet. A percent may be estimated respecting how open a visor 112 is in relation to the helmet 118 by determining the magnetic field strength or flux perceived by the position sensor 110. "Partially open" visor information can be used to denote that the user may be receiving eye and face protection for hazards while still receiving a reasonable amount of respiratory protection. This "partially open" visor state, if kept to short durations, can assist the user in face to face communications with other workers. Position sensor 111 can be a variety of types of sensors, for example, an accelerometer, gyro, magnet, switch, potentiometer, digital positioning sensor or air pressure sensor. Position sensor 111 can also be a combination of any of the sensors listed above, or any other types of sensors that can be used to detected the position of the visor 112 relative to the helmet 118. Head top 110 may be supported on a user's head by a suspension (not shown).

Head top 110 may include other types of sensors. For example, head top 110 may include temperature sensor 113 that detects the ambient temperature in the interior of head top 110. Head top 110 may include other sensors such as an infrared head detection sensor positioned near the suspension of head top 110 to detect the presence of a head in head top 110, or in other words, to detect whether head top 110 is being worn at any given point in time. Head top 110 may also include other electronic components, such as a communication module, a power source, such as a battery, and a processing component. A communication module may include a variety of communication capabilities, such as radio frequency identification (RFID), Bluetooth, including any generations of Bluetooth, such as Bluetooth low energy (BLE), any type of wireless communication, such as WiFi, Zigbee, radio frequency or other types of communication methods as will be apparent to one of skill in the art up one reading the present disclosure.

Communication module in head top 110 can electronically interface with sensors, such as position sensor 111 or temperature sensor 113, such that it can transmit information from position sensor 111 or temperature sensor 113 to other electronic devices, including communication hub 130. Communications hub 130 illustrates one example of hubs 14 shown in FIG. 2. Communication hub 130 includes a processor, a communication module and a power supply. The communication module of communication hub 130 can include any desired communication capability, such as: RFID, Bluetooth, including any generations of Bluetooth technology, and WiFi communication capabilities. Communication hub 130 can also include any type of wireless communication capabilities, such as radio frequency or Zigbee communication.

Communication hub 130 includes electronics module 132 that has a power source, such as a battery, to provide power to both the processor and communication module. A rechargeable battery, such as a Lithium Ion battery, can provide a compact and long-life source of power. Communication hub 130 may be adapted to have electrical contacts exposed or accessible from the exterior of the hub to allow recharging the communication hub 130.

Communication hub 130 can include a processor that can receive, store and process information. For example, communication module in communication hub 130 may receive information from a communication module in head top 110 or directly from the position sensor 111 indicating the position of visor 112, whether visor 112 is open or closed, and at what time the visor 112 position changed. Any information collected by sensors and transmitted to or from communication hub 130 can be time stamped based on the time of an event that was sensed or detected, based on the time of transmission of information, or both.

One or more processors in communication hub 130 can store this information and compare it with other information received. Other information received may include, for example, information from environmental beacon 140 and information from PPEMS 150. Communication hub 130 can further store rules, such as threshold information both for a length of time visor 112 is allowed to be in an open position before an alert is generated, and the level or type of contaminants that will trigger an alert. For example, when communication hub 130 receives information from environmental beacon 140 that there are no hazards present in the environment, the threshold for the visor 112 being in the open position may be infinite. If a hazard is present in the environment, then the threshold would be determined based upon the concern of the threat to the user. Radiation, dangerous gases, or toxic fumes would all require assignment of the threshold to be on the order of one second or less.

Thresholds for head top temperature can be used to predict heat related illness and more frequent hydration and/or rest periods can be recommended to the user. Thresholds can be used for predicted battery run time. As the battery nears selectable remaining run time, the user can be notified/warned to complete their current task and seek a fresh battery. When a threshold is exceeded for a specific environmental hazard, an urgent alert can be given to the user to evacuate the immediate area. Thresholds can be customized to various levels of openness for the visor. In other words, a threshold for the amount of a time the visor may be open without triggering an alarm may be longer if the visor is in the partially open position as compared to the open position.

A user's individual state of health could be a factor for adjusting the threshold. If a user is in a situation where donning or doffing could take a long time, battery notification threshold could be adjusted to allow for time to don and doff PPE.

Reaching different thresholds may result in triggering different types of alerts or alarms. For example, alarms may be informational (not requiring a user response), urgent (repeated and requiring a response or acknowledgement from a user), or emergency (requiring immediate action from a user.) The type of alert or alarm can be tailored to the environment. Different types of alerts and alarms can be coupled together to get user attention. In some instances, a user may be able to "snooze" an alert or alarm.

Communication hub 130 may include a user interface, such as a display, lights, buttons, keys (such as arrow or other indicator keys), and may be able to provide alerts to the user in a variety of ways, such as by sounding an alarm or vibrating. The user interface can be used for a variety of functions. For example, a user may be able to acknowledge or snooze an alert through the user interface. The user interface may also be used to control settings for the head top and/or turbo peripherals that are not immediately within the reach of the user. For example, the turbo may be worn on the lower back where the wearer cannot access the controls without significant difficulty.

Communication hub 130 can be portable such that it can be carried or worn by a user. Communication hub 130 can also be personal, such that it is used by an individual and communicates with personal protective equipment (PPE) assigned to that individual. In FIG. 3, communication hub 130 is secured to a user using a strap 134. However, communication hub may be carried by a user or secured to a user in other ways, such as being secured to PPE being worn by the user, to other garments being worn to a user, being attached to a belt, band, buckle, clip or other attachment mechanism as will be apparent to one of skill in the art upon reading the present disclosure.

Environmental beacon 140 includes at least environmental sensor 142 which detects the presence of a hazard and communication module 144. Environmental sensor 142 may detect a variety of types of information about the area surrounding environmental beacon 140. For example, environmental sensor 142 may be a thermometer detecting temperature, a barometer detecting pressure, an accelerometer detecting movement or change in position, an air contaminant sensor for detecting potential harmful gases like carbon monoxide, or for detecting air-born contaminants or particulates such as smoke, soot, dust, mold, pesticides, solvents (e.g., isocyanates, ammonia, bleach, etc.), and volatile organic compounds (e.g., acetone, glycol ethers, benzene, methylene chloride, etc.). Environmental sensor 142 may detect, for example any common gasses detected by a four gas sensor, including: CO, O2, HS and Low Exposure Limit. In some instances, environmental sensor 142 may determine the presence of a hazard when a contaminant level exceeds a designated hazard threshold. In some instances, the designated hazard threshold is configurable by the user or operator of the system. In some instances, the designated hazard threshold is stored on at least one of the environmental sensor and the personal communication hub. In some instances, the designated hazard threshold is stored on PPEMS 150 and can be sent to communication hub 130 or environmental beacon 140 and stored locally on communication hub 130 or environmental beacon 140. In some examples, PPEMS 150 may be an example of PPEMS 6 of this disclosure.

Environmental beacon communication module 144 is electronically connected to environmental sensor 142 to receive information from environmental sensor 142. Communication module 144 may include a variety of communication capabilities, such as: RFID, Bluetooth, including any generations of Bluetooth technology, and WiFi communication capabilities. Communication hub 130 can also include any type of wireless communication capabilities, such as radio frequency or Zigbee communication.

In some instances, environmental beacon 140 may store hazard information based on the location of environmental beacon 140. For example, if environmental beacon 140 is in an environment known to have physical hazards, such as the potential of flying objects, environmental beacon 140 may store such information and communicate the presence of a hazard based on the location of environmental beacon 140. In other instances, the signal indicating the presence of a hazard may be generated by environmental beacon 140 based on detection of a hazard by environmental sensor 142.

The system may also have an exposure threshold. An exposure threshold can be stored on any combination of PPEMS 150, communication hub 130, environmental beacon 140, and head top 110. A designated exposure threshold is the time threshold during which a visor 112 can be in the open position before an alert is generated. In other words, if the visor is in the open position for a period of time exceeding a designated exposure threshold, an alert may be generated. The designated exposure threshold may be configurable by a user or operator of the system. The designated exposure threshold may depend on personal factors related to the individual's health, age, or other demographic information, on the type of environment the user is in, and on the danger of the exposure to the hazard.

An alert can be generated in a variety of scenarios and in a variety of ways. For example, the alert may be generated by the communication hub 130 based on information received from head top 110 and environmental sensor 140. An alert may be in the form of an electronic signal transmitted to PPEMS 150 or to any other component of system 100. An alert may comprise one or more of the following types of signals: tactile, vibration, audible, visual, heads-up display or radio frequency signal.

FIG. 4 is a block diagram of electronic components in an exposure indicating filtered air respirator system 200. Filtered air respirator system 200 communicates electronically with environmental beacon 240 and PPEMS 250 using any type of wireless communication mode, such as RFID, Bluetooth, including any generations of Bluetooth technology, and WiFi communication capabilities, radio frequency or Zigbee communication. In some examples, PPEMS 250 may be an example of PPEMS 6 of this disclosure. Environmental beacon 240 and PPEMS 250 may communicate wirelessly or through wired connection.

Filtered air respirator system 200 includes head top 210, communication hub 230 and clean air supply source 220. Head top 210 includes several electronic components, such as position sensor 211, head detection sensor 212, temperature sensor 213, and communication module 214. While these are exemplary electronic components in head top 210, head top 210 may contain additional electronic components such as a processor to receive, store and process information from each of position sensor 211, head detection sensor 212, and temperature sensor 213, along with information received by communication module 214 from other devices. A processor may also control some or all of the sensors and communication module in head top 210. Other types of components, such as a battery or other power source and other types of sensors may also be included in head top 210.

Communication hub 230 communicates electronically with each of head top 210 and clean air supply source 220. Communication hub 230 can include any desired communication capability, such as: RFID, Bluetooth, including any generations of Bluetooth technology, and WiFi communication capabilities. Communication hub 230 can also include any type of wireless communication capabilities, such as radio frequency or Zigbee communication. Communication hub 230 may also communicate electronically with environmental beacon 240 and PPEMS 250.

Clean air supply source 220 includes a motor and fan assembly that provides a pressurized source of air to head top 210. Additionally, clean air supply source includes a processor 224 and a communication module 222. Processor 224 may interface with other components within clean air supply source 220. For example, processor 224 may interface with the battery or power source for clean air supply source 220 to determine how much battery life remains for the particular battery at any given point in time. Processor 224 may also communicate with the motor controlling fan speed, to determine how much air is being forced through the filter in clean air supply source 220, and therefore estimate remaining filter life. Data from the position sensor 211 may also be collected by the processor 224 to determine the measure that a visor is open or closed and/or the frequency that the visor changes status. Head detection sensor 212 and temperature sensor 213 data may also be transmitted to the processor 224 for additional analysis. In one example, if the head detection sensor 212 does not detect a head nor does the temperature sensor 213 indicate a rise in temperature and the position sensor 211 is open, then an alert will not be generated, transmitted, or stored. Processor 224 in clean air supply source 220 may track information such as flow rate, pressure drop across the filter, filter presence/identification on filter, battery run time, blower run time, filter run time, and whether the head top is a loose or tight fitting head top. Communication module 222 is in electrical communication with processor 224. Communication module 222 may include any desired communication capability, such as: RFID, Bluetooth, including any generations of Bluetooth technology, and WiFi communication capabilities. Communication module 222 can also include any type of wireless communication capabilities, such as radio frequency or Zigbee communication. Communication module can communicate wireless with communication hub 230. In some instances, communication module may communicate with other devices, such as environmental beacon 240 and PPEMS 250.

Figure 5:
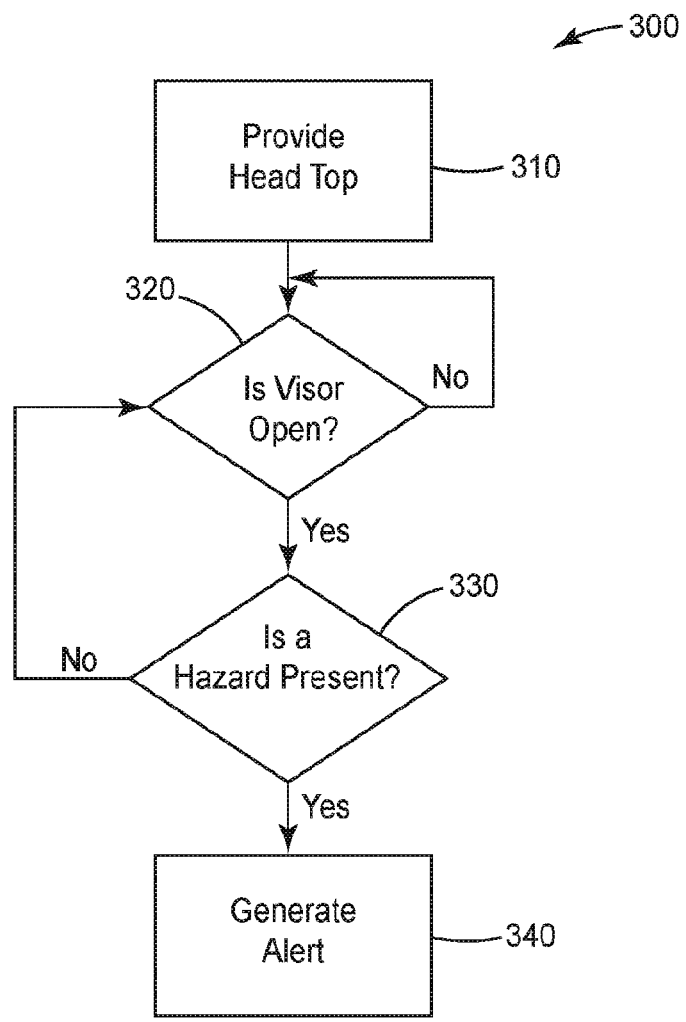
FIG. 5 is a flow chart associated with determining exposure in accordance with various techniques of this disclosure.

FIG. 5 is a flow chart 300 associated with determining exposure, and indicating exposure to a user. While the steps shown in FIG. 5 are exemplary operations associated with the present disclosure, variations on the order of the steps, and additional steps, will be apparent to one of skill in the art upon reading the present disclosure.

Initially, a headtop may be provided to a user (310). A head top can include a visor that is sized to fit over at least user's nose and mouth, a position sensor, and a head top communication module. Various embodiments of head tops are described herein. In some instances, additional pieces of PPE or other devices may be provided, such as a clean air supply source, a personal communication hub, or any other desired component.

A computing device, (e.g., in a data hub, PPE, or remote computing device) may detect if the visor is in an open position (320). The visor position is detected by a position sensor in the head top. If the visor is in a closed position (or is not in an open position), the operation of 320 is repeated. If the visor is in an open position, the computing device then queries whether a hazard is present (330). A hazard may be detected in a variety of ways, as described herein.

If a hazard is not detected, the computing device returns to operation to query whether the visor is open. If a hazard is detected in step 330, an alert is generated (340). A variety of types of alerts may be generated. For example, an alert may comprise one or more of the following types of signals: tactile, vibration, audible, visual, heads-up display or radio frequency signal. In some instances, an alert is not generated unless an exposure threshold and/or a hazard threshold is first met. Other variations of the steps shown are within the scope of the present disclosure. For example, in some instances the presence of the hazard is detected by an environmental sensor. In some instances, the environmental sensor determines the presence of a hazard when a contaminant level exceeds a designated hazard threshold.

In some instances, the alert is generated after the visor has been in an open position for a period of time exceeding a designated exposure threshold. In some instances, the head top further comprises a head detection sensor, and wherein the alert is only generated if the head detection sensor detects that the head top is being worn by the user. In some instances the system also detects if the visor is in a partially open position. In some instances, the head top further comprises a temperature sensor, wherein the temperature sensor detects the temperature in the interior of the head top.

Figure 6:
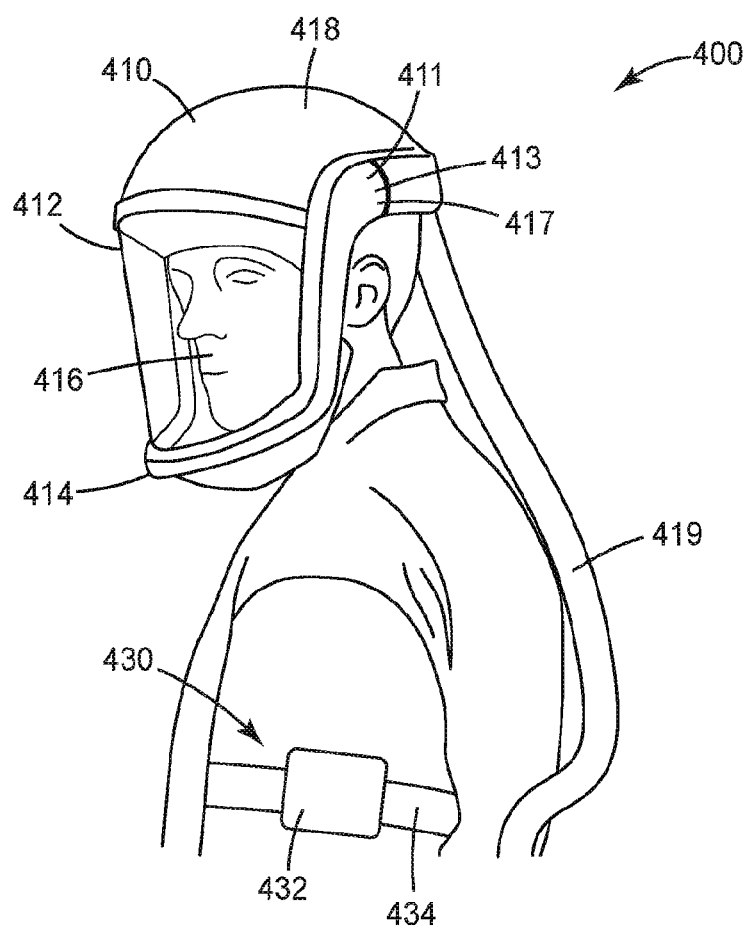
FIG. 6 is an exposure-indicating head top in accordance with various techniques of this disclosure.

FIG. 6 is an exposure-indicating head top system 400 that includes a head top 410 with a visor 412 that is sized to fit over at least a user's nose and mouth. System 400 represents one example of respirators 13 shown in FIG. 2. Visor 412 includes lens 416 which is secured to helmet 418 by the frame assembly 414. Head top also includes a position sensor 411 that senses the position of visor 412 relative to helmet 418 to determine if the visor is in an open position or in a closed position. In some instances, position sensor 411 may detect whether visor 412 is partially open, and if so, what measure (e.g., percent or degree) it is open. As an example, the position sensor 110 may be a gyroscope that computes angular yaw, pitch, and/or roll (in degrees or radians) of the visor 112 relative to the helmet 118. In another example, the position sensor 110 may be a magnet. A percent may be estimated respecting how open a visor 112 is in relation to the helmet 118 by determining the magnetic field strength or flux perceived by the position sensor 110. Position sensor 411 can be a variety of types of sensors, for example, an accelerometer, gyro, magnet, switch or air pressure sensor. Position sensor 411 can also be a combination of any of the sensors listed above, or any other types of sensors that can be used to detected the position of the visor 412 relative to the helmet 418. Head top 410 may be supported on a user's head by a suspension (not shown).

Head top 410 may include other types of sensors. For example, head top 410 may include temperature sensor 413 that detects the ambient temperature in the interior of head top 410. Head top 410 may include other sensors such as an infrared head detection sensor positioned near the suspension of head top 410 to detected the presence of a head in head top 410, or in other words, to detect whether head top 410 is being worn at any given point in time. Head top 410 may also include other electronic components, such as a communication module 417, a power source, such as a battery, and a processing component. A communication module may include a variety of communication capabilities, such as radio frequency identification (RFID), Bluetooth, including any generations of Bluetooth, such as Bluetooth low energy (BLE), any type of wireless communication, such as WiFi, Zigbee, radio frequency or other types of communication methods as will be apparent to one of skill in the art up one reading the present disclosure.

Communication module can electronically interface with sensors, such as position sensor 411 or temperature sensor 413, such that it can transmit information from position sensor 411 or temperature sensor 413 to other electronic devices, including communication hub 430. Communication hub 430 may include a user interface, such as a display, lights, buttons, keys (such as arrow or other indicator keys), and may be able to provide alerts to the user in a variety of ways, such as by sounding an alarm or vibrating. A user can set up WiFi parameters for the hub. The user interface includes, for example, a button, LED's and vibration ability.

Communication hub 430 can be portable such that it can be carried or worn by a user. Communication hub 430 can also be personal, such that it is used by an individual and communicates with personal protective equipment (PPE) assigned to that individual. In FIG. 6, communication hub 430 is secured to a user using a strap 434. However, communication hub may be carried by a user or secured to a user in other ways, such as being secured to PPE being worn by the user, to other garments being worn to a user, being attached to a belt, band, buckle, clip or other attachment mechanism as will be apparent to one of skill in the art upon reading the present disclosure.

Figure 7:
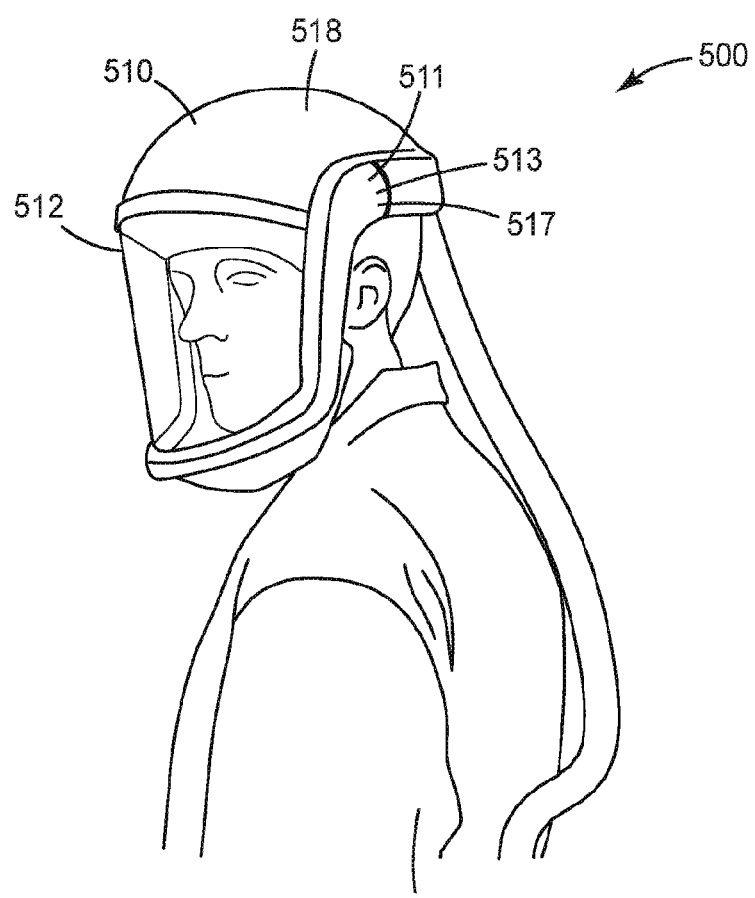
FIG. 7 is an exposure indicating head top and communication hub system in accordance with various techniques of this disclosure.

FIG. 7 is an integrated exposure indicating head top and communication hub system 500. System 500 represents one example of respirators 13 shown in FIG. 2. The system 500 includes a head top 510. Head top 510 includes at least a visor 512 that is sized to fit over at least the user's nose and mouth. Head top 510 further includes a position sensor 511 that detects whether the visor is in a closed position or in an open position. Head top 510 also includes communication module 517. If communication modules 517 receives a signal indicating the presence of a hazard, and if the visor 512 is in an open position, an alert as generated.

Communication module 517 may include a variety of communication capabilities, such as radio frequency identification (RFID), Bluetooth, including any generations of Bluetooth, such as Bluetooth low energy (BLE), any type of wireless communication, such as WiFi, Zigbee, radio frequency or other types of communication methods as will be apparent to one of skill in the art up one reading the present disclosure. Communication module 517 may receive a signal indicating the presence of a hazard from a variety of other devices, such as an environmental beacon, a database or another communication device, such as a communication hub as described herein.

Figure 8:
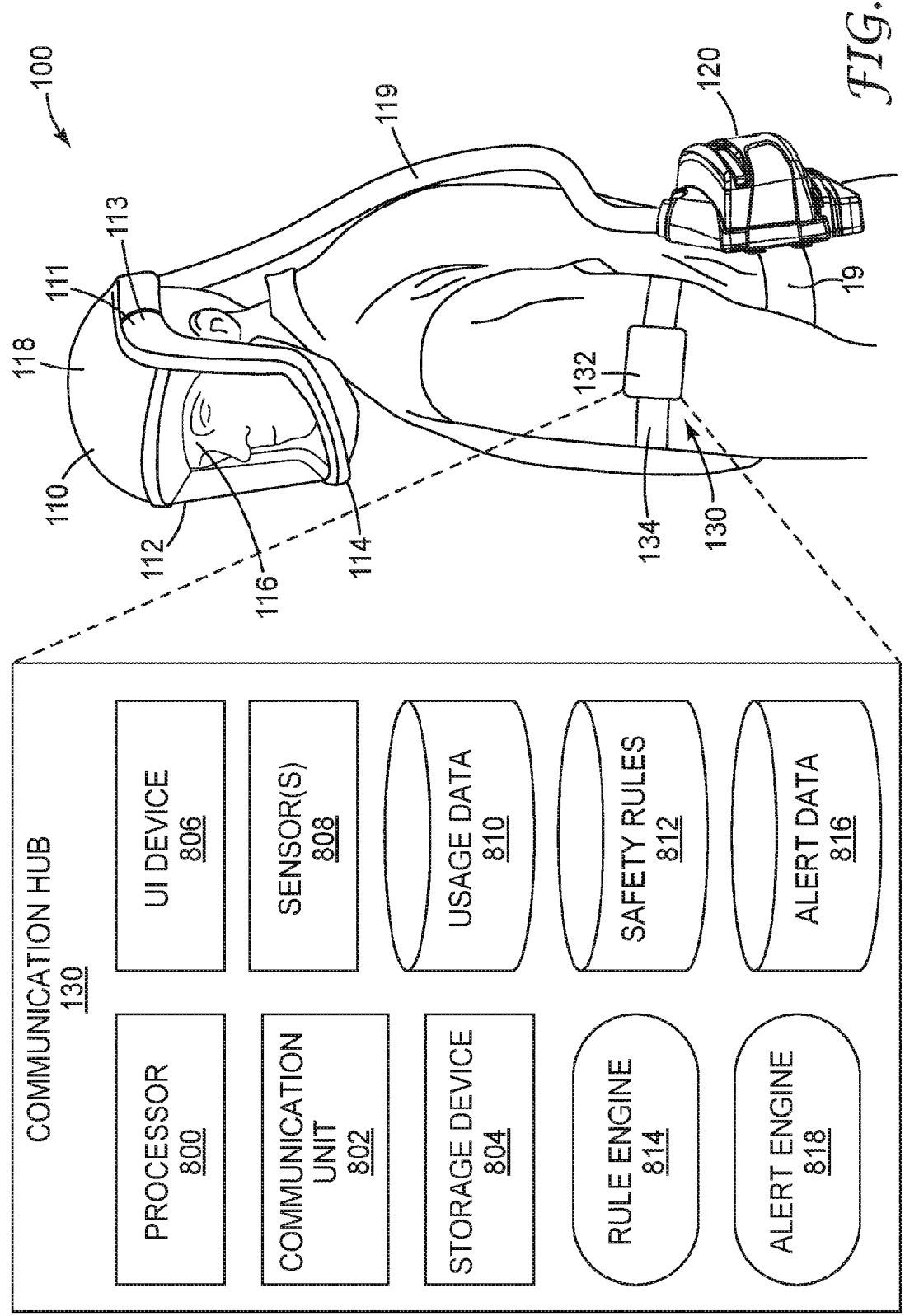
FIG. 8 is a conceptual diagram illustrating an example of self-retracting line (SRL) in communication with a wearable data hub, in accordance with various aspects of this disclosure.

FIG. 8 illustrates an exposure-indicating filtered air respirator system, in accordance with this disclosure. A head top 110 of a 3M™ Versaflo™ Heavy Industry PAPR Kit TR-300-HIK obtained from 3M™ Company of St. Paul, MN was modified to include a position sensor 111 between the visor 112 and helmet 118. The position sensor 110 was a LIS3MDL magnetometer obtained from ST Microelectronics. A communication hub 130 as described herein was wirelessly connected via Bluetooth to a processor within the head top that monitored the position sensor 111. A beacon 140 (Kontakt.io Smart Beach Two) obtained from Kontakt.io was programmed with a geographical location using global positioning system (GPS) coordinates and a radiation hazardous environmental condition. The visor 112 of the head top 110 was initially closed. The communication hub 130 wirelessly contacted the beacon 140 and determined that the head top was located in hazardous environment based upon the GPS location and radiation hazard status. The visor 112 was then opened and an alert was generated and was indicated with flashing light emitting diodes (LEDS) on the communication hub 130.

FIG. 8 illustrates components of communication hub 130 including processor 800, communication unit 802, storage device 804, user-interface (UI) device 806, sensors 808, usage data 810, safety rules 812, rule engine 814, alert data 816, and alert engine 818. As noted above, communication hub 130 represents one example of hubs 14 shown in FIG. 2. FIG. 8 illustrates only one particular example of communication hub 130, as shown in FIG. 8. Many other examples of communication hub 130 may be used in other instances and may include a subset of the components included in example communication hub 130 or may include additional components not shown example communication hub 130 in FIG. 8.

In some examples, communication hub 130 may be an intrinsically safe computing device, smartphone, wrist- or head-wearable computing device, or any other computing device that may include a set, subset, or superset of functionality or components as shown in communication hub 130. Communication channels may interconnect each of the components in communication hub 130 for inter-component communications (physically, communicatively, and/or operatively). In some examples, communication channels may include a hardware bus, a network connection, one or more inter-process communication data structures, or any other components for communicating data between hardware and/or software.

Communication hub 130 may also include a power source, such as a battery, to provide power to components shown in communication hub 130. A rechargeable battery, such as a Lithium Ion battery, can provide a compact and long-life source of power. Communication hub 130 may be adapted to have electrical contacts exposed or accessible from the exterior of the hub to allow recharging the communication hub 130. As noted above, communication hub 130 may be portable such that it can be carried or worn by a user. Communication hub 130 can also be personal, such that it is used by an individual and communicates with personal protective equipment (PPE) assigned to that individual. In FIG. 8, communication hub 130 is secured to a user using a strap 134. However, communication hub may be carried by a user or secured to a user in other ways, such as being secured to PPE being worn by the user, to other garments being worn to a user, being attached to a belt, band, buckle, clip or other attachment mechanism as will be apparent to one of skill in the art upon reading the present disclosure.

One or more processors 800 may implement functionality and/or execute instructions within communication hub 130. For example, processor 800 may receive and execute instructions stored by storage device 804. These instructions executed by processor 800 may cause communication hub 130 to store and/or modify information, within storage devices 804 during program execution. Processors 800 may execute instructions of components, such as rule engine 814 and alert engine 818 to perform one or more operations in accordance with techniques of this disclosure. That is, rule engine 814 and alert engine 818 may be operable by processor 800 to perform various functions described herein.

One or more communication units 802 of communication hub 130 may communicate with external devices by transmitting and/or receiving data. For example, communication hub 130 may use communication units 802 to transmit and/or receive radio signals on a radio network such as a cellular radio network. In some examples, communication units 802 may transmit and/or receive satellite signals on a satellite network such as a Global Positioning System (GPS) network. Examples of communication units 802 include a network interface card (e.g. such as an Ethernet card), an optical transceiver, a radio frequency transceiver, a GPS receiver, or any other type of device that can send and/or receive information. Other examples of communication units 802 may include Bluetooth®, GPS, 3G, 4G, and Wi-Fi® radios found in mobile devices as well as Universal Serial Bus (USB) controllers and the like.

One or more storage devices 804 within communication hub 130 may store information for processing during operation of communication hub 130. In some examples, storage device 804 is a temporary memory, meaning that a primary purpose of storage device 804 is not long-term storage. Storage device 804 may be configured for short-term storage of information as volatile memory and therefore not retain stored contents if deactivated. Examples of volatile memories include random access memories (RAM), dynamic random access memories (DRAM), static random access memories (SRAM), and other forms of volatile memories known in the art.

Storage device 804 may, in some examples, also include one or more computer-readable storage media. Storage device 804 may be configured to store larger amounts of information than volatile memory. Storage device 804 may further be configured for long-term storage of information as non-volatile memory space and retain information after activate/off cycles. Examples of non-volatile memories include magnetic hard discs, optical discs, floppy discs, flash memories, or forms of electrically programmable memories (EPROM) or electrically erasable and programmable (EEPROM) memories. Storage device 804 may store program instructions and/or data associated with components such as rule engine 814 and alert engine 818.

UI device 806 may be configured to receive user input and/or output information to a user. One or more input components of UI device 806 may receive input. Examples of input are tactile, audio, kinetic, and optical input, to name only a few examples. UI device 806 of communication hub 130, in one example, include a mouse, keyboard, voice responsive system, video camera, buttons, control pad, microphone or any other type of device for detecting input from a human or machine. In some examples, UI device 806 may be a presence-sensitive input component, which may include a presence-sensitive screen, touch-sensitive screen, etc.

One or more output components of UI device 806 may generate output. Examples of output are data, tactile, audio, and video output. Output components of UI device 806, in some examples, include a presence-sensitive screen, sound card, video graphics adapter card, speaker, cathode ray tube (CRT) monitor, liquid crystal display (LCD), or any other type of device for generating output to a human or machine. Output components may include display components such as cathode ray tube (CRT) monitor, liquid crystal display (LCD), Light-Emitting Diode (LED) or any other type of device for generating tactile, audio, and/or visual output. Output components may be integrated with communication hub 130 in some examples.

UI device 806 may include a display, lights, buttons, keys (such as arrow or other indicator keys), and may be able to provide alerts to the user in a variety of ways, such as by sounding an alarm or vibrating. The user interface can be used for a variety of functions. For example, a user may be able to acknowledge or snooze an alert through the user interface. The user interface may also be used to control settings for the head top and/or turbo peripherals that are not immediately within the reach of the user. For example, the turbo may be worn on the lower back where the wearer cannot access the controls without significant difficulty.

Sensors 808 may include one or more sensors that generate data indicative of an activity of a worker 10 associated with hub 14 and/or data indicative of an environment in which hub 14 is located. Sensors 808 may include, as examples, one or more accelerometers, one or more sensors to detect conditions present in a particular environment (e.g., sensors for measuring temperature, humidity, particulate content, noise levels, air quality, or any variety of other characteristics of environments in which respirator 13 may be used), or a variety of other sensors.

Communication hub 130 may store usage data 810 from components of air respirator system 100. For example, as described herein, components of air respirator system 100 (or any other examples of respirators 13) may generate data regarding operation of system 100 that is indicative of activities of worker 10 and transmit the data in real-time or near real-time to hub 130. Usage data may include, for example, the data shown in Tables 1-3.

In some examples, hub 130 may immediately relay usage data 810 to another computing device, such as PPEMS 6, via communication unit 802. In other examples, storage device 804 may store usage data 810 for some time prior to uploading the data to another device. For example, in some instances, communication unit 802 may be able to communicate with system 100 but may not have network connectivity, e.g., due to an environment in which system 100 is located and/or network outages. In such instances, hub 130 may store usage data 810 to storage device 804, which may allow the usage data to be uploaded to another device upon a network connection becoming available.

Communication hub 130 may store safety rules 812 as described in this disclosure. Safety rules 812 may be stored in any suitable data store as described in this disclosure. Safety rules 812 may, in some examples, include the rules set forth in the example of Table 4 above.

As examples for purposes of illustration, safety rules 812 may include threshold information both for a length of time visor 112 is allowed to be in an open position before an alert is generated, and the level or type of contaminants that will trigger an alert. For example, when data hub 130 receives information from an environmental beacon that there are no hazards present in the environment, the threshold for the visor 112 being in the open position may be infinite. If a hazard is present in the environment, then the threshold may be determined based upon the concern of the threat to the user. Radiation, dangerous gases, or toxic fumes would all require assignment of the threshold to be on the order of one second or less.

Thresholds for head top temperature can be used to predict, e.g., by PPEMS 6, heat related illness and more frequent hydration and/or rest periods can be recommended to the user. Thresholds can be used for predicted battery run time. As the battery nears selectable remaining run time, the user can be notified/warned to complete their current task and seek a fresh battery. When a threshold is exceeded for a specific environmental hazard, an urgent alert can be given to the user to evacuate the immediate area. Thresholds can be customized to various levels of openness for the visor. In other words, a threshold for the amount of a time the visor may be open without triggering an alarm may be longer if the visor is in the partially open position as compared to the open position.

Reaching different thresholds set forth in safety rules 812 may result in triggering different types of alerts or alarms. For example, alarms may be informational (not requiring a user response), urgent (repeated and requiring a response or acknowledgement from a user), or emergency (requiring immediate action from a user.) The type of alert or alarm can be tailored to the environment. Different types of alerts and alarms can be coupled together to get user attention. In some instances, a user may be able to "snooze" an alert or alarm.

Rule engine 814 may be a combination of hardware and software that executes one or more safety rules, such as safety rules 812. For instance, rule engine 814 may determine which safety rules to execute based on context data, information included in the safety rule set, other information received from PPEMS 6 or other computing devices, user input from the worker, or any other source of data that indicates which safety rules to execute. In some examples, safety rules 812 may be installed prior to a worker entering a work environment, while in other examples, safety rules 812 be dynamically retrieved by communication hub 130 based on context data generated at first particular point in time.

Rule engine 814 may execute safety rules periodically, continuously, or asynchronously. For instance, rule engine 814 may execute safety rules periodically by evaluating the conditions of such rules each time a particular time interval passes or expires (e.g., every second, every minute, etc.). In some examples, rule engine 814 may execute safety rules continuously by checking such conditions using one or more scheduling techniques that continuously evaluate the conditions of such rules. In some examples, rule engine 814 may execute safety rules asynchronously, such as in response to detecting an event. An event may be any detectable occurrence, such as moving to a new location, detecting a worker, coming within a threshold distance of another object, or any other detectable occurrence.

Rule engine 814, upon determining that a condition of a safety rule has or has not been satisfied may perform one or more actions associated with the safety rule by executing one or more operations that define the actions. For instance, rule engine 814 may execute a condition that determines if a worker is approaching or has entered a work environment, (a) whether a PAPR is being worn by the worker and (b) whether the filter in the PAPR of a particular type of filter, e.g., a filter that removes contaminants of a particular type. This safety rule may specify actions if the condition is not satisfied which cause rule engine 814 to generate an alert at communication hub 130 using UI device 806 and send a message using communication unit 802 to PPEMS 6, which may cause PPEMS 6 to send a notification to a remote user (e.g., the safety manager).

Alert data 816 may be used for generating alerts for output by UI device 806. For example, hub 130 may receive alert data from PPEMS 6, end-user computing devices 16, remote users using computing devices 18, safety stations 15, or other computing devices. In some examples, alert data 816 may be based on operation of system 100. For example, hub 130 may receive alert data 816 that indicates a status of system 100, that system 100 is appropriate for the environment in which system 100 is located, that the environment in which system 100 is located is unsafe, or the like.

In some examples, additionally or alternatively, hub 130 may receive alert data 816 associated with a likelihood of a safety event. For example, as noted above, PPEMS 6 may, in some examples, apply historical data and models to usage data from system 100 in order to compute assertions, such as anomalies or predicted occurrences of imminent safety events based on environmental conditions or behavior patterns of a worker using system 100. That is, PPEMS 6 may apply analytics to identify relationships or correlations between sensed data from system 100, environmental conditions of environment in which system 100 is located, a geographic region in which system 100 is located, and/or other factors. PPEMS 6 may determine, based on the data acquired across populations of workers 10, which particular activities, possibly within certain environment or geographic region, lead to, or are predicted to lead to, unusually high occurrences of safety events. Hub 130 may receive alert data 816 from PPEMS 6 that indicates a relatively high likelihood of a safety event.

Alert engine 818 may be a combination of hardware and software that interprets alert data 816 and generate an output at UI device 806 (e.g., an audible, visual, or tactile output) to notify worker 10 of the alert condition (e.g., that the likelihood of a safety event is relatively high, that the environment is dangerous, that system 100 is malfunctioning, that one or more components of system 100 need to be repaired or replaced, or the like). In some instances, alert engine 818 may also interpret alert data 816 and issue one or more commands to system 100 to modify operation or enforce rules of system 100 in order to bring operation of system 100 into compliance with desired/less risky behavior. For example, alert engine 818 may issue commands that control the operation of head top 110 or clean air supply source 120 (e.g., to increase the speed of the blower, or the like).

FIGS. 9-16 illustrate example user interfaces (UIs) for representing usage data from one or more respirators, according to aspects of this disclosure. For example, as described herein, respirators 13 may be configured to transmit acquired usage data to PPEMS 6. Computing devices, such as computing devices 60 may request PPEMS 6 to perform a database query or otherwise generate and output a report or user interface to present acquired safety information, compliance information and any results of the analytic engine, e.g., by the way of dashboards, alert notifications, reports and the like. That is, as described herein, users 24, 26, or software executing on computing devices 16, 18, (FIG. 1) may submit queries or other communication to PPEMS 6 and receive data corresponding to the queries for presentation in the form of one or more reports or dashboards. The UIs shown in FIGS. 9-16 represent examples of such reports or dashboards, and may be output, for example, at any of computing devices 60 (FIG. 2).

The UIs shown in FIGS. 9-16 may provide various insights regarding system 2, such as baseline ("normal") operation across worker populations, identifications of any anomalous workers engaging in abnormal activities that may potentially expose the worker to risks, identifications of any geographic regions within environments 2 for which unusually anomalous (e.g., high) safety events have been or are predicted to occur, identifications of any of environments 8 exhibiting anomalous occurrences of safety events relative to other environments, and the like. In some examples, PPEMS 6 may automatically reconfigure a user interface in response to detecting a safety event. For instance, PPEMS 6 may determine one or more characteristics of the safety event relating to PPE, worker, and/or worker environment associated with the event and update one or more user interfaces that include input controls customized to the particular safety event. For instance, specific details relating to the characteristics of the safety event such as PPE type, work environment location, and/or worker metrics may be presented in a user interface in response to the safety event to enable one or more persons to respond efficiently to the safety event with the relevant information.

Figure 9:
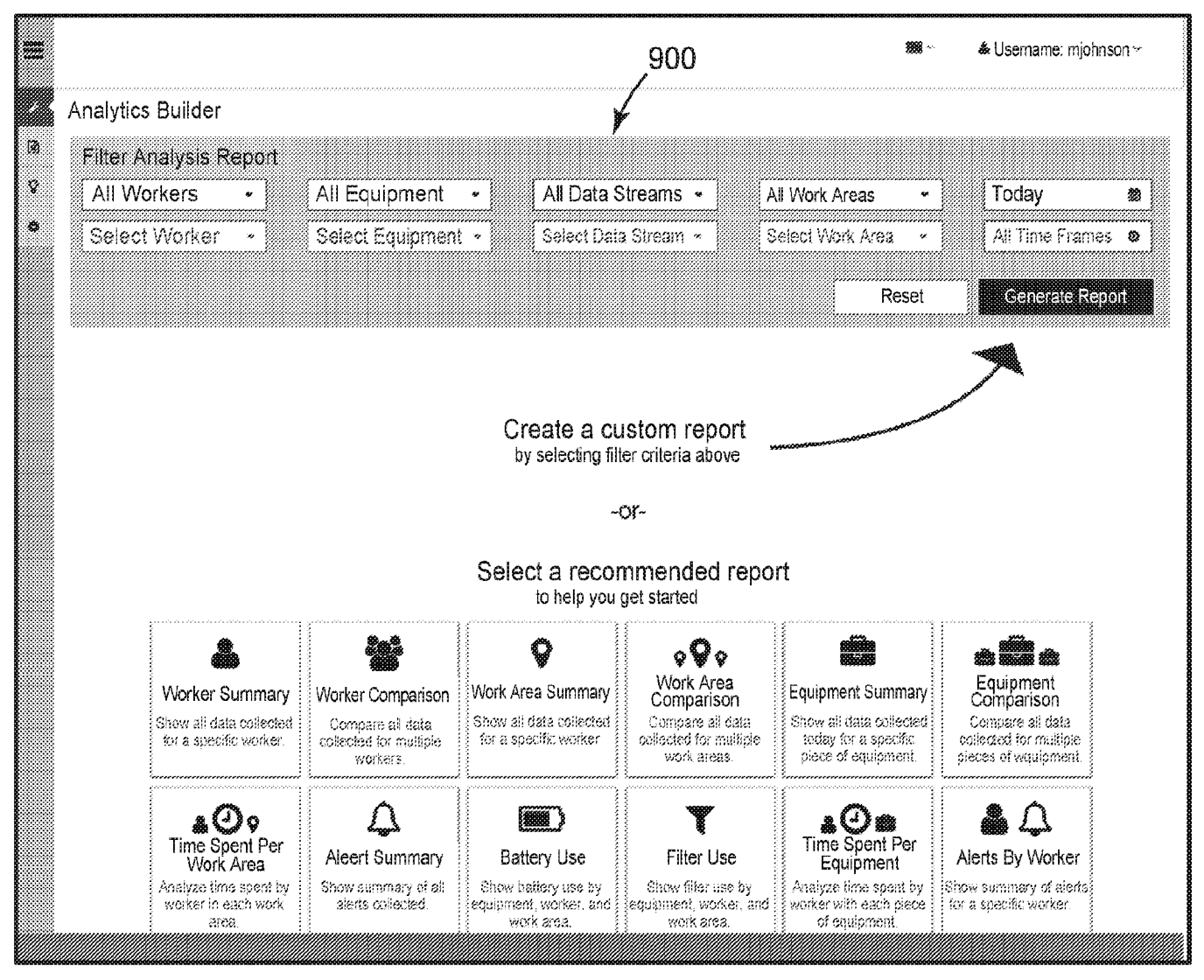

FIG. 9 illustrates a UI having a plurality of user-selectable filters 900 for filtering usage data from at least one respirator, such as at least one of respirators 13. Computing devices 60 may output UI content based on the filter selections, the UI content being indicative of the usage data corresponding to the filter selections, as shown in greater detail with respect to FIG. 10.

Figure 10:
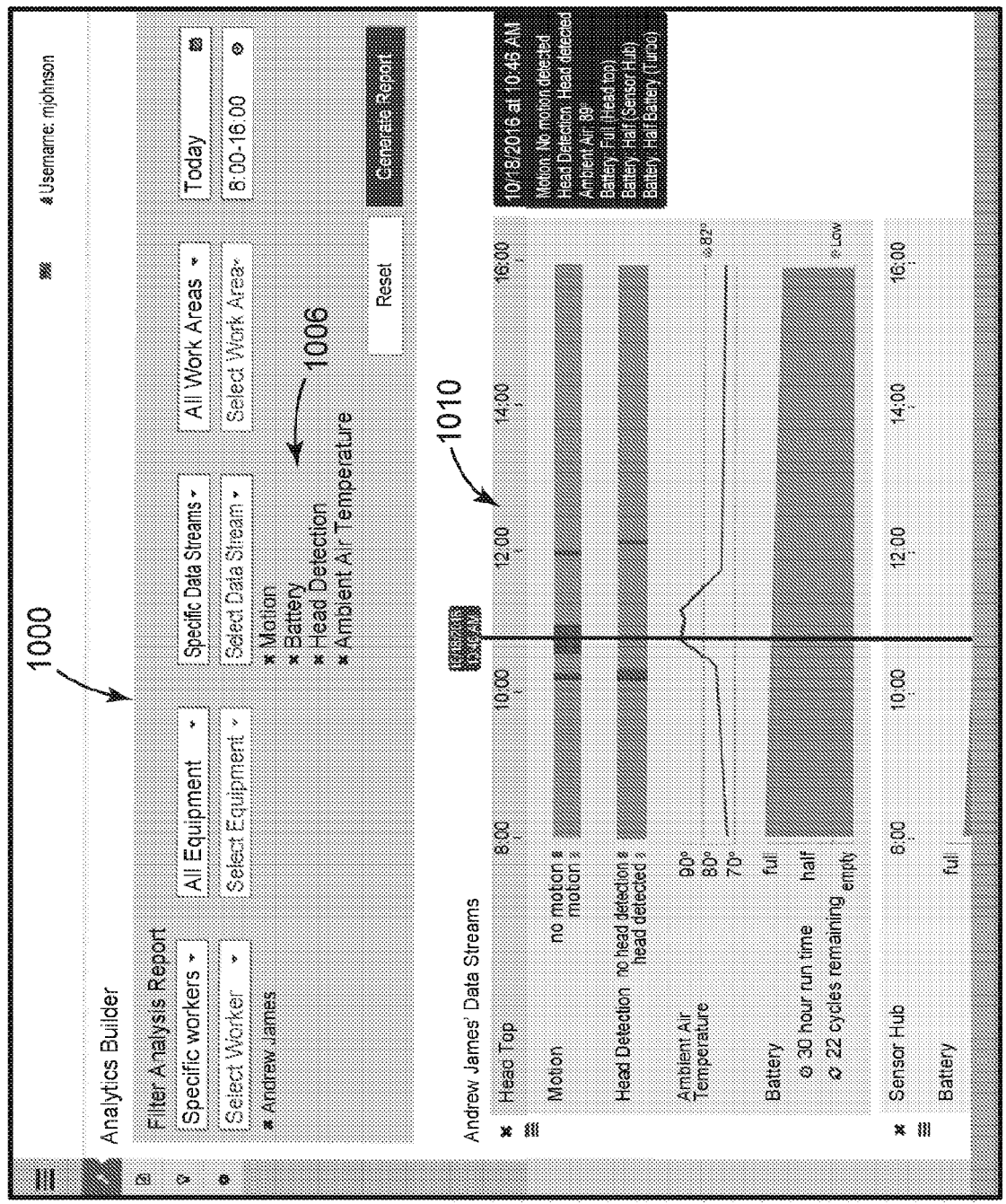

FIG. 10 illustrates another example of a UI having a plurality of user-selectable filters 1000 for filtering usage data from at least one respirator, such as at least one of respirators 13. Again, computing devices 60 may output UI content based on the filter selections 1006 that is indicative of the usage data corresponding to the filter selections. In the example of FIG. 10, filter selections include motion of a user of respirator 13, a battery status of respirator 13, head presence of a user's head in respirator 13, and ambient air temperature.

The UI content of FIG. 10 also includes a plurality of usage data streams over a time domain 1010, where the usage data streams correspond to the filter selections. With respect to motion, for example, the corresponding data stream indicates when the user was in motion or not in motion. In addition, the UI includes content regarding head detection, ambient air temperature, and battery status over a time domain.

Figure 11:
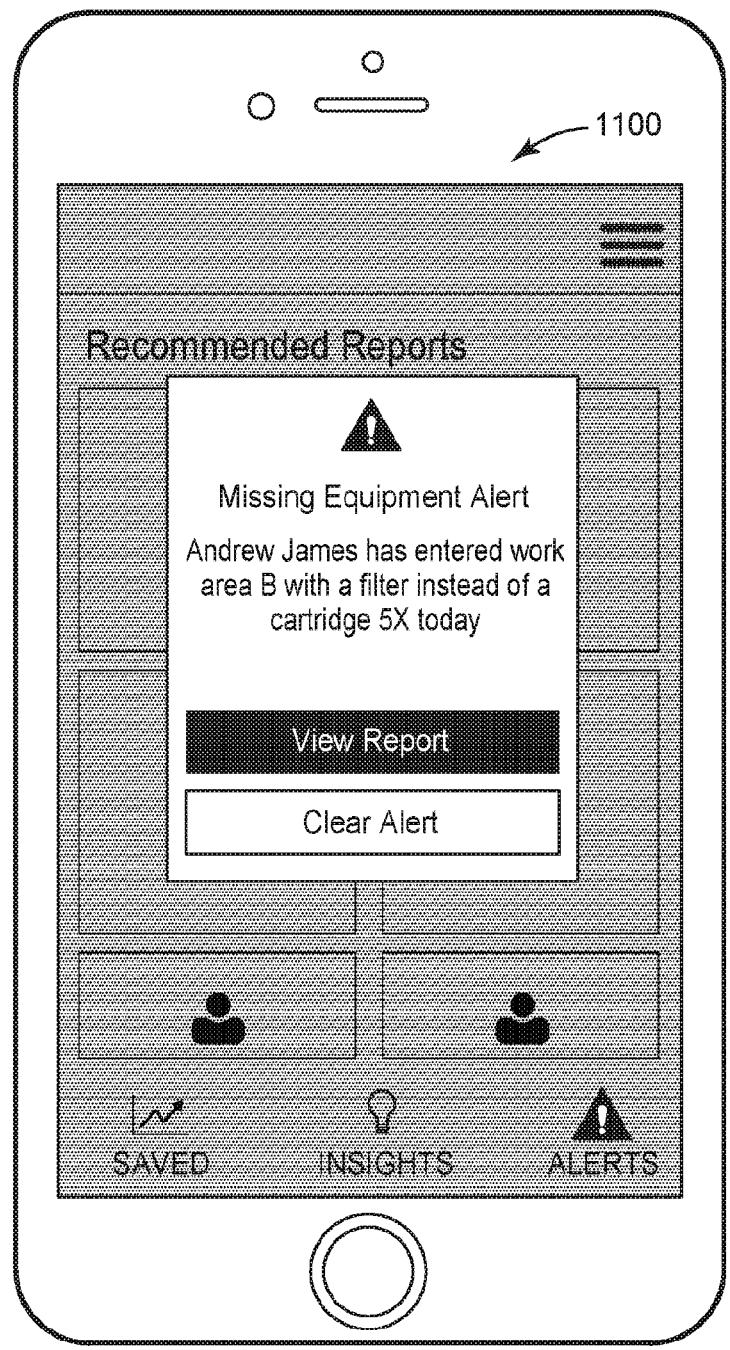

FIG. 11 illustrates one example of an alert 1100, which may be issued by PPEMS 6. For example, PPEMS 6 may generate alert data that indicates that a user of a respirator 13 does not have the proper equipment (e.g., an incorrect filter for a particular environment). PPEMS 6 may transmit the alert data to one of computing devices 60, which may generate the UI shown in FIG. 11 based on the alert data.

Figure 12:
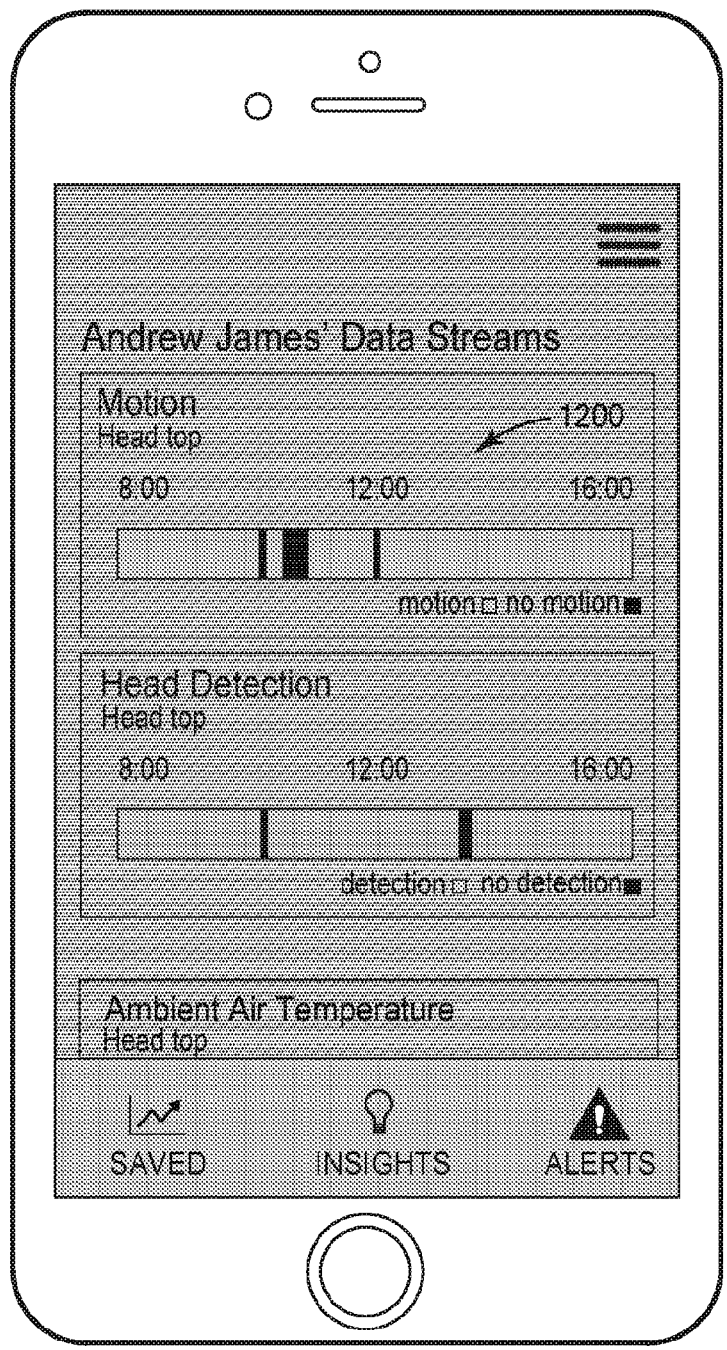

FIG. 12 illustrates another example of a UI that includes a plurality of usage data streams over a time domain 1200. In some examples, the usage data streams correspond to the filter selections. The example of FIG. 12 illustrates a UI that has been generated based on the form factor of the computing device upon which UI is generated and displayed. In particular, the UI has been generated for a form factor associated with a mobile computing device.

Figure 13:
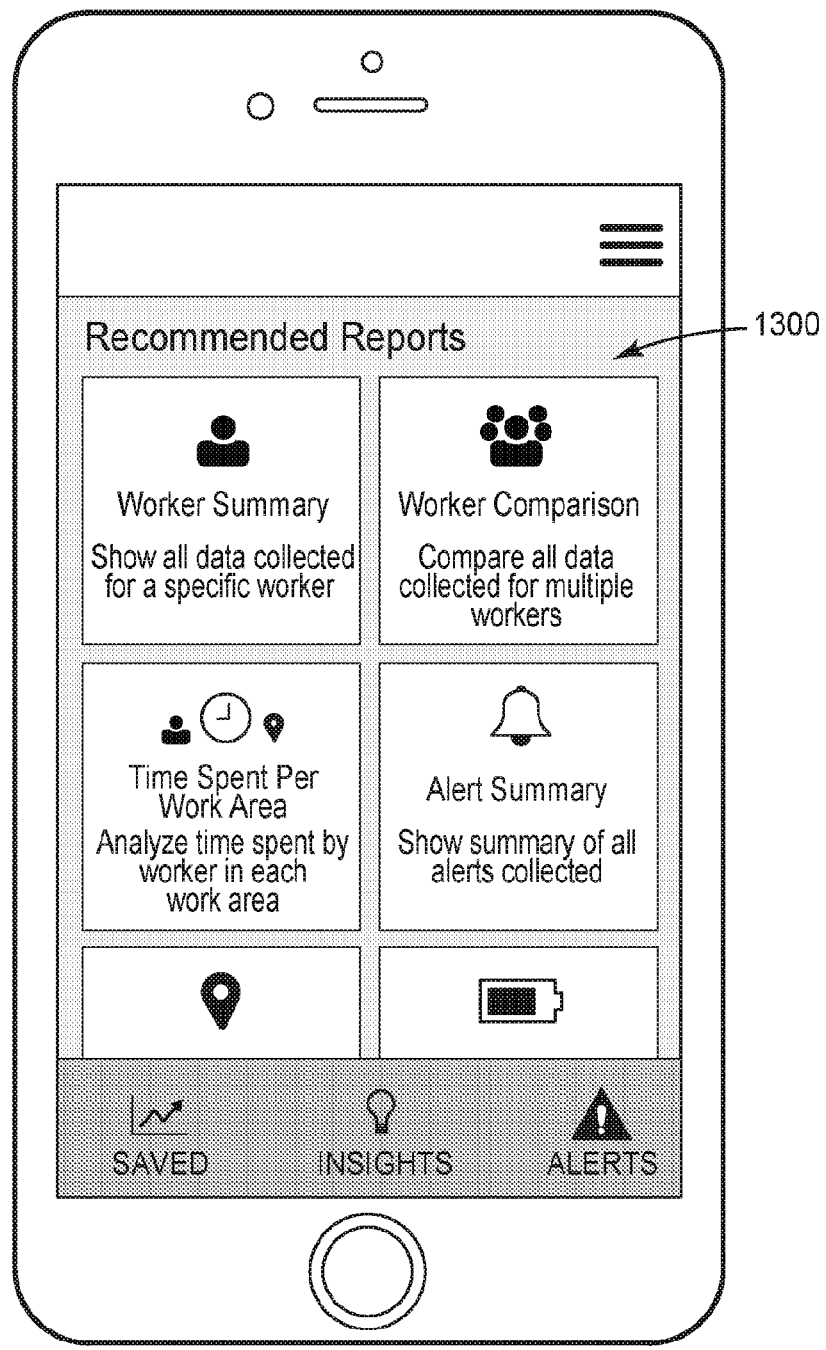

FIG. 13 illustrates a UI that includes a plurality of recommended reports 1300. In some examples, PPEMS 6 may populate recommended reports based on, for example, reports previously run for a particular user (e.g., safety manager), reports run for other users (e.g., other safety managers) that deploy the same or similar PPE, the type of PPE deployed in a particular environment, or the like.

Figure 14:
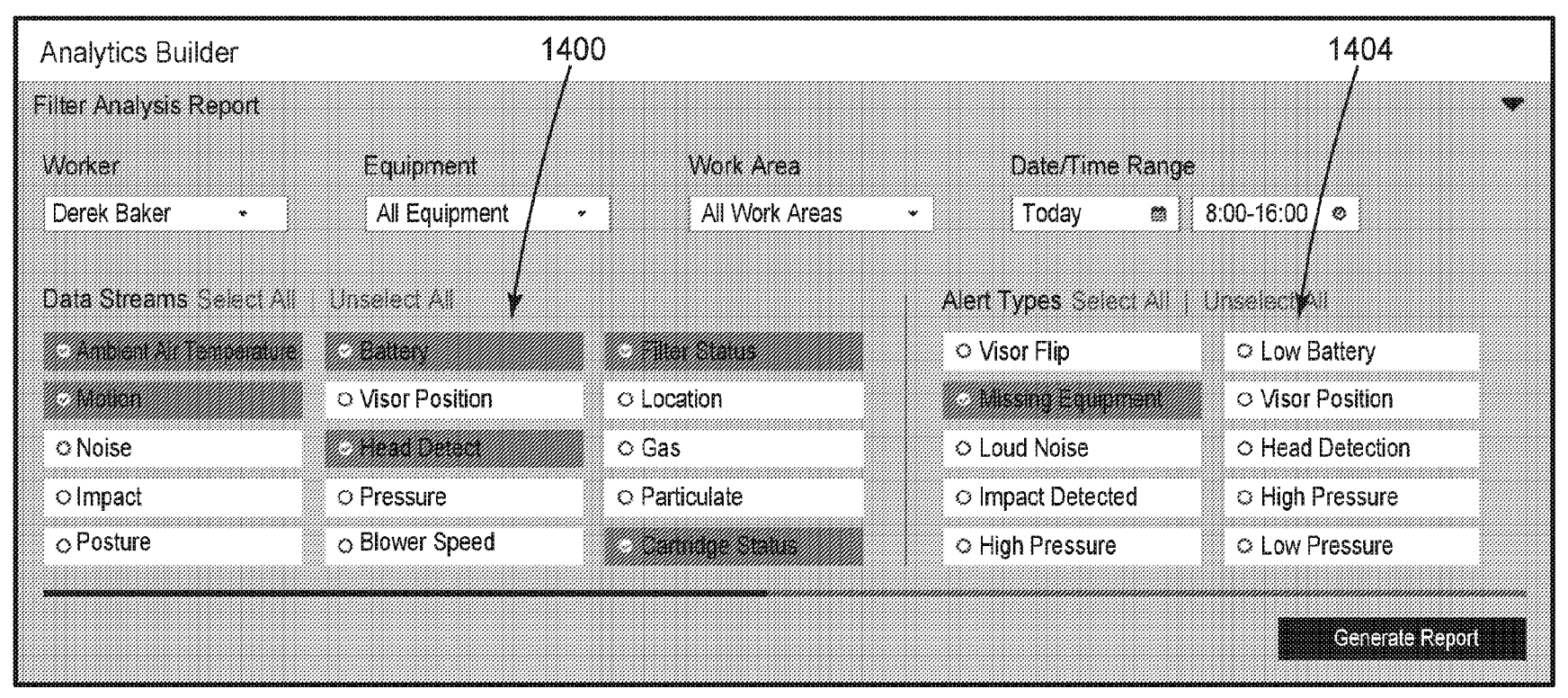

FIG. 14 illustrates another example of a UI having a plurality of user-selectable filters 1400 for filtering usage data from at least one respirator, such as at least one of respirators 13. Again, computing devices 60 may output UI content based on the filter selections that is indicative of the usage data corresponding to the filter selections. In the example of FIG. 10, filter selections include ambient air temperature, motion of a user of respirator 13, a battery status of respirator 13, head presence of a user's head in respirator 13, a filter status of a filter of respirator 13, and a cartridge status of a cartridge of respirator 13.

As shown in the example of FIG. 14, a non-limiting set of filters may include, as examples, identification of a user of a respirator of the at least one respirator, components of the at least one respirator, a geographic location, a time, a temperature, a motion of the user, an ambient noise, an impact to the at least one respirator, a posture of the user of the at least one respirator, a battery status of a battery of the at least one respirator, a visor position of a visor of the at least one respirator, a presence of a head in a head top of the at least one respirator, a pressure of a blower of the at least one respirator, a blower speed of the blower of the at least one respirator, a filter status of a filter of the at least one respirator, or a status of a cartridge of the at least one respirator.

The example of FIG. 14 also includes alert filters 1404 for filtering alert types from the at least one respirator. A user may select particular alters from alert filters 1404, and a computing device may output UI content based on the alert filter selections. In the example of FIG. 14, missing equipment alerts has been selected, which may result in generation of the UI content shown in FIG. 11.

Figure 15:
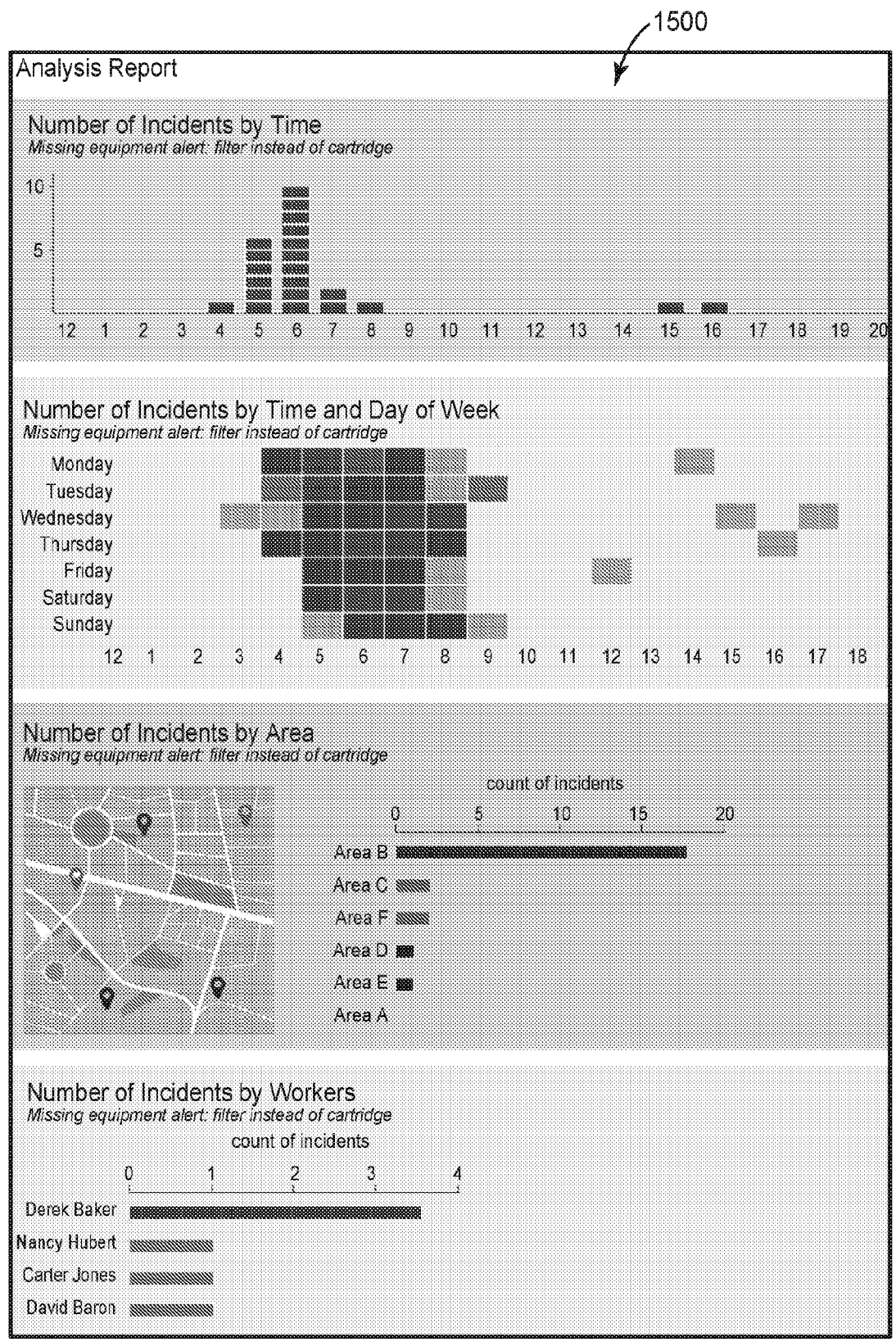

FIG. 15 illustrates example UI content in the form of a report that includes a number of incidents by time, a number of incidents by time and day of the week, a number of incidents by area, and a number of incidents by particular workers. The incidents illustrated in FIG. 15 may correspond to usage data from respirators and/or alerts generated based on the usage data. For example, the UI of FIG. 15 illustrates incidents associated with a missing equipment alert.

Figure 16:
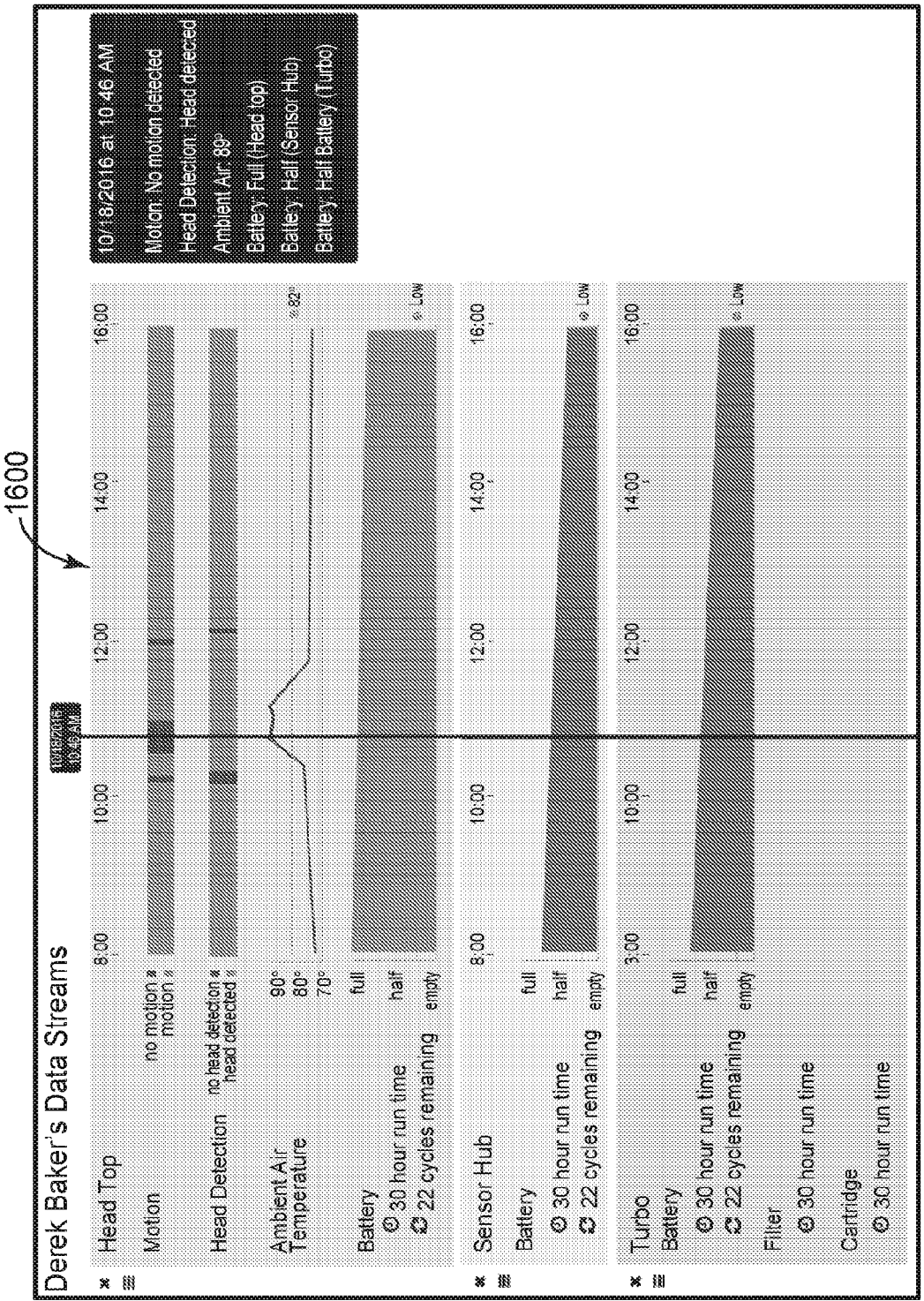

FIG. 16 illustrates another example of UI content that includes a plurality of usage data streams over a time domain 1600, where the usage data streams may correspond to filter selections. In the example of FIG. 16, an anomaly at 10:46 AM is identified for ambient air temperature using the vertical line and date description output for display in the user interface.

Figure 17:
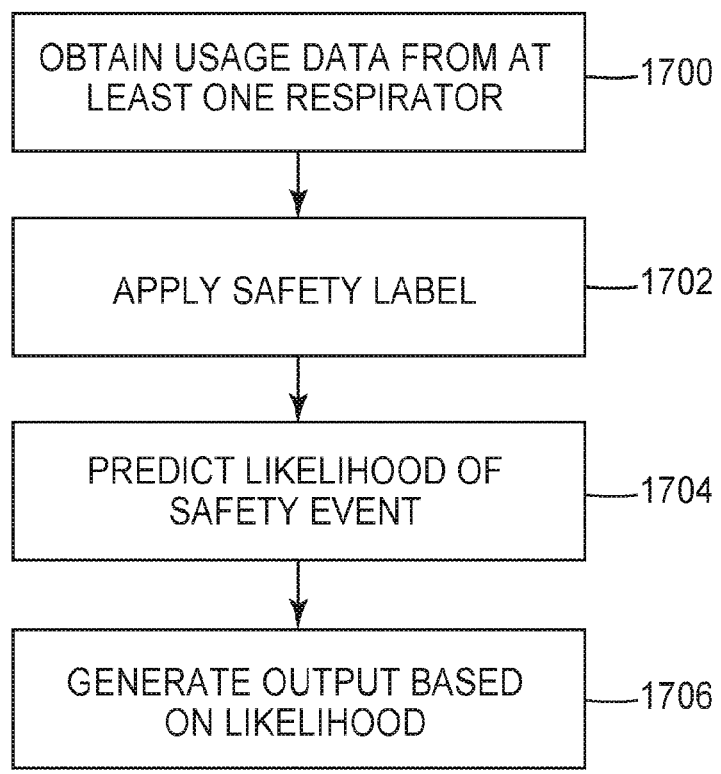
FIG. 17 is a flow diagram illustrating an example process for determining the likelihood of a safety event, according to aspects of this disclosure.

FIG. 17 is a flow diagram illustrating an example process for determining the likelihood of a safety event, according to aspects of this disclosure. While the techniques shown in FIG. 17 are described with respect to PPEMS 6, it should be understood that the techniques may be performed by a variety of computing devices.

In the illustrated example, PPEMS 6 obtains usage data from at least one respirator, such as at least one of respirators 13 (1700). As described herein, the usage data comprises data indicative of operation of respirator 13. In some examples, PPEMS 6 may obtain the usage data by polling respirators 13 or hubs 14 for the usage data. In other examples, respirators 13 or hubs 14 may send usage data to PPEMS 6. For example, PPEMS 6 may receive the usage data from respirators 13 or hubs 14 in real time as the usage data is generated. In other examples, PPEMS 6 may receive stored usage data.

PPEMS 6 may apply the usage data to a safety learning model that characterizes activity of a user of the at least one respirator 13 (1702). For example, as described herein, the safety learning model may be trained based on data from known safety events and/or historical data from respirators 13. In this way, the safety learning model may be arranged to define safe regions and regions unsafe.

PPEMS 6 may predict a likelihood of an occurrence of a safety event associated with the at least one respirator 13 based on application of the usage data to the safety learning model (1704). For example, PPEMS 6 may apply the obtained usage data to the safety learning model to determine whether the usage data is consistent with safe activity (e.g., as defined by the model) or potentially unsafe activity.

PPEMS 6 may generate an output in response to predicting the likelihood of the occurrence of the safety event (1706). For example, PPEMS 6 may generate alert data when the usage data is not consistent with safe activity (as defined by the safety learning model). PPEMS 6 may send the alert data to respirator 13, a safety manager, or another third party that indicates the likelihood of the occurrence of the safety event.

Figure 18:
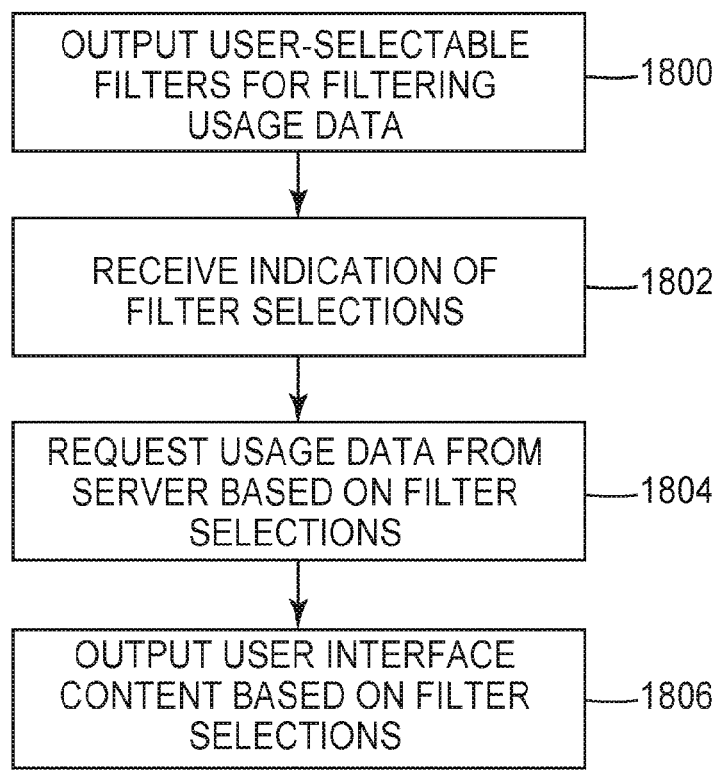
FIG. 18 is a flow chart of a process for generating a user interface (UI) that includes content based on usage data from one or more respirators.

FIG. 18 is a flow chart of a process for generating a user interface (UI) that includes content based on usage data from one or more respirators. The techniques shown in FIG. 18 may be used to generate the example UIs shown in FIGS. 9-16. While the techniques shown in FIG. 18 are described with respect to a computing device 60, it should be understood that the techniques may be performed by a variety of computing devices.

Computing device 60 outputs, for display by computing device 60, a UI having a plurality of user-selectable filters for filtering usage data from at least one respirator (such as at least one of respirators 13) (1800). The filters may include, as non-limiting examples, identification of a user of a respirator of the at least one respirator, components of the at least one respirator, a geographic location, a time, a temperature, a motion of the user, an ambient noise, an impact to the at least one respirator, a posture of the user of the at least one respirator, a battery status of a battery of the at least one respirator, a visor position of a visor of the at least one respirator, a presence of a head in a head top of the at least one respirator, a pressure of a blower of the at least one respirator, a blower speed of the blower of the at least one respirator, a filter status of a filter of the at least one respirator, or a status of a cartridge of the at least one respirator.

Computing device 60 may receive, by the computing device, an indication of filter selections for the user-selectable filters, e.g., by a user of computing device 60 (1802). Computing device 60 may request the usage data from one or more servers (such as PPEMS 6) based on the filter selections (1804). Computing device 60 may then output, for display by computing device 60, UI content based on the filter selections, the UI content being indicative of the usage data corresponding to the filter selections (1806). For example, in some instances, computing device 60 may generate one or more data streams of usage data over a time domain, as shown in the various examples of FIGS. 9-16.

Figure 19A:
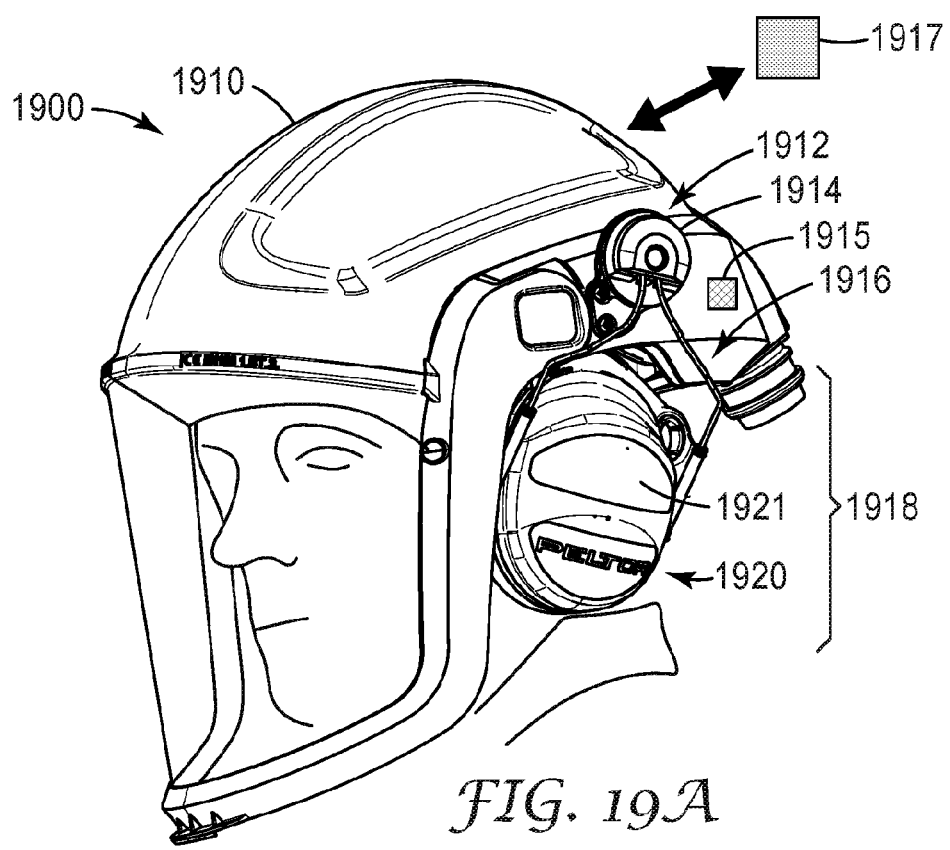
FIGS. 19A-19B illustrate a system that includes a head top and hearing protector, in accordance with this disclosure.
Figure 19B:
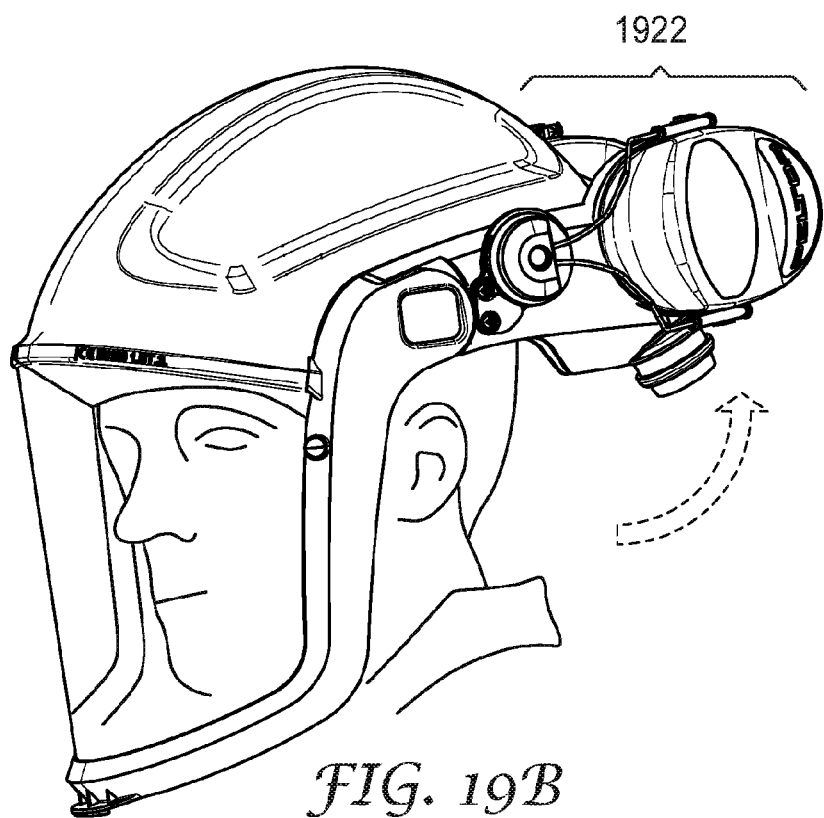

FIGS. 19A-19B illustrate a system 1900 that includes head top 1910 and hearing protector 1920, in accordance with this disclosure. As shown in FIG. 19A, head top 1910 may include structure and functionality that is similar to or the same as head top 110 as described in FIG. 8 and other embodiments of this disclosures. Head top 1910 (or other headworn device, such as a head band) may include hearing protector 1920 that includes, ear muff attachment assembly 1912. Ear muff attachment assembly 1912 may include housing 1914, an arm set 1916, and ear muffs 1921. Hearing protector 1920 may include two separate ear muff cups 1921, one of which is visible in FIGS. 19A-19B and the other on the opposite side of the user's head and similarly configured to the visible ear muff cup in FIG. 19A. Arm set 1916 is rotatable between one or more different positions, such that hearing protector 1920 may be adjusted and/or toggled, for example, between "active" and "standby" positions (or one or more additional intermediate positions), as shown respectively in FIGS. 19A and 19B. In an active position, hearing protector 1920 is configured to at least partially cover a user's ear. In a standby mode, hearing protector 1920 is in a raised position away from and/or out of contact with a user's head. A user is able to switch between active and standby positions when entering or leaving an area necessitating hearing protection, for example, or as may be desired by the user. Adjustment to a standby position allows hearing protector 1920 to be readily available for the user to move hearing protector 1920 into an active position in which hearing protection is provided without the need to carry or store ear muffs.

Ear muff attachment assembly 1912 may be attached directly or indirectly to a helmet, hard hat, strap, head band, or other head support, such as a head top 1910. Head top 1910 may be worn simultaneously with, and provide a support for, ear muff attachment assembly 1912. Ear muff attachment assembly 1912 is attached to an outer surface of head top 1910, and arm set 1916 extends generally downwardly around an edge of head top 1910 such that ear muffs of hearing protector 1920 may be desirably positioned to cover a user's ear.

In various examples, head top 1910 and ear muff attachment assembly 1912 may be joined using various suitable attachment components, such as snap-fit components, rivets, mechanical fasteners, adhesive, or other suitable attachment components as known in the art. Ear muffs of hearing protector 1920 are configured to cover at least a portion of a user's ear and/or head. In FIG. 19A, ear muffs exhibit a cup shape and include a cushion and a sound absorber (not shown). Cushions are configured to contact a user's head and/or ear when ear muffs are in an active position forming an appropriate seal to prevent sound waves from entering. Arm set 1916 extends outwardly from head top 1910 and is configured to carry ear muffs of hearing protector 1920.

In the example of FIGS. 19A-19B, ear muff attachment assembly 1912 may have positional or motion sensors to detect whether the ear muffs are in the standby or active position. The positional or motion sensor may generate one or more signals that indicate a particular position from a set of one or more positions. The signals may indicate one or more position values (e.g., discrete "active"/"standby" values, numeric position representations, or any other suitable encoding or measurement values). If, for example, the standby condition (illustrated in FIG. 19B) is detected by the one or more positional or motion sensors and if an environmental sound detector (either included at system 1900 or in a device external to system 1900) detects unsafe sound levels, then a computing device (included at system 1900 or external to system 1900) may generate an indication of output, such as a notification, log entry, or other type of output. In FIG. 19B, standby position 1922 is illustrated in contrast to active position 1918 of FIG. 19A. In some examples, the indication of output may be audible, visual, haptic, or any other physical sensory output.

In high noise environment workers may be required to use hearing protection in the form of ear plugs or ear muffs. Ear muffs typically comprise cup shaped shell with a sound absorbing liner that seals against the ear of the user. Many workers also use head and/or face protection while wearing ear muffs. Therefore, many ear muff models are designed to attach to a helmet, hard hat or other headgear, such as shown in FIGS. 19A-19B. The ear muffs may be affixed to the headgear via an arm that attaches to the headgear and is adjustable between various positions over or away from the worker's ear.

As described above, headgear mounted ear muffs rotate between two positions: the active position where the ear muffs cover the worker's ears providing hearing protection, and the standby position where the ear muffs are rotated up and away from the ears. While in the standby position the ear muff does not provide hearing protection to the worker. In some types of headgear attached ear muffs, the muffs can be pivoted outward away from the ear of the user in the standby position. In this case, the ear muffs rest at a small distance away from the head of the user. In the active position, the muffs are pivoted toward the head where it is sealed around the ears of the user providing hearing protection.

Techniques and apparatuses of this disclosure may notify workers (or persons nearby or supervising the worker) when the noise level in the work environment exceeds an exposure threshold and when the ear muffs are not engaged in the active position so the worker can ensure his headgear mounted ear muffs are in the active position. Techniques and apparatuses of this disclosure may generate indications of output, such as a notification for a worker within a certain area when the noise level exceeds a predetermined level in that area and when the ear muffs worn by the worker are in the standby position.

Techniques and apparatuses of this disclosure may incorporate engagement or rotation sensors at the headgear mounted ear muffs that determine whether the ear muffs are in the standby position in a location where hearing hazard is present. In some examples, indications of the ear muff or hearing protector being in standby mode while worker is within a certain area where noise levels exceed an exposure threshold may be transmitted by a computing device generating the indication to one or more other computing devices as described in this disclosure.

In some examples, a microphone may be fitted or otherwise positioned inside the cup of the muff to generate an indication or signal from the microphone that is representative of the noise level inside the muff (e.g., decibel level). In some examples, this inner-muff noise level is compared by a computing device to a sound level detected by a microphone outside of the muff, e.g., in the environment of the worker. If a computing device determines the external-muff noise level in the work environment exceeds an exposure threshold and if the computing device determines the difference between the inner-muff sound level measured by the microphone in the muff and the external-muff noise level of the environmental sound sensor is less than the required minimum (indicating proper worker hearing protection), then the computing device may generate an indication of output (e.g., message, alert, or the like) that is sent to one or more other computing devices to notify other workers, supervisors, or persons. In some examples, information collected from the sensors (e.g., position, noise level, and the like) can be used to track compliance and develop worker safety plans in a work environment.

In the example of FIGS. 19A and 19B, housing 1914 may include a position sensor or a gyroscope positioned near the axis of rotation to act as periphery sensor communicating the position of the muff to a computing device. In other examples, housing 1914 may include any suitable device for determining the position of ear muffs 1921. Housing 1914 may include a wired and/or wireless communication device that is communicatively coupled to the sensor or gyroscope. As such, the position sensor or gyroscope may communicate, via the communication device and to the computing device, the present position of ear muffs 1921 and/or a change in position of ear muffs 1921. In some instances, the computing device may be included within housing 1914, may be positioned on or attached to the worker in a separate device external to hearing protector 1920, or may be in a remote computing device separate from the worker altogether (e.g., a remove server).

As shown in FIG. 19A, and in accordance with this disclosure, a system 1900 may include: a hearing protector 1920, at least one position sensor (included in housing 1914) that operates as a position sensor described in this disclosure, at least one sound monitoring sensor 1915. Sound monitoring sensor 1915 may be communicatively coupled to a computing device 1917 which, may be positioned on or attached to the worker in a separate device external to hearing protector 1920 or may be in a remote computing device separate from the worker altogether (e.g., a remove server). Computing device 1917 may include the same, a subset, or a superset of functionality and components illustrated and described in FIGS. 2 and 8. Sound monitoring sensor 1915 may measure and generate data that includes sound levels at points in time, an amount of sound exposure over a period of time, or any other data indicating sound proximate to hearing protector 1920.

In the example of FIGS. 19A-19B, computing device 1917 may be communicatively coupled to the at least one position sensor in housing 1914 and the at least one sound monitoring sensor 1915, computing device 1917 including one or more computer processors and a memory with instructions that when executed by the one or more computer processors cause the one or more computer processors to receive, from the at least one sound monitoring sensor and over a time duration, indications of sound levels to which a worker is exposed. In some examples, the time duration may be user-defined, hard-coded, or machine-generated. Examples of the time duration may be one second, five seconds, thirty seconds, one minute, five minutes, ten minutes, or any time duration. In some examples, the time duration may be pre-defined or pre-determined.

As shown in standby position 1922, computing device 1917 may determine, from the at least one position sensor and during the time duration, that the hearing protector 1920 is not positioned at one or more ears of the worker to attenuate the sound levels (e.g., standby position). Computing device 1917 may determine in other examples, that hearing protector 1920 is positioned at one or more ears of the worker to attenuate sound levels as shown in active position 1918 of FIG. 19A. The at least one position sensor may generate and/or send data to computing device 1917 that indicates the current position of ear muffs 1920 or a change in position. In some examples, hearing protector 1920 may be a set of ear plugs that are included within the worker's ear in active mode, or not included in the worker's ears in standby mode. Rather than using a position sensor, other techniques such as vision-based detection (e.g., using cameras), radio frequency detection (e.g., using radio frequency identification), or any other techniques may be used to determine whether the ear plugs are in active or standby mode and techniques in FIGS. 19A-19B may be similarly used.

Computing device 1917 may generate, in response to the determination that at least one of the sound levels satisfies an exposure threshold during the time duration and the hearing protector is not positioned at one or more ears of the worker to attenuate the sound levels, an indication for output. In some examples, the exposure threshold may be user-defined, hard-coded, or machine-generated. In some examples, the exposure threshold may be defined based at least in part on a health regulation or health data that indicates the maximum amount of sound dosing or sound levels that a worker may be safety exposed to. In some examples, the sound levels may satisfy the exposure threshold if the sound levels are greater than or equal to the exposure threshold for or at a time during the particular time duration.

Computing device 1917 may generate any type of indication of output. In some examples, the indication of output may be a message that includes various notification data. Notification data may include but is not limited to: an alert, warning, or information message; a type of personal protective equipment; a worker identifier; a timestamp of when the message was generated; a position of the personal protective equipment; one or more sound levels or sound dosing, or any other descriptive information. In some examples, the message may be sent to one or more computing devices as described in this disclosure and output for display at one or more user interfaces of output devices communicatively coupled to the respective computing devices. In some examples, the indication of output may be haptic or audible and output at one or more computing devices as described in this disclosure.

In other examples, two microphones may be used as periphery sensors. For instance, a first microphone may be positioned within the ear muff cup and the other microphone may be positioned external to the ear muff cup. This embodiment may be used for hearing protector models where the ear muffs do not rotate as they move between the active and standby positions, but instead pivot away from the head in a lateral direction. This embodiment also works with the ear muffs shown in FIGS. 19A-19B. In this embodiment a small microphone (such as the microphone used in the 3M™ E-A-R Fit™ Validation System) is placed inside the cup of the muff. A second microphone is placed outside of the cup near the first microphone, in some instances, on the side of the headgear. The two microphones communicate to a computing device where the difference in the measured signals representing sound levels between the two microphones is determined by the computing device. The sound level in the work environment may also be received by the computing device from sound meter.

When the noise level in the work environment is below a work environment noise threshold (e.g., below 85 dB), then the computing device may generate for output an indication that is provided to the worker that he/she can place the earmuffs in the standby position. When the noise level in the work environment is above the work environment noise threshold, then the computing device may determine if the difference in sound levels between the internal and external microphones is below a difference threshold indicating that the ear muffs are in the standby position. If the difference in sound level is below the difference threshold, the computing device may generate for output an indication to the worker to place the ear muffs in the active position. In some examples, the indications for output in any of the examples of FIGS. 19A-19B may be sent to, logged, or stored at any number of computing devices.

If the computing device determines that the sound level is above a work environment noise threshold (e.g., an unsafe level) and the difference in the sound levels measured by the periphery microphones is above the difference threshold (indicating that the ear muffs are in the active mode), then no indication for output may be generated. In other examples, the computing device may generate for output an indication that includes a "compliant" status to one or more computing devices.

In some examples, the computing device may determine a location of the worker. The computing device, as part of determining that at least one of the sound levels satisfies the exposure threshold during the time duration and the hearing protector is not positioned at one or more ears of the worker to attenuate the sound levels, may further determine that the location of the worker is within a distance threshold of a location that corresponds to the at least one of the sound levels that satisfies the exposure threshold. That is the computing device may computer the worker's location to a location of a sound level that exceeded an exposure threshold, and determine based on the worker's proximity to the sound level that the hearing protector should be in the active position.

In some examples, techniques of this disclosure may determine a type of hearing protector. For example, a hearing protector may be assigned a protection factor of High, so even if the hearing protector is not positioned exactly correct on a worker, it may provide adequate protection in contrast to a hearing protector with a low protection factor. Hearing protectors may also have accessories or attributes that might make them exhibit higher or lower hearing protection factors, i.e. gel ear seals vs foam.

Figure 20A:
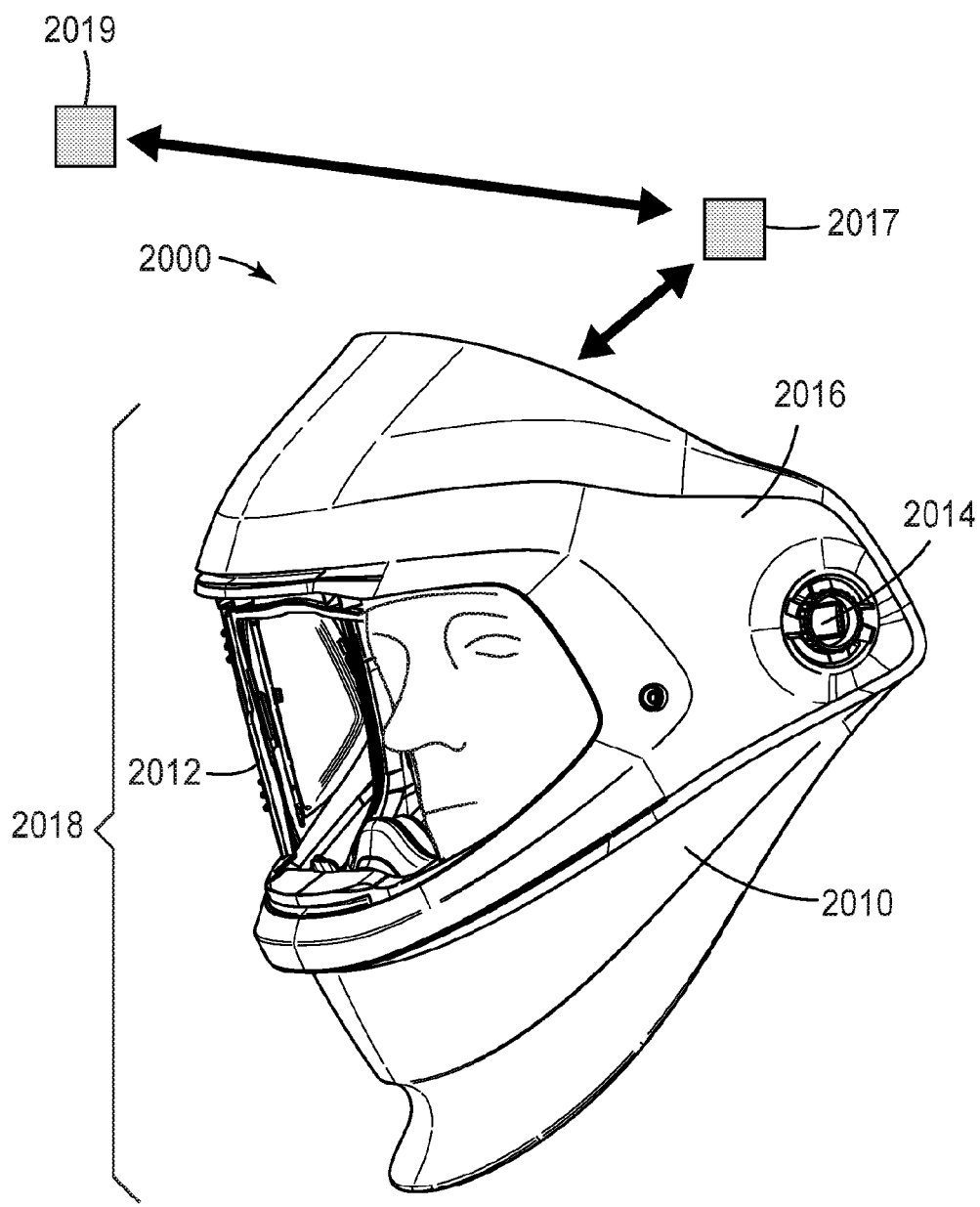
FIGS. 20A-20B illustrate a system that includes a headtop and a visor in accordance with this disclosure.
Figure 20B:
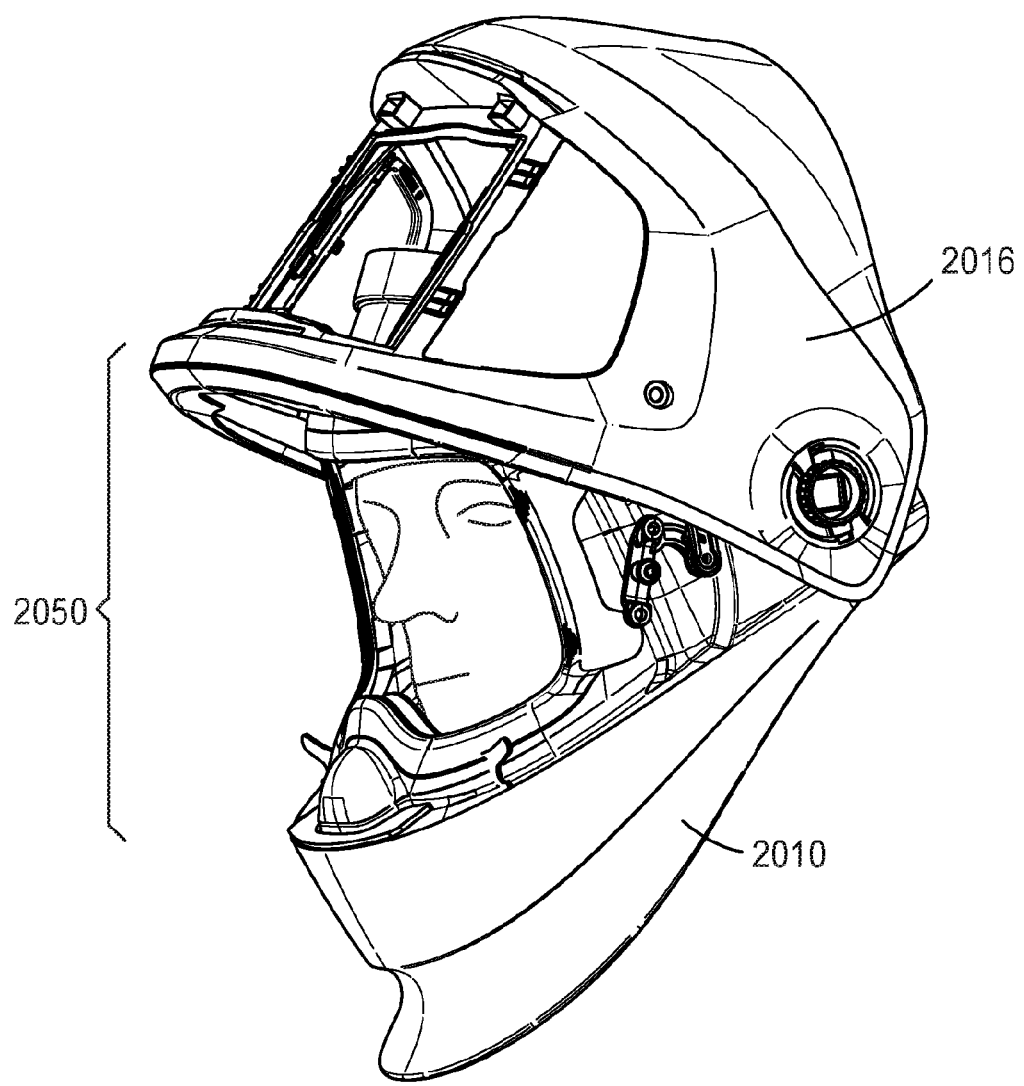

FIGS. 20A-20B illustrate a system 2000 in accordance with this disclosure. System 2000 may include a headtop 2010 and a visor 2016. In some examples, visor 2016 is physically coupled to headtop 2010 by a visor attachment assembly 2014. Visor attachment assembly 2014 may be attached directly or indirectly to a helmet, hard hat, strap, head band, or other head support, such as a head top 2010. Head top 2010 may be worn simultaneously with, and provide a support for, visor attachment assembly 2014. Visor attachment assembly 2014 may be integrated with or attached to an outer surface of head top 2010. Visor 2016 may rotate between one or more open and closed (e.g., active in FIG. 20A and standby in FIG. 20B) positions, such as further shown in FIG. 20B, by pivoting on an axis provided by visor attachment assembly 2014 that is orthogonal to the adjacent surface of visor 2016. In some instances, computing device 2017 may be included at system 2000, may be positioned on or attached to the worker in a separate device external to system 2000, or may be in a remote computing device separate from the worker altogether (e.g., a remove server). In various examples, head top 2010 and visor attachment assembly 2014 may be joined using various suitable attachment components, such as snap-fit components, rivets, mechanical fasteners, adhesive, or other suitable attachment components as known in the art. Visor 2016 is configured to cover at least a portion of a user's face.

As shown in FIG. 20, visor 2016 includes a light-filtering shield 2012, which may filter light to which the user's face would otherwise be exposed. Light-filtering shield 2012 may be any transparent or semi-transparent physical barrier. In some examples, light-filtering shield 2012 may block high intensity light. In this context, "light" means electromagnetic radiation of a wavelength that might be capable of damaging the eyes of a user, or of causing perceived discomfort to the user. In this context, such light includes at least visible light, and may also include infrared and/or ultraviolet radiation, whether or not such radiation is perceptible to the user. In this context, "high intensity" light means light that is present at such intensity (e.g. such as that emitted by a device such as an arc welder) such that it might be capable of damaging the eyes of a user, or of causing perceived discomfort to the user. In some examples, light-filtering shield 2012 may be comprised of well-known electrochromatic materials or chromatic materials that block or otherwise filter high intensity light, and which are within the knowledge of one of ordinary skill in the art.

In some examples, it may be beneficial to notify one or more other workers in proximity to a high-intensity light, who may not be controlling or directly engaged with the activity that is generating the high-intensity light. For instance, multiple workers may be operating within a work environment in which one of the workers is engaged in a welding activity that generates high-intensity light. Other workers with an unobstructed path to the high-intensity light may be exposed to such light which may cause harm to the workers if such light is not filtered. Techniques and systems of this disclosure may prevent such inadvertent exposure to high-intensity light as further described in the example of FIGS. 20A-20B.

FIG. 20A illustrates a system 2000 comprising head-mounted device 2010, visor attachment assembly 2014 that includes at least one position sensor coupled to the head-mounted device 2010, at least one visor 2016 that includes light-filtering shield coupled to the at least one position sensor; at least one light detector 2019; and at least one computing device 2017 communicatively coupled to the at least one position sensor and at least one light detector 2019. Light detector 2019 is capable of detecting at least: "high" input that indicates the presence of high light intensity, "low" input that indicates the absence of high light intensity, a change from high to low input, and a change from low to high input. Light detector 2019 is also capable of communicating the detection of such high and low input and changes there between to the other components of system 2000. As such, when expressions are used in this disclosure such as detects high input, detects low input, detects a change from high input to low input, etc., it will be understood that such detection is by way of light detector 2019.

In some examples, light detector 2019 may detect different types of light where different types refer to different wavelengths. An example of a type of light may be laser light. In some examples, light detector 2019 may determine a type of light rather than an intensity of light. In other examples light detector 2019 may determine a type and an intensity of light.

In various embodiments, light detector 2019 may be located physically close to some or all of the other components (hardware, etc.) of system 2000 or may be located physically remote from some or all of the other components. Regardless, light detector 2019 may be in communication with other components of system 2000 via one or more wired or wireless communication channels as needed for functioning of system 2000. In one embodiment, light detector 2019 is capable of directly detecting incident light of high intensity (e.g., light detector 2019 comprises a photosensitive device, including but not limited to a photodiode, phototransistor, and so on). In this instance, "high input" means that light detector 2019 is directly sensing incident light of high intensity. (In such an embodiment, it may be preferential to locate light detector 2019 in close proximity to system 2000, so that the light incident on light detector 2019 is closely representative of the light incident on system 2000).

In an alternative embodiment, light detector 2019 is capable of detecting the high light intensity indirectly. In such a case a high input can comprise an input that is indicative of the presence of a high light intensity. In a particular embodiment, light detector 2019 is in communication with a (potentially) light-emitting device and is capable of receiving a high input from the light-emitting device that indicates that the light-emitting device is in a condition (e.g., powered up and operating) that is likely to emit high light intensity. In this context, a high input can comprise any signal sent via a connection (whether a dedicated wire, an optical fiber, a wireless connection, an IR signal, a radiofrequency broadcast, and the like) that can be received by light detector 2019 and that indicates that light-emitting device is in a condition that is likely to emit high light intensity. In such an arrangement, the light-emitting device may include a communication unit that is capable of performing such communication with light detector 2019 via a connection. If desired, such an arrangement can include a provision for two-way communication such that the light-emitting device can receive an acknowledgement from system 2000 or other computing device, prior to the light-emitting device emitting light.

FIG. 20A also illustrates computing device 2017 comprising one or more computer processors and a memory comprising instructions that may be executed by the one or more computer processors. Computing device 2017 may include the same, a subset, or a superset of functionality and components illustrated and described in FIGS. 2 and 8. Computing device 2017 may be included in or attached to an article of personal protective equipment (e.g., system 2000), may be positioned on or attached to the worker in a separate device external to headtop 2010 and visor 2016, or may be in a remote computing device separate from the worker altogether (e.g., a remove server).

In accordance with this disclosure, computing device 2017 may receive, from light detector 2019, an indication that an intensity of light detected by the light detector exceeds an exposure threshold and/or that a type of light detected by the light detector matches a particular type of light. In some examples, the exposure threshold may be user-defined, hard-coded, or machine-generated. Computing device 2017 may determine, from the position sensor included in visor attachment assembly 2014, that the light-filtering shield is or is not positioned at the face of a worker to filter light with the intensity that exceeds the exposure threshold and/or the type of light matches a particular type. In some examples, computing device 2017 may determine that the light-filtering shield is or is not positioned at the face of a worker to filter light with the intensity that exceeds the exposure threshold within a threshold time at which the user was in a location during which the light exposure was present. As shown in FIG. 20A, visor 2016 is positioned at the face of a worker to filter light with the intensity that exceeds the exposure threshold (e.g., active position). As shown in FIG. 20B, visor 2016 is not positioned at the face of a worker to filter light with the intensity that exceeds the exposure threshold (e.g., standby position).

Computing device 2017 may generate, in response to the determination that the light-filtering shield is not positioned at the face of a worker to filter light with the intensity that exceeds the threshold and/or the type of light matches a particular type, an indication for output. In some examples, the indication of output may be haptic or audible and output at one or more computing devices as described in this disclosure. Computing device 1917 may generate any type of indication of output. In some examples, the indication of output may be a message that includes various notification data. Notification data may include but is not limited to: an alert, warning, or information message; a type of personal protective equipment; a worker identifier; a timestamp of when the message was generated; a position of the personal protective equipment; one or more light intensities, or any other descriptive information. In some examples, the message may be sent to one or more computing devices as described in this disclosure and output for display at one or more user interfaces of output devices communicatively coupled to the respective computing devices. In some examples computing device 2017 may receive an indication whether welding activity was occurring (e.g., welding arc was present) and generate the indication of output further based on whether the welding activity was occurring.

In some examples, there may be a first and second worker that are operating in the same work environment. The indication of the intensity of light detected by light detector 2019 may be based on the second worker performing a welding activity while facing in a first direction. A welding activity may include any activity that results in the creation or formation of a weld along one or more edges of physical material. Computing device 2017 may receive an indication of a direction in which the first worker is facing. For instance, the first and/or second workers may each be wearing a device that includes compass or other orientation detecting device that indications a bearing or orientation of the worker. Computing device 2017 may determine that the direction in which the first worker is facing at least has or will expose a face of the first worker to light from the welding activity of the second worker. As such, computing device 2017 may send, based on the determination that the direction in which the first worker is facing at least has or will expose a face of the first worker to light from the welding activity of the second worker, the indication for output to the first worker.

In some examples, to determine that the direction in which the first worker is facing at least has or will expose a face of the first worker to light from the welding activity of the second worker computing device 2017 may determine a first bearing of the direction in which the first worker is facing and determine a second bearing of the direction in which the second worker is facing. Computing device 2017 may determine an angle between the first and second bearings. Based on the angle, computing device 2017 may determine whether the angle between the first and second bearings satisfies a threshold. If the threshold is satisfied (e.g., less than or equal to for minor arc, or greater than or equal to for major arc), then computing device 2017 may send an indication for output to the first worker, such as a message.

In some examples, rather than waiting for a worker to be exposed to high-intensity light before notifying the worker, techniques and systems of this disclosure may proactively or preemptively notify the worker. A motion detector may be attached to a first worker and communicatively coupled to computing device 2017. Computing device 2017 may receive, prior to the first worker facing in the direction that exposes the face of the first worker to light from the welding activity of a second worker, a set of one or more indications of motion that indicate the face of the first worker is moving towards the direction of the light from the welding activity of the second worker. Computing device 2017 may send the indication for output to the first worker prior to the face of the first worker being exposed to light from the welding activity of the second worker. As such, the first worker may position visor 2016 in an active position. In some examples, if computing device 2017 determines that visor 2016 is already in the active position, no indication for output may be sent to the first worker. In some examples, computing device 2017 may send, prior to the first worker facing in a direction that exposes the face of the first worker to light from a welding activity of a second worker, an indication for output to the second worker. In some examples, the intensity of the notification (e.g., sound, visual appearance, haptic feedback) may increase as the exposure or likelihood of exposure to high-intensity light for the first worker increases. Accordingly, the second worker may stop or refrain from starting a welding activity until verifying that the first worker has placed visor 2016 into an active position.

Figure 21A:
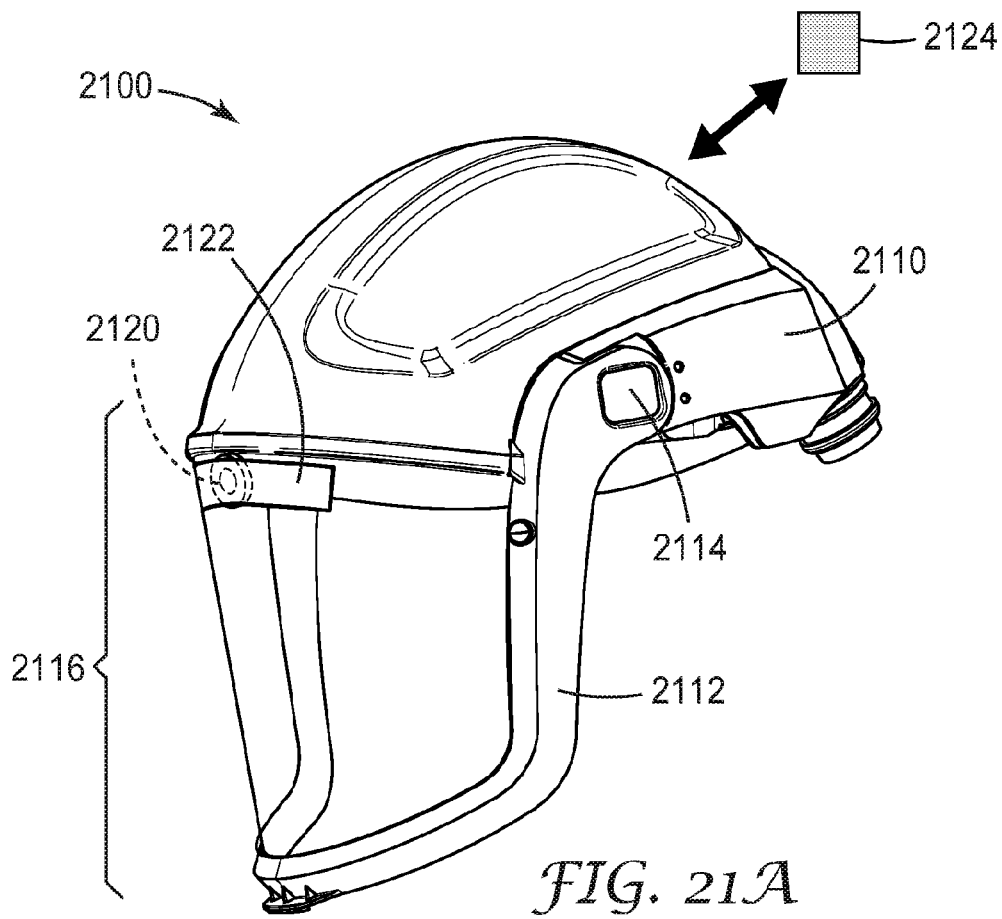
FIGS. 21A-21B illustrate a system that includes a headtop and a visor in accordance with this disclosure.
Figure 21B:
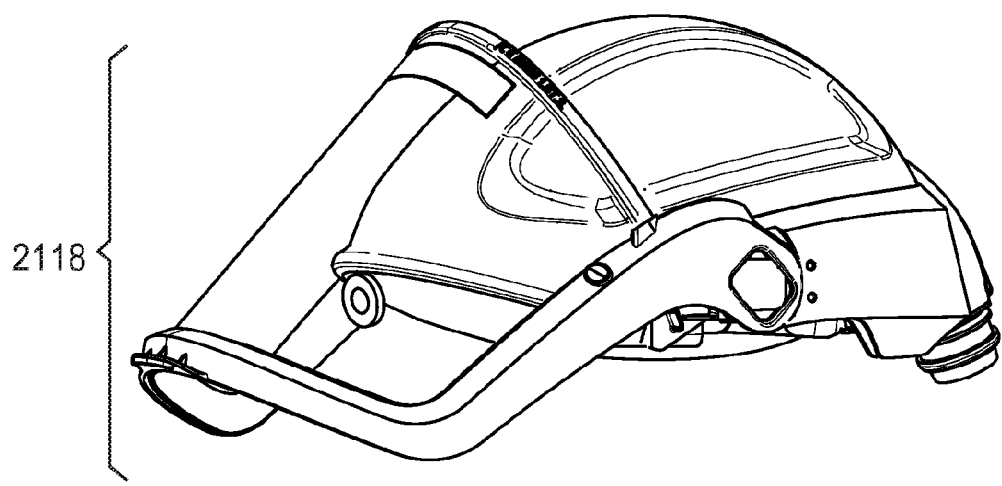

FIGS. 21A-21B illustrate a system 2100 in accordance with this disclosure. System 2100 may include a headtop 2110 and a visor 2112. In some examples, visor 2112 is physically coupled to headtop 2110 by a visor attachment assembly 2114. Visor attachment assembly 2114 may be attached directly or indirectly to a helmet, hard hat, strap, head band, or other head support, such as a head top 2110. Head top 2110 may be worn simultaneously with, and provide a support for, visor attachment assembly 2114. Visor attachment assembly 2114 may be integrated with or attached to an outer surface of head top 2110. Visor 2112 may rotate between one or more open and closed (e.g., active position 2116 in FIG. 21A and standby position 2118 in FIG. 21B) positions, such as further shown in FIG. 21B, by pivoting on an axis provided by visor attachment assembly 2114 that is orthogonal to the adjacent surface of visor 2112. In some instances, a computing device 2124 may be included at system 2100, may be positioned on or attached to the worker in a separate device external to system 2100, or may be in a remote computing device separate from the worker altogether (e.g., a remove server). In various examples, head top 2110 and visor attachment assembly 2114 may be joined using various suitable attachment components, such as snap-fit components, rivets, mechanical fasteners, adhesive, or other suitable attachment components as known in the art. Visor 2112 is configured to cover at least a portion of a user's face.

System 2100 may use an optical sensor 2120 to detect position changes of a reflective object 2122. In some examples, optical sensor 2120 is a camera that is capable of detecting one or more wavelength spectrums of light and/or generating images of objects detected in the one or more wavelength spectrums of light. In other examples, optical sensor 2120 comprises a light emitter and a photodiode. In such examples, the photodiode may generate different output signals based on different intensities of light detected by the photodiode. In some examples, the output signals may be proportional to the intensity of light detected by the photodiode. In some examples, a first spectral range may be from about 350 nm to about 700 nm (i.e., visible light spectrum) and a second spectral range may be from about 700 nm to about 1100 nm (i.e., near infrared spectrum or non-visible light spectrum). As further described in this disclosure, optical sensor 2120 may be mounted, affixed or otherwise positioned on headtop 2110. Various suitable attachment components, such as snap-fit components, rivets, mechanical fasteners, adhesive, or other suitable attachment components as known in the art may be used to attach optical sensor 2120 to headtop 2110.

Reflective object 2122 may be a reflective material that is visibly transparent in the visible light spectrum but reflects non-visible light in a non-visible light spectrum. In some examples, the reflective material may be applied to or embodied on the object to be sensed (e.g., the planar or semi-planar concave surface of the shield in visor 2112) or the object itself (e.g., the shield of visor 2112) is made of the retroreflective material. Light may be emitted from a non-visible light source (e.g., by optical sensor 2120 or light source separate from optical sensor 2120), such that reflective object 2122 reflects the non-visible light, which is captured by optical sensor 2120. Reflective object 2122 may be shaped such that an amount of non-visible light captured by optical sensor 2120 changes when the object moves. In this way and as further described in FIGS. 21A-21B, system 2100 may detect whether and/or to what degree visor 2112 is closed or open based on light reflected from visibly reflective object 2122 that is captured by optical sensor 2120 mounted on headtop 2110 (or any suitable helmet head suspension where optical sensor 2120 may be positioned on a portion of the suspension that wraps around the forehead of a person).

FIGS. 21A-21B, illustrate the detection of a position of visor 2112 using reflective object 2122 that is comprised of infra-red mirror film. Visor 2112 may be transparent or semi-transparent for usability by the user. In some examples, visor 2112 may be substantially transparent. In some examples, substantially transparent may be any opacity between 0-20% opacity. In some examples substantially transparent may be less than 20% opacity. In some examples, substantially transparent may be 5%, 10%, 15% or 20% opacity. In some examples, a pattern or shape of multi-layer IR reflective material (IR mirror film) is overlaid on the inside of the visor 2112, such as shown by reflective object 2122 overlaid or otherwise embodied on the planar surface of visor 2112. Optical sensor 2120, which may be an IR proximity sensor, is affixed to headtop 2110 and may contain both a photodiode and IR emitter as described above. Optical sensor 2120 may be positioned such that a highest possible amount (or at least a threshold amount) of emitted light reflects off reflective object 2122 (e.g., the IR mirror) into optical sensor 2120 when visor 2112 is completely closed (i.e., in active position 2116). As the position of visor 2112 relative to headtop 2110 changes from active position 2116 to standby position 2118, less reflected light is captured by the photodiode of optical sensor 2120. Accordingly, in some examples, optical sensor 2120 may generate signals proportional to the decreased light captured by the photodiode of optical sensor 2120.

In some examples, computing device 2124 may store data that indicates associations or relationships between positions of visor 2112 and degrees or intensities of light captured by optical sensor 2120. For instance, computing device 2124 may include a set of mappings that indicate angles or positions of visor 2112 and degrees or intensities of light captured by optical sensor 2120. In other examples, computing device 2124 may include a combination of hardware and/or software that defines a relation between angles or positions of visor 2112 and degrees or intensities of light captured by optical sensor 2120. In some examples, performance may be affected by sensor position and angle because the reflections off the film are specular. In some examples, the visor/film mirror may be concave with respect to optical sensor 2120 and thus may have a concentrating effect on the emitted light.

Computing device 2124, which may be communicatively coupled to optical sensor 2120, may perform one or more operations based on the signals or other indications generated by optical sensor 2120 that indicate the degrees or intensities of light captured. Example operations may include generating one or more indications of output, which may be visible, audible, or haptic. As an example, computing device 2124 may determine whether an operation of equipment by a worker and/or a location of a worker, such as a work environment, require that visor 2112 be positioned in an active position 2116. If computing device 2124 determines that operation of equipment by a worker and/or a location of a worker requires that visor 2112 be positioned in an active position 2116 and computing device 2124 determines that visor 2112 is in standby position 2118 or an intermediate position between active position 2116 and standby position 2118, computing device 2124 may generate an indication of output.

In some examples, the indication of output may be a message that includes various notification data. Notification data may include but is not limited to: an alert, warning, or information message; a type of personal protective equipment; a worker identifier; a timestamp of when the message was generated; a position of the personal protective equipment; or any other descriptive information. In some examples, the message may be sent to one or more computing devices as described in this disclosure and output for display at one or more user interfaces of output devices communicatively coupled to the respective computing devices. In some examples, the indication of output may be haptic or audible and output at one or more computing devices as described in this disclosure.

In some examples, the one or more operations performed by computing device 2124 may include disabling equipment to be used by the worker, denying access to locations that may otherwise be accessed by the user, or logging information associated with an event based on the position of visor 2112 or based on the signals or other indications generated by optical sensor 2120 that indicate the degrees or intensities of light captured.

In some examples, reflective object 2122 is comprised of a reflective material that is patterned. In some examples, reflective object 2122 may be partially or fully occluded by an absorbing material/object. In some examples, reflective object 2122 is multi-layer optical film. In some examples, reflective object 2122 is a retroreflective material. In some examples, optical sensor 2120 emits and/or captures only non-visible light (e.g., IR light) only. In some examples, reflective object 2122 reflects only non-visible light (e.g., IR light). In some examples, optical sensor 2120 includes a light detector and light emitter are combined in an integrated circuit.

It will be appreciated that numerous and varied other arrangements may be readily devised by those skilled in the art without departing from the spirit and scope of the invention as claimed. For example, each of the communication modules in the various devices described throughout may be enabled to communicate as part of a larger network or with other devices to allow for a more intelligent infrastructure. Information gathered by various sensors may be combined with information from other sources, such as information captured through a video feed of a work space or an equipment maintenance space. In some instances, a portal configuration may be used such that if any of the systems described herein detect that a user or worker has exceeded a given threshold (whether high or low), the worker is prevented from physically gaining access to a particular work space or other area. Information gathered by the systems described herein can be used for further data analytics to determine compliance with various rules or regulations, and to improve safety processes. In some instances, a geo-location device, such as a global positioning system (GPS) may be incorporated into any of the systems described herein to provide user location. In some instances, the information collected by the systems and sensors described herein may be used to determine remaining service life of any PPE.

It will be appreciated that based on the above description, aspects of the disclosure include methods and systems for determining time of use (wear time) of articles, such as PPE articles, by determining if they satisfy at least one criterion.

Additional features and components can be added to each of the systems described above.

In some instances the clean air supply source comprises at least one of: a powered air purifying respirator (PAPR) and a self-contained breathing apparatus (SCBA).

In some instances the position sensor comprises at least one of: an accelerometer, gyro, magnet, switch or air pressure sensor.

In some instances the system further comprises an environmental beacon, wherein the environmental beacon comprises the environmental sensor and a communication module.

In some instances, the environmental beacon communication module includes at least one of: RFID, Bluetooth and WiFi communication capabilities.

In some instances, the alarm comprises at least one of: tactile, vibration, audible, visual, heads-up display or radio frequency signal.

In some instances, the head top communication module includes at least one of: radio frequency identification (RFID), Bluetooth and WiFi communication capabilities.

In some instances the personal communication hub includes at least one of: RFID, Bluetooth and WiFi communication capabilities.

In some instances the signal indicating the presence of the hazard is a location signal.

In some instances the signal indicating the presence of the hazard is generated based on detection of a hazard by an environmental sensor.

In some instances the environmental sensor determines the presence of a hazard when a contaminant level exceeds a designated hazard threshold.

In some instances the designated hazard threshold is configurable by the user.

In some instances the designated hazard threshold is stored on at least one of the environmental sensor and the personal communication hub.

In some instances the alert is generated after the visor has been in an open position for a period of time exceeding a designated exposure threshold.

In some instances the exposure threshold is configurable by the user.

In some instances the exposure threshold is stored on at least one of the head top and the personal communication hub.

In some instances the personal communication hub can be worn or carried.

In some instances the head top further comprises a head detection sensor.

In some instances the alert is only generated if the head detection sensor detects that the head top is being worn by the user.

In some instances the position sensor detects if the visor is in a partially open position.

In some instances, the system further comprises a temperatures sensor on the interior of the head top.

The present disclosure further includes a method of alerting a person or a worker when hazardous exposure is detected. The method comprises providing a head top comprising: a visor that is sized to fit over at least the user's nose and mouth, a position sensor, and a head top communication module. The method further comprises detecting with the position sensor whether the visor is in an open or a closed position. The method further comprises detecting the presence of a hazard and generating an alert if the visor is in an open position and if a hazard is present.

In some instances the presence of the hazard is detected by an environmental sensor.

In some instances the environmental sensor determines the presence of a hazard when a contaminant level exceeds a designated hazard threshold.

In some instances the alert is generated after the visor has been in an open position for a period of time exceeding a designated exposure threshold.

In some instances the head top further comprises a head detection sensor, and wherein the alert is only generated if the head detection sensor detects that the head top is being worn by the user.

In some instances the method further comprises detecting if the visor is in a partially open position.

In some instances the head top further comprises a temperature sensor, wherein the temperature sensor detects the temperature in the interior of the head top.

In an example, a method comprises obtaining usage data from at least one air respirator system, wherein the usage data comprises data indicative of operation of the at least one air respirator system; applying, by an analytics engine, the usage data to a safety learning model that characterizes activity of a user of the at least one air respirator system; predicting a likelihood of an occurrence of a safety condition associated with the at least one air respirator system based on application of the usage data to the safety learning model; and generating an output in response to predicting the likelihood of the occurrence of the safety event.

In another example, a system comprises a respirator comprising one or more electronic sensors, the one or more electronic sensors configured to generate data that is indicative of an operation of the respirator; and one or more servers. The servers are configured to receive the data that is indicative of the operation of the respirator; apply the data to a safety learning model to predict a likelihood of an occurrence of a safety event associated with the respirator; generate an alert in response to predicting the likelihood of the occurrence of the safety event; and transmit the alert to the respirator; and wherein the respirator is configured to receive the alert and generate an output in response to receiving the alert.

In another example, a method comprises outputting, for display by a computing device, a user interface (UI) having a plurality of user-selectable filters for filtering usage data from at least one respirator; receiving, by the computing device, at least one indication of filter selections for the user-selectable filters; and outputting, for display by the computing device, UI content based on the filter selections, the UI content being indicative of the usage data corresponding to the filter selections.

A method comprising: outputting, for display by a computing device, a user interface (UI) having a plurality of user-selectable filters for filtering usage data from at least one respirator; receiving, by the computing device, at least one indication of filter selections for the user-selectable filters; and outputting, for display by the computing device, UI content based on the filter selections, the UI content being indicative of the usage data corresponding to the filter selections.

The method of claim 21, wherein the plurality of user-selectable filters comprises at least two of user identification of a user of a respirator of the at least one respirator, components of the at least one respirator, a geographic location, a time, a temperature, a motion of the user, an ambient noise, an impact to the at least one respirator, a posture of the user of the at least one respirator, a battery status of a battery of the at least one respirator, a visor position of a visor of the at least one respirator, a presence of a head in a head top of the at least one respirator, a pressure of a blower of the at least one respirator, a blower speed of the blower of the at least one respirator, a filter status of a filter of the at least one respirator, or a status of a cartridge of the at least one respirator.

The method of claim 21, further comprising: outputting, for display by the computing device, a second plurality of user-selectable filters for filtering alert types from the at least one respirator; receiving, by the computing device, second filter selections for the second plurality of user-selectable filters; and outputting, for display by the computing device, second UI content based on the second filter selections, the second UI content being indicative of the alert types corresponding to the second filter selections.

The method of claim 21, wherein outputting the second UI content based on the filter selections comprises outputting UI content that indicates the usage data over a time domain.

The method of claim 24, wherein outputting the UI content that indicates the usage data over a time domain comprises simultaneously outputting UI content for at least two types of usage data.

The method of claim 24, wherein the at least two types of usage data comprises at least two of a geographic location, a time, a temperature, a motion of the user, an ambient noise, an impact to the at least one respirator, a posture of the user of the at least one respirator, a battery status of a battery of the at least one respirator, a visor position of a visor of the at least one respirator, a presence of a head in a head top of the at least one respirator, a pressure of a blower of the at least one respirator, a blower speed of the blower of the at least one respirator, a filter status of a filter of the at least one respirator, or a status of a cartridge of the at least one respirator.

The method of claim 21, wherein the at least one respirator comprises a plurality of respirators that correspond to respective users.

Although the methods and systems of the present disclosure have been described with reference to specific exemplary embodiments, those of ordinary skill in the art will readily appreciate that changes and modifications may be made thereto without departing from the spirit and scope of the present disclosure.

In the present detailed description of the preferred embodiments, reference is made to the accompanying drawings, which illustrate specific embodiments in which the invention may be practiced. The illustrated embodiments are not intended to be exhaustive of all embodiments according to the invention. It is to be understood that other embodiments may be utilized and structural or logical changes may be made without departing from the scope of the present invention. The following detailed description, therefore, is not to be taken in a limiting sense, and the scope of the present invention is defined by the appended claims.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

Spatially related terms, including but not limited to, "proximate," "distal," "lower," "upper," "beneath," "below," "above," and "on top," if used herein, are utilized for ease of description to describe spatial relationships of an element(s) to another. Such spatially related terms encompass different orientations of the device in use or operation in addition to the particular orientations depicted in the figures and described herein. For example, if an object depicted in the figures is turned over or flipped over, portions previously described as below or beneath other elements would then be above or on top of those other elements.

As used herein, when an element, component, or layer for example is described as forming a "coincident interface" with, or being "on," "connected to," "coupled with," "stacked on" or "in contact with" another element, component, or layer, it can be directly on, directly connected to, directly coupled with, directly stacked on, in direct contact with, or intervening elements, components or layers may be on, connected, coupled or in contact with the particular element, component, or layer, for example. When an element, component, or layer for example is referred to as being "directly on," "directly connected to," "directly coupled with," or "directly in contact with" another element, there are no intervening elements, components or layers for example. The techniques of this disclosure may be implemented in a wide variety of computer devices, such as servers, laptop computers, desktop computers, notebook computers, tablet computers, hand-held computers, smart phones, and the like. Any components, modules or units have been described to emphasize functional aspects and do not necessarily require realization by different hardware units. The techniques described herein may also be implemented in hardware, software, firmware, or any combination thereof. Any features described as modules, units or components may be implemented together in an integrated logic device or separately as discrete but interoperable logic devices. In some cases, various features may be implemented as an integrated circuit device, such as an integrated circuit chip or chipset. Additionally, although a number of distinct modules have been described throughout this description, many of which perform unique functions, all the functions of all of the modules may be combined into a single module, or even split into further additional modules. The modules described herein are only exemplary and have been described as such for better ease of understanding.

If implemented in software, the techniques may be realized at least in part by a computer-readable medium comprising instructions that, when executed in a processor, performs one or more of the methods described above. The computer-readable medium may comprise a tangible computer-readable storage medium and may form part of a computer program product, which may include packaging materials. The computer-readable storage medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The computer-readable storage medium may also comprise a non-volatile storage device, such as a hard-disk, magnetic tape, a compact disk (CD), digital versatile disk (DVD), Blu-ray disk, holographic data storage media, or other non-volatile storage device.

The term "processor," as used herein may refer to any of the foregoing structure or any other structure suitable for implementation of the techniques described herein. In addition, in some aspects, the functionality described herein may be provided within dedicated software modules or hardware modules configured for performing the techniques of this disclosure. Even if implemented in software, the techniques may use hardware such as a processor to execute the software, and a memory to store the software. In any such cases, the computers described herein may define a specific machine that is capable of executing the specific functions described herein. Also, the techniques could be fully implemented in one or more circuits or logic elements, which could also be considered a processor.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media, which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor", as used may refer to any of the foregoing structure or any other structure suitable for implementation of the techniques described. In addition, in some aspects, the functionality described may be provided within dedicated hardware and/or software modules. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

It is to be recognized that depending on the example, certain acts or events of any of the methods described herein can be performed in a different sequence, may be added, merged, or left out all together (e.g., not all described acts or events are necessary for the practice of the method). Moreover, in certain examples, acts or events may be performed concurrently, e.g., through multi-threaded processing, interrupt processing, or multiple processors, rather than sequentially.

In some examples, a computer-readable storage medium includes a non-transitory medium. The term "non-transitory" indicates, in some examples, that the storage medium is not embodied in a carrier wave or a propagated signal. In certain examples, a non-transitory storage medium stores data that can, over time, change (e.g., in RAM or cache). Various examples have been described. These and other examples are within the scope of the following claims.

What is claimed is:

1. A system comprising:
a hearing protector;
at least one position sensor;
at least one sound monitoring sensor;
at least one computing device communicatively coupled to the at least one position sensor and the at least one sound monitoring sensor, the at least one computing device comprising a memory and one or more computer processors that:
receive, from the at least one sound monitoring sensor and over a time duration, indications of sound levels to which a worker is exposed;
determine, from the at least one position sensor and during the time duration, that the hearing protector is not positioned at one or more ears of the worker to attenuate the sound levels; and
generate, in response to the determination that at least one of the sound levels satisfies an exposure threshold during the time duration and the hearing protector is not positioned at one or more ears of the worker to attenuate the sound levels and that a noise level in a work environment of the worker is greater than or equal to a work environment noise threshold, an indication for output.

2. The system of claim 1, comprising a second sound monitoring sensor, wherein the at least one sound monitoring sensor is a first sound monitoring sensor, wherein the indications of sound levels are first indications of sound levels, wherein the first sound monitoring sensor is included within a cup of an ear muff of the hearing protector and the second sound monitoring sensor is external to cup of the ear muff, and wherein the one or more computer processors:
receive, from the second sound monitoring sensor, second indications of sound levels;

determine a difference between at least one of the first indications of sound levels and at least one of the second indications of sound levels; and in response to a determination that the difference is less than or equal to a difference threshold, generate the indication for output.

3. The system of claim 1, wherein the one or more computer processors:

determine a location of the worker; and wherein the determination that at least one of the sound levels satisfies the exposure threshold during the time duration and the hearing protector is not positioned at one or more ears of the worker to attenuate the sound levels further comprises a determination that the location of the worker is within a distance threshold of a location that corresponds to the at least one of the sound levels that satisfies the exposure threshold.

4. The system of claim 1, wherein the computing device is at least one of physically integrated with the hearing protector, physically separate from the hearing protector and attached to the worker, or physically separate from the hearing protector and not attached to worker.

5. The method of claim 1, wherein the computing device is at least one of physically integrated with the hearing protector, physically separate from the hearing protector and attached to the worker, or physically separate from the hearing protector and not attached to worker.

6. A hearing protector comprising:

a head-mounted device;

at least one position sensor coupled to the head-mounted device;

one or more ear muffs coupled to the at least one position sensor; and a computing device communicatively coupled to the at least one position sensor and the at least one sound monitoring sensor, the at least one computing device comprising a memory and one or more computer processors to:

receive, from at least one sound monitoring sensor and over a time duration, indications of sound levels to which a worker is exposed;

determine, from the at least one position sensor and during the time duration, that the hearing protector is not positioned at one or more ears of the worker to attenuate the sound levels; and generate, in response to the determination that at least one of the sound levels satisfies an exposure threshold during the time duration and the hearing protector is not positioned at one or more ears of the worker to attenuate the sound levels and that a noise level in a work environment of the worker is greater than or equal to a work environment noise threshold, an indication for output.

7. The hearing protector of claim 6, comprising a second sound monitoring sensor, wherein the at least one sound monitoring sensor is a first sound monitoring sensor, wherein the indications of sound levels are first indications of sound levels, wherein the first sound monitoring sensor is included within a cup of the one or more ear muffs and the second sound monitoring sensor is external to the cup of the one or more ear muffs, and wherein the one or more computer processors:

receive, from the second sound monitoring sensor, second indications of sound levels;

determine a difference between at least one of the first indications of sound levels and at least one of the second indications of sound levels; and in response to a determination that the difference is less than or equal to a difference threshold, generate the indication for output.

8. The hearing protector of claim 6, wherein the one or more computer processors:

determine a location of the worker; and wherein the determination that at least one of the sound levels satisfies the exposure threshold during the time duration and the hearing protector is not positioned at one or more ears of the worker to attenuate the sound levels further comprises a determination that the location of the worker is within a distance threshold of a location that corresponds to the at least one of the sound levels that satisfies the exposure threshold.

9. The hearing protector of claim 6, wherein the computing device is at least one of physically integrated with the hearing protector, physically separate from the hearing protector and attached to the worker, or physically separate from the hearing protector and not attached to worker.

10. A method comprising:

receiving, by a computing device, from at least one sound monitoring sensor and over a time duration, indications of sound levels to which a worker is exposed;

determining, from at least one position sensor and during the time duration, that a hearing protector is not positioned at one or more ears of the worker to attenuate the sound levels; and generating, in response to determining that at least one of the sound levels satisfies an exposure threshold during the time duration and the hearing protector is not positioned at one or more ears of the worker to attenuate the sound levels and that a noise level in a work environment of the worker is greater than or equal to a work environment noise threshold, an indication for output.

11. The method of claim 10, further comprising:

receiving, from a second sound monitoring sensor, second indications of sound levels, wherein the at least one sound monitoring sensor is a first sound monitoring sensor, wherein the indications of sound levels are first indications of sound levels, wherein the first sound monitoring sensor is included within a cup of an ear muff of the hearing protector and the second sound monitoring sensor is external to cup of the ear muff;

determining a difference between at least one of the first indications of sound levels and at least one of the second indications of sound levels; and in response to a determination that the difference is less than or equal to a difference threshold, generating the indication for output.

12. The method of claim 10, further comprising:

determining a location of the worker; and wherein determining that at least one of the sound levels satisfies the exposure threshold during the time duration and the hearing protector is not positioned at one or more ears of the worker to attenuate the sound levels further comprises determining that the location of the worker is within a distance threshold of a location that corresponds to the at least one of the sound levels that satisfies the exposure threshold.

13. A computing device comprising:

a memory; and one or more computer processors that:

receive, from at least one sound monitoring sensor and over a time duration, indications of sound levels to which a worker is exposed;

determine, from at least one position sensor and during the time duration, that hearing protector is not positioned at one or more ears of the worker to attenuate the sound levels; and generate, in response to determining that at least one of the sound levels satisfies a threshold during the time duration and the hearing protector is not positioned at one or more ears of the worker to attenuate the sound levels and that a noise level in a work environment of the worker is greater than or equal to a work environment noise threshold, an indication for output.

14. The computing device of claim 13, wherein the one or more computer processors:

receive, from a second sound monitoring sensor, second indications of sound levels, wherein the at least one sound monitoring sensor is a first sound monitoring sensor, wherein the indications of sound levels are first indications of sound levels, wherein the first sound monitoring sensor is included within a cup of an ear muff of the hearing protector and the second sound monitoring sensor is external to cup of the ear muff;

determine a difference between at least one of the first indications of sound levels and at least one of the second indications of sound levels; and in response to a determination that the difference is less than or equal to a difference threshold, generate the indication for output.

15. The computing device of claim 13, wherein the one or more computer processors:

determine a location of the worker; and wherein the determination that at least one of the sound levels satisfies the exposure threshold during the time duration and the hearing protector is not positioned at one or more ears of the worker to attenuate the sound levels further comprises determining that the location of the worker is within a distance threshold of a location that corresponds to the at least one of the sound levels that satisfies the exposure threshold.

16. The computing device of claim 13, wherein the computing device is at least one of physically integrated with the hearing protector, physically separate from the hearing protector and attached to the worker, or physically separate from the hearing protector and not attached to worker.

* * * * *